United States Patent
Pérez-Jiménez et al.

(10) Patent No.: US 11,286,508 B2
(45) Date of Patent: Mar. 29, 2022

(54) ANCESTRAL CELLULASES AND USES THEREOF

(71) Applicants: CIC NANOGUNE—ASOCIACIÓN CENTRO DE INVESTIGACIÓN COOPERATIVA EN NANOCIENCIAS, Guipuzcoa (ES); UNIVERSIDAD DEL PAÍS VASCO, Vizcaya (ES)

(72) Inventors: Raúl Pérez-Jiménez, San Sebastian (ES); Nerea Barruetabeña Garate, Guipuzcoa (ES); Mª Aranzazu Eceiza Mendiguren, Donostia-San Sebastián (ES)

(73) Assignees: Universidad del País Vasco, Leioa-Vizcaya (ES); CIC nanoGune—Asociación Centro de Investigación Coonerativa en Nanociencias, Guipuzcoa (ES)

( * ) Notice: Subject to any disclaimer, the term of this patent is extended or adjusted under 35 U.S.C. 154(b) by 0 days.

(21) Appl. No.: 16/955,254

(22) PCT Filed: Dec. 18, 2018

(86) PCT No.: PCT/EP2018/085548
§ 371 (c)(1),
(2) Date: Jun. 18, 2020

(87) PCT Pub. No.: WO2019/121719
PCT Pub. Date: Jun. 27, 2019

(65) Prior Publication Data
US 2020/0392542 A1 Dec. 17, 2020

(30) Foreign Application Priority Data
Dec. 19, 2017 (EP) .................................. EP17382862

(51) Int. Cl.
| | |
|---|---|
| *C12P 7/08* | (2006.01) |
| *C12P 19/14* | (2006.01) |
| *C12N 9/42* | (2006.01) |
| *C12P 7/10* | (2006.01) |
| *C12N 9/24* | (2006.01) |

(52) U.S. Cl.
CPC .............. *C12P 7/08* (2013.01); *C12N 9/2437* (2013.01); *C12N 9/2445* (2013.01); *C12P 7/10* (2013.01); *C12P 19/14* (2013.01); *C12Y 110/03002* (2013.01); *C12Y 302/01004* (2013.01); *C12Y 302/01008* (2013.01); *C12Y 302/01021* (2013.01); *C12Y 302/01091* (2013.01)

(58) Field of Classification Search
None
See application file for complete search history.

(56) References Cited

U.S. PATENT DOCUMENTS

| | | | |
|---|---|---|---|
| 5,612,055 A | 3/1997 | Bedford et al. | |
| 6,599,722 B2 | 7/2003 | Boston et al. | |
| 9,102,955 B2 * | 8/2015 | McBride | .................. C12P 7/14 |
| 2009/0203107 A1 * | 8/2009 | Thompson | ........... C12N 9/2402 |
| | | | 435/202 |
| 2011/0306105 A1 * | 12/2011 | Chen | .................... C12N 9/2437 |
| | | | 435/165 |
| 2013/0323822 A1 * | 12/2013 | Brevnova | ............ C12N 9/2482 |
| | | | 435/254.21 |
| 2018/0171271 A1 * | 6/2018 | Skagerlind | ......... C11D 3/38645 |

FOREIGN PATENT DOCUMENTS

| | | |
|---|---|---|
| EP | 0473545 A2 | 3/1992 |
| EP | 1222256 B1 | 5/2005 |
| EP | 1852508 A2 | 11/2007 |
| WO | 9206209 A1 | 4/1992 |
| WO | 9720920 A1 | 6/1997 |

(Continued)

OTHER PUBLICATIONS

Uniprot, Accession No. A0A229HF88, 2017, www.uniprot.org (Year: 2017).*
Uniprot, Accession No. P14002, 2017, www.uniprot.org. (Year: 2017).*
Oliveria et al., An alkaline thermostable recombinant Humicola grisea var. thermoidea cellobiohydrolase presents bifunctional (endo/exoglucanase) activity on cellulosic substrates, World J. Microbiol. Biotechnol. 29, 2013, 19-26. (Year: 2013).*

(Continued)

*Primary Examiner* — Robert B Mondesi
*Assistant Examiner* — Todd M Epstein
(74) *Attorney, Agent, or Firm* — Pilloff Passino & Cosenza LLP; Sean A. Passino; Rachel K. Pilloff

(57) ABSTRACT

The invention relates to a polypeptide comprising an exoglucanase catalytic domain comprising a sequence selected from the group consisting of SEQ ID NO: 1, SEQ ID NO: 2 and SEQ ID NO: 3, and to a polypeptide having beta-glucosidase activity comprising a sequence selected from the group consisting of SEQ ID NO: 6, SEQ ID NO: 7 and SEQ ID NO: 8, and to functionally equivalent variants thereof that maintain or improve their catalytic activity. Additionally, the invention relates to an enzyme cocktail comprising said polypeptide(s) and an endoglucanase. Further, the invention also relates to methods for hydrolysing cellulose to cellobiose and/or cellotetraose, cellobiose and/or cellotetraose to glucose and cellulose to glucose, and to produce bioethanol, using the polypeptides or enzyme cocktails of the invention, and to the uses of the polypeptides and enzyme cocktails of the invention for hydrolysing cellulose to cellobiose and/or cellotetraose, cellobiose and/or cellotetraose to glucose and cellulose to glucose, and to produce bioethanol.

11 Claims, 9 Drawing Sheets

Specification includes a Sequence Listing.

(56) References Cited

FOREIGN PATENT DOCUMENTS

| WO | 98021339 A1 | 5/1998 | | |
|---|---|---|---|---|
| WO | 2009108941 A2 | 9/2009 | | |
| WO | WO-2010060056 A2 | * | 5/2010 | ............. C12N 15/80 |
| WO | WO-2013166312 A1 | * | 11/2013 | ........... C12N 9/2437 |
| WO | 2017121902 A1 | 7/2017 | | |

OTHER PUBLICATIONS

Genbank, Accession No. AEV40916.1, 2016, www.ncbi.nlm.nih.gov. (Year: 2016).*

Machida et al., Nucleotide sequence of *Saccharomycopsis fibuligera* genes for extracellular beta-glucosidases as expressed in *Saccharomyces cerevisiae*, Appl. Environ. Microbiol. 54, 1988, 3174-55. (Year: 1988).*

Barruetabena et al., Resurrection of efficient Precambrian endoglucanases for lignocelulosic biomass hydrolysis, Comm. Chem. 2, 2019, 76. (Year: 2019).*

Cai et al., Reconstruction of ancestral protein sequences and its applications, BMC Evol. Biol. 4, 2004, 33. (Year: 2004).*

Database Geneseq, Apr. 12, 2012, Streptomyces avermitilis MA-1680 endoglucanase SAV1855 protein, SEQ 6, XP002787954, EBI AZT83950.

Database Geneseq, Aug. 7, 2008. "Streptomyces avermitilis amino acid sequence SEQ ID 9394".

Database Uniprot, Jun. 11, 2014, EBI A0A014LN52.

Datase Geneseq, Aug. 4, 2011, C. Thermocellum beta-glucosidase B-related glycosidase, XP002781018.

Herman Van Tilbeurgh et al., "Studies of the cellulolytic system of Trichoderma reesei QM 9414 Reaction specificity and thermodynamics of interactions of small substrates and ligands with the 1,4-βglucan cellobiohydrolase II," European Journal of Biochemistry, Apr. 1985, pp. 329-334, vol. 148.

Mukund V. Deshpande et al., "An assay for selective determination of exo-1,4,-βglucanases in a mixture of cellulolytic enzymes," Analytical Biochemistry, May 1984, pp. 481-487, vol. 138, Issue 2.

S. Kohring et al., "Subunit Composition and Glycosidic Activities of the Cellulase Complex from Clostridium thermocellum JW20," Applied and Environmental Microbiology, Dec. 1990, pp. 3,798-3,804, vol. 56, No. 12.

Jonathan Caspi et al., "Conversion of Thermobifida fusca free exoglucanases into cellulosomal components comparative impact on cellulose-degrading activity," Journal of Biotechnology, Jul. 2008, pp. 351-357, vol. 135.

Pierre-Emmanuel Courty et al., "Activity profiling of ectomycorrhiza communities in two forest soils using multiple enzymatic tests," New Phytologist, Jul. 2005, pp. 309-319, vol. 167.

Stephen F. Altschul et al., "Basic Local Alignment Search Tool," J. Mol. Biol., Oct. 1990, pp. 403-410, vol. 215.

Hyeon-Dong Kim et al., "Enzyme-linked Assay of Cellulose-binding Domain Functions from Cellulomonas fimi on Multi-well Microtiter Plate," Biotechnology and Bioprocess Engineering, pp. 575-580, Jun. 2013, vol. 18.

T. K. Ghose et al., "Measurement of Hemicellulase Activities Part 1: XYLANASES," Pure & AppL Chem., Jan. 1987, pp. 1739-1752, vol. 59, No. 12.

Makoto Machida et al., "Nucleotide Sequences of Saccharomycopsis fibuligera Genesfor Extracellular r-Glucosidases as Expressed in *Saccharomyces cerevisiae*," Applied and Environmental Microbiology, Dec. 1988, pp. 3,147-3,155, vol. 54, No. 12.

Yasuhiko Nozaki, "Determination of the concenlration of protein by dry weight—A comparison with spectrophotometric methods," Archives of Biochemistry and Biophysics, Sep. 1986, pp. 437-446, vol. 249, No. 2.

Gail Lorenz Miller, "Use of Dinitrosalicylic Acid Reagent for Determination of Reducing Sugar," Anal. Chem., Mar. 1959, pp. 426-428, vol. 31, No. 3.

U.S. Van Dyk et al., "A review of lignocellulose bioconversion using enzymatic hydrolysis and synergistic cooperation between enzymes—Factors affecting enzymes, conversion and synergy," Biotechnology Advances, Nov. 2012, pp. 1,458-1,480, vol. 30.

International Search Report & Written Opinion for PCT/EP2018/085548, dated Mar. 29, 2019.

* cited by examiner

C

D

SEQUENCE LISTING

```
<160> NUMBER OF SEQ ID NOS: 44

<210> SEQ ID NO 1
<211> LENGTH: 626
<212> TYPE: PRT
<213> ORGANISM: Artificial Sequence
<220> FEATURE:
<223> OTHER INFORMATION: Ancestral exoglucanase catalytic domain

<400> SEQUENCE: 1

Asp Asn Ala Tyr Glu Gln Arg Phe Leu Asp Met Tyr Asn Lys Ile Lys
1               5                   10                  15

Asp Pro Ala Asn Gly Tyr Phe Ser Pro Glu Gly Ile Pro Tyr His Ser
            20                  25                  30

Val Glu Thr Leu Ile Val Glu Ala Pro Asp Tyr Gly His Glu Thr Thr
        35                  40                  45

Ser Glu Ala Phe Ser Tyr Tyr Leu Trp Leu Glu Ala Met Tyr Gly Arg
    50                  55                  60

Phe Thr Gly Asp Trp Ser Gly Phe Asn Asn Ala Trp Asp Thr Met Glu
65                  70                  75                  80

Lys Tyr Ile Ile Pro Ser His Ala Asp Gln Pro Thr Thr Ser Ser Tyr
                85                  90                  95

Asn Pro Asn Lys Pro Ala Thr Tyr Ala Pro Glu His Pro Asp Pro Ser
            100                 105                 110

Gln Tyr Pro Ser Gln Leu Asp Ser Ser Ala Pro Val Gly Lys Asp Pro
        115                 120                 125

Ile Asp Asn Glu Leu Lys Ser Thr Tyr Gly Thr Asn Gln Ile Tyr Gly
    130                 135                 140

Met His Trp Leu Leu Asp Val Asp Asn Trp Tyr Gly Phe Gly Asn Ser
145                 150                 155                 160

Pro Gly Arg Cys Glu Asp Gly Asp Ser Thr Thr Arg Pro Ala Tyr Ile
                165                 170                 175

Asn Thr Phe Gln Arg Gly Glu Gln Glu Ser Val Trp Glu Thr Ile Pro
            180                 185                 190
```

```
Gln Pro Ser Arg Asp Glu Met Lys Tyr Gly Gly Pro Asn Gly Phe Leu
            195                 200                 205

Asp Leu Phe Thr Gly Asp Ser Gln Tyr Pro Ala Lys Gln Trp Lys Tyr
    210                 215                 220

Thr Asn Ala Pro Asp Ala Asp Ala Arg Ala Val Gln Ala Thr Tyr Trp
225                 230                 235                 240

Ala His Glu Trp Ala Lys Glu Gln Gly Val Ala Ser Asn Val Ser Ala
                245                 250                 255

Tyr Val Ala Lys Ala Thr Lys Met Gly Asp Tyr Leu Arg Tyr Ser Met
            260                 265                 270

Phe Asp Lys Tyr Phe Arg Lys Ile Gly Asn Cys Val Gly Ala Ser Ser
        275                 280                 285

Thr Pro Ala Gly Thr Gly Lys Asp Ser Ala His Tyr Leu Leu Ser Trp
    290                 295                 300

Tyr Tyr Ala Trp Gly Gly Ile Asp Thr Ser Ala Asn Trp Ala Trp
305                 310                 315                 320

Arg Ile Gly Ser Ser His Ser His Phe Gly Tyr Gln Asn Pro Met Ala
                325                 330                 335

Ala Trp Ala Leu Ser Asn Ala Ser Glu Leu Lys Pro Lys Ser Pro Thr
            340                 345                 350

Gly Ala Ser Asp Trp Ala Lys Ser Leu Lys Arg Gln Leu Glu Phe Tyr
        355                 360                 365

Gln Trp Leu Gln Ser Ser Glu Gly Ala Ile Ala Gly Gly Ala Thr Asn
    370                 375                 380

Ser Trp Asn Gly Ser Tyr Ala Thr Trp Pro Ala Gly Thr Ser Thr Phe
385                 390                 395                 400

Tyr Gly Met Gly Tyr Glu Glu Gln Pro Val Tyr His Asp Pro Pro Ser
                405                 410                 415

Asn Gln Trp Phe Gly Met Gln Ala Trp Ser Met Glu Arg Val Ala Glu
            420                 425                 430

Tyr Tyr Tyr Lys Thr Gly Asp Thr Arg Ala Lys Ser Val Leu Asp Lys
        435                 440                 445

Trp Val Lys Trp Ala Lys Ala Asn Val Thr Ile Asn Ala Asp Gly Thr
    450                 455                 460

Phe Gln Ile Pro Gly Asn Leu Glu Trp Ser Gly Gln Pro Asp Thr Trp
465                 470                 475                 480

Thr Ala Ser Tyr Thr Gly Ala Asn Pro Asn Leu His Val Thr Val Lys
                485                 490                 495

Asn Tyr Gly Gln Asp Val Gly Val Ala Gly Ser Leu Ala Lys Ala Leu
            500                 505                 510

Thr Tyr Tyr Ala Ala Lys Ser Gly Asn Thr Thr Ala Lys Asp Thr Ala
        515                 520                 525

Lys Lys Leu Leu Asp Ala Leu Asn Asn Tyr Gln Asp Ser Lys Gly Ile
    530                 535                 540

Ala Val Pro Glu Thr Arg Ala Asp Tyr Asn Arg Phe Phe Asp Glu Val
545                 550                 555                 560

Tyr Val Pro Ser Gly Trp Thr Gly Thr Met Pro Asn Gly Asp Val Ile
                565                 570                 575

Lys Ser Gly Ala Thr Phe Leu Asp Ile Arg Ser Lys Tyr Lys Gln Asp
            580                 585                 590

Pro Asp Trp Pro Lys Val Glu Ala Ala Leu Gln Ser Gly Pro Ala Pro
        595                 600                 605
```

Thr Phe Thr Tyr His Arg Phe Trp Ala Gln Val Asp Ile Ala Thr Ala
610             615                 620

Tyr Ala
625

<210> SEQ ID NO 2
<211> LENGTH: 626
<212> TYPE: PRT
<213> ORGANISM: Artificial Sequence
<220> FEATURE:
<223> OTHER INFORMATION: Ancestral exoglucanase catalytic domain

<400> SEQUENCE: 2

Asp Asn Ala Tyr Asp Gln Arg Phe Leu Thr Met Tyr Asn Lys Ile Lys
1               5                   10                  15

Asp Pro Ala Asn Gly Tyr Phe Ser Pro Glu Gly Val Pro Tyr His Ser
            20                  25                  30

Val Glu Thr Leu Ile Val Glu Ala Pro Asp His Gly His Glu Thr Thr
        35                  40                  45

Ser Glu Ala Phe Ser Tyr Tyr Leu Trp Leu Glu Ala Met Tyr Gly Arg
    50                  55                  60

Val Thr Gly Asp Trp Ser Pro Phe Asn Asn Ala Trp Asp Thr Met Glu
65                  70                  75                  80

Lys Tyr Ile Ile Pro Ser His Ala Asp Gln Pro Thr Asn Ser Ser Tyr
                85                  90                  95

Asn Pro Ser Lys Pro Ala Thr Tyr Ala Pro Glu His Pro Asp Pro Ser
            100                 105                 110

Gln Tyr Pro Ser Gln Leu Asp Ser Val Pro Val Gly Gln Asp Pro
            115                 120                 125

Ile Ala Asn Glu Leu Lys Ser Thr Tyr Gly Thr Asn Asp Ile Tyr Gly
130                 135                 140

Met His Trp Leu Leu Asp Val Asp Asn Val Tyr Gly Phe Gly Asn Ser
145                 150                 155                 160

Pro Gly Arg Cys Glu Asp Gly Asp Ser Thr Thr Arg Pro Ala Tyr Ile
                165                 170                 175

Asn Thr Phe Gln Arg Gly Pro Gln Glu Ser Val Trp Glu Thr Val Pro
            180                 185                 190

Gln Pro Ser Cys Asp Thr Phe Lys Tyr Gly Gly Pro Asn Gly Tyr Leu
        195                 200                 205

Asp Leu Phe Thr Gly Asp Ser Ser Tyr Pro Ala Lys Gln Trp Lys Tyr
    210                 215                 220

Thr Asn Ala Pro Asp Ala Asp Ala Arg Ala Val Gln Ala Ala Tyr Trp
225                 230                 235                 240

Ala His Glu Trp Ala Lys Glu Gln Gly Lys Ala Ser Glu Val Ala Ala
                245                 250                 255

Thr Val Ala Lys Ala Ala Lys Met Gly Asp Tyr Leu Arg Tyr Ser Met
            260                 265                 270

Phe Asp Lys Tyr Phe Lys Lys Ile Gly Asn Cys Val Gly Ala Ser Ser
        275                 280                 285

Cys Pro Ala Gly Thr Gly Lys Asp Ser Ala His Tyr Leu Leu Ser Trp
290                 295                 300

Tyr Tyr Ala Trp Gly Gly Ala Thr Asp Thr Ser Ala Gly Trp Ala Trp
305                 310                 315                 320

Arg Ile Gly Ser Ser His Ser His Phe Gly Tyr Gln Asn Pro Met Ala
                325                 330                 335

-continued

```
Ala Trp Ala Leu Ser Asn Val Ala Glu Leu Lys Pro Lys Ser Pro Thr
            340                 345                 350

Gly Ala Ser Asp Trp Ala Thr Ser Leu Lys Arg Gln Leu Glu Phe Tyr
        355                 360                 365

Gln Trp Leu Gln Ser Ser Glu Gly Ile Ala Gly Ala Thr Asn
370                 375                 380

Ser Trp Asn Gly Ser Tyr Ala Thr Pro Pro Ala Gly Thr Pro Thr Phe
385                 390                 395                 400

Tyr Gly Met Ser Tyr Asp Glu Gln Pro Val Tyr His Asp Pro Pro Ser
                405                 410                 415

Asn Gln Trp Phe Gly Met Gln Ala Trp Ser Met Glu Arg Val Ala Glu
            420                 425                 430

Tyr Tyr Tyr Ala Thr Gly Asp Ala Arg Ala Lys Ala Val Leu Asp Lys
        435                 440                 445

Trp Val Pro Trp Ala Ile Ala Asn Thr Thr Ile Asn Ala Asp Gly Ser
450                 455                 460

Phe Gln Ile Pro Ser Asp Leu Glu Trp Ser Gly Gln Pro Asp Thr Trp
465                 470                 475                 480

Asn Ala Ser Ser Pro Gly Ala Asn Thr Asn Leu His Val Thr Val Thr
                485                 490                 495

Asn Tyr Gly Gln Asp Val Gly Val Ala Gly Ser Leu Ala Lys Thr Leu
            500                 505                 510

Thr Tyr Tyr Ala Ala Lys Ser Gly Asn Thr Thr Ala Lys Asp Thr Ala
        515                 520                 525

Lys Gly Leu Leu Asp Ala Leu Asn Asn Tyr Gln Asp Ser Lys Gly Ile
    530                 535                 540

Ser Val Pro Glu Thr Arg Ala Asp Tyr Asn Arg Phe Asp Asp Gly Val
545                 550                 555                 560

Tyr Val Pro Pro Gly Trp Thr Gly Thr Met Pro Asn Gly Asp Val Ile
                565                 570                 575

Lys Ser Gly Ala Thr Phe Leu Asp Ile Arg Ser Phe Tyr Lys Asn Asp
            580                 585                 590

Pro Asp Trp Pro Lys Val Glu Ala Tyr Leu Asn Gly Gly Pro Ala Pro
        595                 600                 605

Thr Phe Thr Tyr His Arg Phe Trp Ala Gln Val Asp Ile Ala Thr Ala
    610                 615                 620

Tyr Ala
625

<210> SEQ ID NO 3
<211> LENGTH: 626
<212> TYPE: PRT
<213> ORGANISM: Artificial Sequence
<220> FEATURE:
<223> OTHER INFORMATION: Ancestral exoglucanase catalytic domain

<400> SEQUENCE: 3

Asp Asn Ala Tyr Asp Gln Arg Phe Leu Thr Met Tyr Asn Lys Ile Lys
1               5                   10                  15

Asp Pro Ala Asn Gly Tyr Phe Ser Pro Glu Gly Val Pro Tyr His Ser
            20                  25                  30

Val Glu Thr Leu Ile Val Glu Ala Pro Asp His Gly His Glu Thr Thr
        35                  40                  45

Ser Glu Ala Phe Ser Tyr Tyr Leu Trp Leu Glu Ala Met Tyr Gly Arg
    50                  55                  60
```

```
Val Thr Gly Asp Trp Ser Pro Phe Asn Asn Ala Trp Asp Thr Met Glu
 65                  70                  75                  80

Lys Tyr Ile Ile Pro Ser His Ala Asp Gln Pro Thr Asn Ser Ser Tyr
                 85                  90                  95

Asn Pro Ser Lys Pro Ala Thr Tyr Ala Pro Glu His Pro Asp Pro Ser
            100                 105                 110

Gln Tyr Pro Ser Gln Leu Asp Ser Ser Val Pro Val Gly Gln Asp Pro
        115                 120                 125

Ile Ala Asn Glu Leu Lys Ser Thr Tyr Gly Thr Asn Asp Ile Tyr Gly
130                 135                 140

Met His Trp Leu Leu Asp Val Asp Asn Val Tyr Gly Phe Gly Asn Ser
145                 150                 155                 160

Pro Gly Arg Cys Glu Asp Gly Asp Ser Thr Thr Arg Pro Ala Tyr Ile
                165                 170                 175

Asn Thr Phe Gln Arg Gly Pro Gln Glu Ser Val Trp Glu Thr Val Pro
            180                 185                 190

Gln Pro Ser Cys Asp Thr Phe Lys Tyr Gly Gly Lys Asn Gly Tyr Leu
        195                 200                 205

Asp Leu Phe Thr Gly Asp Ser Ser Tyr Pro Ala Lys Gln Trp Lys Tyr
210                 215                 220

Thr Asn Ala Pro Asp Ala Asp Ala Arg Ala Val Gln Ala Ala Tyr Trp
225                 230                 235                 240

Ala His Glu Trp Ala Lys Glu Gln Gly Lys Ala Ser Glu Val Ala Ala
                245                 250                 255

Thr Val Ala Lys Ala Ala Lys Met Gly Asp Tyr Leu Arg Tyr Ser Met
            260                 265                 270

Phe Asp Lys Tyr Phe Lys Lys Ile Gly Asn Cys Val Gly Ala Ser Ser
        275                 280                 285

Cys Pro Ala Gly Thr Gly Lys Asp Ser Ala His Tyr Leu Leu Ser Trp
        290                 295                 300

Tyr Tyr Ala Trp Gly Gly Ala Thr Asp Thr Ser Ala Gly Trp Ala Trp
305                 310                 315                 320

Arg Ile Gly Ser Ser His Ser His Ser Gly Tyr Gln Asn Pro Met Ala
                325                 330                 335

Ala Trp Ala Leu Ser Asn Val Ala Glu Leu Lys Pro Lys Ser Pro Thr
            340                 345                 350

Gly Ala Ser Asp Trp Ala Thr Ser Leu Lys Arg Gln Leu Glu Phe Tyr
        355                 360                 365

Gln Trp Leu Gln Ser Ser Glu Gly Gly Ile Ala Gly Gly Ala Thr Asn
370                 375                 380

Ser Trp Asn Gly Ser Tyr Ala Thr Pro Pro Ala Gly Thr Pro Thr Phe
385                 390                 395                 400

Tyr Gly Met Tyr Tyr Asp Glu Gln Pro Val Tyr His Asp Pro Pro Ser
                405                 410                 415

Asn Gln Trp Phe Gly Phe Gln Ala Trp Ser Met Glu Arg Val Ala Glu
            420                 425                 430

Tyr Tyr Tyr Ala Thr Gly Asp Ala Arg Ala Lys Ala Val Leu Asp Lys
        435                 440                 445

Trp Val Pro Trp Ala Ile Ala Asn Thr Thr Ile Asn Ala Asp Gly Ser
450                 455                 460

Phe Gln Ile Pro Ser Asp Leu Glu Trp Ser Gly Gln Pro Asp Thr Trp
465                 470                 475                 480

Asn Ala Ser Ser Pro Gly Ala Asn Thr Asn Leu His Val Thr Val Thr
```

```
                485              490              495
Asn Tyr Ser Gln Asp Val Gly Val Ala Gly Ser Leu Ala Lys Thr Leu
                500              505              510

Thr Tyr Tyr Ala Ala Lys Ser Gly Asn Thr Thr Ala Lys Ala Thr Ala
            515              520              525

Lys Gly Leu Leu Asp Ala Leu Asn Asn Tyr Gln Asp Ser Lys Gly Ile
        530              535              540

Ala Val Pro Glu Thr Arg Ala Asp Tyr Asn Arg Phe Asp Asp Gly Val
545              550              555              560

Tyr Val Pro Pro Gly Trp Thr Gly Thr Met Pro Asn Gly Asp Val Ile
                565              570              575

Asp Ser Gly Ser Thr Phe Leu Ser Ile Arg Ser Phe Tyr Lys Asn Asp
                580              585              590

Pro Asp Trp Pro Lys Val Glu Ala Tyr Leu Asn Gly Gly Pro Ala Pro
            595              600              605

Thr Phe Thr Tyr His Arg Phe Trp Ala Gln Val Asp Ile Ala Thr Ala
        610              615              620

Phe Ala
625

<210> SEQ ID NO 4
<211> LENGTH: 626
<212> TYPE: PRT
<213> ORGANISM: Artificial Sequence
<220> FEATURE:
<223> OTHER INFORMATION: Consensus sequence for variants of the
      ancestral exoglucosidases
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
```

```
<222> LOCATION: (130)..(130)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (198)..(199)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (311)..(312)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
```

```
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (343)..(344)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (393)..(393)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (469)..(470)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (484)..(485)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
```

```
<220> FEATURE:
<221> NAME/KEY: misc_feature
<222> LOCATION: (499)..(499)
<223> OTHER INFORMATION: Xaa can be any naturally occurring amino acid
<220> FEATURE:
<221> NAME/KEY: misc_feature
<222> LOCATION: (511)..(511)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (564)..(564)
<223> OTHER INFORMATION: Xaa can be any naturally occurring amino acid
<220> FEATURE:
<221> NAME/KEY: misc_feature
<222> LOCATION: (577)..(577)
<223> OTHER INFORMATION: Xaa can be any naturally occurring amino acid
<220> FEATURE:
<221> NAME/KEY: misc_feature
<222> LOCATION: (580)..(580)
<223> OTHER INFORMATION: Xaa can be any naturally occurring amino acid
<220> FEATURE:
<221> NAME/KEY: misc_feature
<222> LOCATION: (584)..(584)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (591)..(591)
<223> OTHER INFORMATION: Xaa can be any naturally occurring amino acid
<220> FEATURE:
<221> NAME/KEY: misc_feature
<222> LOCATION: (601)..(601)
<223> OTHER INFORMATION: Xaa can be any naturally occurring amino acid
<220> FEATURE:
<221> NAME/KEY: misc_feature
<222> LOCATION: (603)..(604)
<223> OTHER INFORMATION: Xaa can be any naturally occurring amino acid
<220> FEATURE:
<221> NAME/KEY: misc_feature
<222> LOCATION: (625)..(625)
<223> OTHER INFORMATION: Xaa can be any naturally occurring amino acid

<400> SEQUENCE: 4

Asp Asn Ala Tyr Xaa Gln Arg Phe Leu Xaa Met Tyr Asn Lys Ile Lys
1               5                   10                  15

Asp Pro Ala Asn Gly Tyr Phe Ser Pro Glu Gly Xaa Pro Tyr His Ser
            20                  25                  30

Val Glu Thr Leu Ile Val Glu Ala Pro Asp Xaa Gly His Glu Thr Thr
        35                  40                  45

Ser Glu Ala Phe Ser Tyr Tyr Leu Trp Leu Glu Ala Met Tyr Gly Arg
    50                  55                  60
```

```
Xaa Thr Gly Asp Trp Ser Xaa Phe Asn Asn Ala Trp Asp Thr Met Glu
 65                  70                  75                  80

Lys Tyr Ile Ile Pro Ser His Ala Asp Gln Pro Thr Xaa Ser Ser Tyr
                 85                  90                  95

Asn Pro Xaa Lys Pro Ala Thr Tyr Ala Pro Glu His Pro Asp Pro Ser
            100                 105                 110

Gln Tyr Pro Ser Gln Leu Asp Ser Ser Xaa Pro Val Gly Xaa Asp Pro
            115                 120                 125

Ile Xaa Asn Glu Leu Lys Ser Thr Tyr Gly Thr Asn Xaa Ile Tyr Gly
    130                 135                 140

Met His Trp Leu Leu Asp Val Asp Asn Xaa Tyr Gly Phe Gly Asn Ser
145                 150                 155                 160

Pro Gly Arg Cys Glu Asp Gly Asp Ser Thr Thr Arg Pro Ala Tyr Ile
                165                 170                 175

Asn Thr Phe Gln Arg Gly Xaa Gln Glu Ser Val Trp Glu Thr Xaa Pro
            180                 185                 190

Gln Pro Ser Xaa Asp Xaa Xaa Lys Tyr Gly Gly Xaa Asn Gly Xaa Leu
            195                 200                 205

Asp Leu Phe Thr Gly Asp Ser Xaa Tyr Pro Ala Lys Gln Trp Lys Tyr
    210                 215                 220

Thr Asn Ala Pro Asp Ala Asp Ala Arg Ala Val Gln Ala Xaa Tyr Trp
225                 230                 235                 240

Ala His Glu Trp Ala Lys Glu Gln Gly Xaa Ala Ser Xaa Val Xaa Ala
                245                 250                 255

Xaa Val Ala Lys Ala Xaa Lys Met Gly Asp Tyr Leu Arg Tyr Ser Met
            260                 265                 270

Phe Asp Lys Tyr Phe Xaa Lys Ile Gly Asn Cys Val Gly Ala Ser Ser
            275                 280                 285

Xaa Pro Ala Gly Thr Gly Lys Asp Ser Ala His Tyr Leu Leu Ser Trp
    290                 295                 300

Tyr Tyr Ala Trp Gly Gly Xaa Xaa Asp Thr Ser Ala Xaa Trp Ala Trp
305                 310                 315                 320

Arg Ile Gly Ser Ser His Ser His Xaa Gly Tyr Gln Asn Pro Met Ala
                325                 330                 335

Ala Trp Ala Leu Ser Asn Xaa Xaa Glu Leu Lys Pro Lys Ser Pro Thr
            340                 345                 350

Gly Ala Ser Asp Trp Ala Xaa Ser Leu Lys Arg Gln Leu Glu Phe Tyr
            355                 360                 365

Gln Trp Leu Gln Ser Ser Glu Gly Xaa Ile Ala Gly Gly Ala Thr Asn
    370                 375                 380

Ser Trp Asn Gly Ser Tyr Ala Thr Xaa Pro Ala Gly Thr Xaa Thr Phe
385                 390                 395                 400

Tyr Gly Met Xaa Tyr Asp Glu Gln Pro Val Tyr His Asp Pro Pro Ser
            405                 410                 415

Asn Gln Trp Phe Gly Xaa Gln Ala Trp Ser Met Glu Arg Val Ala Glu
            420                 425                 430

Tyr Tyr Tyr Xaa Thr Gly Asp Xaa Arg Ala Lys Xaa Val Leu Asp Lys
            435                 440                 445

Trp Val Xaa Trp Ala Xaa Ala Asn Xaa Thr Ile Asn Ala Asp Gly Xaa
    450                 455                 460

Phe Gln Ile Pro Xaa Xaa Leu Glu Trp Ser Gly Gln Pro Asp Thr Trp
465                 470                 475                 480

Xaa Ala Ser Xaa Xaa Gly Ala Asn Xaa Asn Leu His Val Thr Val Xaa
```

```
                    485                 490                 495
Asn Tyr Xaa Gln Asp Val Gly Val Ala Gly Ser Leu Ala Lys Xaa Leu
            500                 505                 510

Thr Tyr Tyr Ala Ala Lys Ser Gly Asn Thr Thr Ala Lys Xaa Thr Ala
        515                 520                 525

Lys Xaa Leu Leu Asp Ala Leu Asn Asn Tyr Gln Asp Ser Lys Gly Ile
    530                 535                 540

Xaa Val Pro Glu Thr Arg Ala Asp Tyr Asn Arg Phe Xaa Asp Xaa Val
545                 550                 555                 560

Tyr Val Pro Xaa Gly Trp Thr Gly Thr Met Pro Asn Gly Asp Val Ile
                565                 570                 575

Xaa Ser Gly Xaa Thr Phe Leu Xaa Ile Arg Ser Xaa Tyr Lys Xaa Asp
                580                 585                 590

Pro Asp Trp Pro Lys Val Glu Ala Xaa Leu Xaa Xaa Gly Pro Ala Pro
        595                 600                 605

Thr Phe Thr Tyr His Arg Phe Trp Ala Gln Val Asp Ile Ala Thr Ala
        610                 615                 620

Xaa Ala
625

<210> SEQ ID NO 5
<211> LENGTH: 104
<212> TYPE: PRT
<213> ORGANISM: Artificial Sequence
<220> FEATURE:
<223> OTHER INFORMATION: Carbohydrate binding domain

<400> SEQUENCE: 5

Ala Cys Ser Val Asp Tyr Lys Thr Asn Asp Trp Gly Ser Gly Phe Thr
1               5                   10                  15

Ala Glu Val Thr Ile Thr Asn Arg Gly Thr Asp Pro Ile Asp G

```
Arg Lys Gln Ala Ala Gly Ala Asp His Leu Gly Leu Asn Glu Ser Val
 50                  55                  60

Pro Ala Thr Cys Phe Pro Thr Ala Ala Leu Ala Ser Ser Trp Asp
 65                  70                  75                  80

Pro Glu Leu Leu His Glu Val Gly Ala Leu Gly Glu Glu Cys Arg
                     85                  90                  95

Ala Glu Asn Val Ser Val Leu Leu Gly Pro Gly Val Asn Ile Lys Arg
                100                 105                 110

Ser Pro Leu Cys Gly Arg Asn Phe Glu Tyr Phe Ser Glu Asp Pro Tyr
                115                 120                 125

Leu Ala Gly Glu Met Ala Ala Ala Trp Ile Ser Gly Val Gln Ser Lys
130                 135                 140

Gly Val Gly Thr Ser Leu Lys His Phe Ala Ala Asn Asn Gln Glu His
145                 150                 155                 160

Arg Arg Met Thr Val Asp Ala Val Val Asp Glu Arg Thr Leu Arg Glu
                165                 170                 175

Ile Tyr Leu Ala Ala Phe Glu His Ala Val Lys Gln Ala Gln Pro Trp
                180                 185                 190

Thr Val Met Cys Ser Tyr Asn Arg Ile Asn Gly Val Tyr Ser Ser Glu
                195                 200                 205

Asn Arg Trp Leu Leu Thr Glu Val Leu Arg Asp Glu Trp Gly Phe Glu
                210                 215                 220

Gly Leu Val Val Ser Asp Trp Gly Ala Val Asn Asp Arg Val Lys Ala
225                 230                 235                 240

Leu Lys Ala Gly Leu Asp Leu Glu Met Pro Ser Ser Gly Gly Leu Asn
                245                 250                 255

Asp Lys Gln Ile Val Glu Ala Val Arg Ser Gly Glu Leu Asp Glu Ala
                260                 265                 270

Val Leu Asp Arg Ala Ala Glu Arg Val Leu Thr Leu Ile Ala Arg Thr
                275                 280                 285

Ala Ala Ala Arg Thr Glu Asn His Ser Tyr Asp Val Glu Ala His His
                290                 295                 300

Ala Leu Ala Arg Arg Ala Ala Ala Glu Ser Ala Val Leu Leu Lys Asn
305                 310                 315                 320

Asp Asp Gly Ile Leu Pro Leu Thr Ala Glu Ala Lys Ile Ala Val Ile
                325                 330                 335

Gly Glu Phe Ala Lys Thr Pro Arg Tyr Gln Gly Ala Gly Ser Ser Gln
                340                 345                 350

Ile Asn Pro Thr Lys Leu Asp Asn Ala Leu Asp Glu Leu Arg Glu Arg
                355                 360                 365

Gly Gly Asp Asp Val Thr Tyr Ala Pro Gly Tyr Glu Leu Asp Gly Asp
                370                 375                 380

Arg Thr Asp Ala Ala Leu Leu Glu Glu Ala Val Glu Val Ala Lys Asn
385                 390                 395                 400

Ala Asp Val Val Val Phe Ala Gly Leu Pro Asp Ser Tyr Glu Ser
                405                 410                 415

Glu Gly Phe Asp Arg Thr His Leu Asn Leu Pro Glu Asn His Asn Ala
                420                 425                 430

Leu Ile Glu Ala Val Ala Glu Val Asn Pro Asn Val Val Val Val Leu
                435                 440                 445

Ser Asn Gly Ser Pro Val Thr Met Pro Trp Arg Asp Arg Val Lys Ala
450                 455                 460

Ile Leu Glu Ser Tyr Leu Gly Gly Gln Ala Gly Gly Ser Ala Ile Ala
```

```
            465                 470                 475                 480
        Asp Ile Leu Thr Gly Glu Val Asn Pro Ser Gly Arg Leu Ala Glu Thr
                            485                 490                 495

Phe Pro Leu Arg Leu Glu Asp Asn Pro Ser Tyr Leu Asn Phe Pro Gly
                        500                 505                 510

Glu Pro Gln His Val Glu Tyr Arg Glu Ser Ile Phe Val Gly Tyr Arg
                    515                 520                 525

Tyr Tyr Asp Thr Ala Glu Arg Asp Val Ala Tyr Pro Phe Gly Tyr Gly
                530                 535                 540

Leu Ser Tyr Thr Thr Phe Glu Tyr Ser Asp Leu Lys Val Ser Lys Ala
        545                 550                 555                 560

Ala Asp Asp Asn Glu Thr Val Glu Val Ser Val Thr Val Thr Asn Thr
                        565                 570                 575

Gly Asp Arg Ala Gly Ser Glu Val Val Gln Val Tyr Val Gly Asp Ala
                    580                 585                 590

Glu Ser Thr Val Phe Arg Pro Val Gln Glu Leu Lys Gly Phe Ala Lys
                595                 600                 605

Val Phe Leu Glu Pro Gly Glu Ser Arg Glu Val Thr Ile Asp Leu Asp
            610                 615                 620

Arg Arg Ala Phe Ser Tyr Trp Asn Val Lys Ile Asn Asp Trp Thr Val
        625                 630                 635                 640

Glu Ser Gly Asp Phe Glu Ile Arg Val Gly Ser Ser Arg Asp Ile
                        645                 650                 655

Arg Leu Thr Ala Thr Val Thr Leu Asn Ser Asn Thr Pro Leu Pro Gln
                    660                 665                 670

Thr Phe Thr Val Asn Thr Thr Ile Gly Asp Ile Met Ala His Pro Ala
                675                 680                 685

Gly Arg Ala Leu Leu Gly Ala Leu Val Gln Ala Val Ala Ala Gly Ser
            690                 695                 700

Ala Ala Lys Asp Ser Val Ser Arg Met Met Met Ala Met Leu Gln Asp
        705                 710                 715                 720

Met Pro Leu Arg Ser Leu Pro Met Phe Thr Gly Gly Ala Ile Thr Pro
                        725                 730                 735

Glu Met Leu Glu Glu Leu Val Glu Met Leu Asn Gly
                    740                 745

<210> SEQ ID NO 7
<211> LENGTH: 748
<212> TYPE: PRT
<213> ORGANISM: Artificial Sequence
<220> FEATURE:
<223> OTHER INFORMATION: Ancestral beta glucosidase

<400> SEQUENCE: 7

Thr Asp Asn Ile Lys Glu Leu Val Asn Gln Met Thr Leu Glu Glu Lys
1               5                   10                  15

Ala Ser Leu Cys Ser Gly Lys Asp Phe Trp His Thr Gln Ser Ile Glu
                20                  25                  30

Arg Leu Gly Ile Pro Ser Ile Met Val Thr Asp Gly Pro His Gly Leu
            35                  40                  45

Arg Lys Gln Ala Ala Glu Ala Asp His Leu Gly Leu Asn Glu Ser Val
        50                  55                  60

Pro Ala Thr Cys Phe Pro Thr Ala Ala Leu Ala Ser Ser Trp Asp
65                  70                  75                  80

Pro Glu Leu Leu His Glu Val Gly Glu Ala Leu Gly Glu Glu Cys Arg
```

```
            85                  90                  95
Ala Glu Asn Val Ser Val Leu Leu Gly Pro Gly Val Asn Ile Lys Arg
            100                 105                 110

Ser Pro Leu Cys Gly Arg Asn Phe Glu Tyr Phe Ser Glu Asp Pro Tyr
            115                 120                 125

Leu Ala Gly Glu Met Ala Ala Trp Ile Ser Gly Val Gln Ser Lys
            130                 135                 140

Gly Val Gly Thr Ser Leu Lys His Phe Ala Ala Asn Asn Gln Glu His
145                 150                 155                 160

Arg Arg Met Thr Val Asp Ala Val Asp Glu Arg Thr Leu Arg Glu
                    165                 170                 175

Ile Tyr Leu Ala Ala Phe Glu Asn Ala Val Lys Gln Ala Gln Pro Trp
                    180                 185                 190

Thr Val Met Cys Ser Tyr Asn Arg Ile Asn Gly Val Tyr Ser Ser Glu
                    195                 200                 205

Asn Lys Trp Leu Leu Thr Glu Val Leu Arg Asp Glu Trp Gly Phe Glu
            210                 215                 220

Gly Leu Val Val Ser Asp Trp Gly Ala Val Asn Asp Arg Val Lys Gly
225                 230                 235                 240

Leu Lys Ala Gly Leu Asp Leu Glu Met Pro Ser Ser Gly Gly Leu Asn
                    245                 250                 255

Asp Lys Gln Ile Val Glu Ala Val Arg Asn Gly Glu Leu Asp Glu Ala
                    260                 265                 270

Val Leu Asp Arg Ala Ala Glu Arg Ile Leu Thr Leu Ile Ala Arg Ala
                    275                 280                 285

Ala Ala Ala Arg Lys Gln Asn His Thr Tyr Asp Val Glu Ala His His
            290                 295                 300

Ala Leu Ala Arg Arg Ile Ala Ala Glu Ser Ala Val Leu Leu Lys Asn
305                 310                 315                 320

Asp Asp Gly Ile Leu Pro Leu Lys Lys Glu Ala Lys Ile Ala Val Ile
                    325                 330                 335

Gly Glu Phe Ala Lys Thr Pro Arg Tyr Gln Gly Ala Gly Ser Ser Gln
                    340                 345                 350

Ile Asn Pro Thr Lys Leu Asp Asn Ala Leu Asp Glu Leu Arg Glu Arg
            355                 360                 365

Gly Gly Ala Asp Val Thr Tyr Ala Pro Gly Tyr Glu Leu Asp Gly Asp
            370                 375                 380

Arg Thr Asp Ala Ala Leu Leu Glu Glu Ala Val Glu Val Ala Lys Asn
385                 390                 395                 400

Ala Asp Val Val Val Phe Ala Gly Leu Pro Asp Ser Tyr Glu Ser
                    405                 410                 415

Glu Gly Phe Asp Arg Thr His Leu Asn Leu Pro Glu Asn His Asn Ala
                    420                 425                 430

Leu Ile Glu Ala Val Ala Glu Val Asn Pro Asn Val Val Val Leu
                    435                 440                 445

Ser Asn Gly Ser Pro Val Thr Met Pro Trp Arg Asp Lys Val Lys Ala
            450                 455                 460

Ile Leu Glu Ser Tyr Leu Gly Gly Gln Ala Gly Gly Ser Ala Ile Ala
465                 470                 475                 480

Asp Ile Leu Thr Gly Glu Val Asn Pro Ser Gly Arg Leu Ala Glu Thr
                    485                 490                 495

Phe Pro Leu Arg Leu Glu Asp Asn Pro Ser Tyr Leu Asn Phe Pro Gly
                    500                 505                 510
```

Glu Pro Gln His Val Glu Tyr Arg Glu Ser Ile Phe Val Gly Tyr Arg
                515                 520                 525

Tyr Tyr Asp Thr Ala Glu Lys Asp Val Ala Phe Pro Phe Gly Tyr Gly
    530                 535                 540

Leu Ser Tyr Thr Thr Phe Glu Tyr Ser Asp Leu Lys Ile Ser Lys Ala
545                 550                 555                 560

Ala Asp Asp Asn Glu Thr Val Glu Val Ser Val Thr Val Thr Asn Thr
                565                 570                 575

Gly Asp Arg Ala Gly Ser Glu Val Val Gln Val Tyr Val Gly Asp Ala
                580                 585                 590

Glu Ser Thr Val Phe Arg Pro Val Gln Glu Leu Lys Gly Phe Ala Lys
            595                 600                 605

Val Phe Leu Glu Pro Gly Glu Ser Arg Glu Val Thr Ile Thr Leu Asp
            610                 615                 620

Arg Arg Ala Phe Ser Tyr Tyr Asn Val Lys Ile Asn Asp Trp Thr Val
625                 630                 635                 640

Glu Ser Gly Asp Phe Glu Ile Arg Val Gly Ser Ser Arg Asp Ile
                645                 650                 655

Arg Leu Lys Ala Thr Val Thr Leu Asn Ser Thr Thr Pro Leu Pro Ala
                660                 665                 670

Thr Phe Thr Val Asn Thr Thr Ile Gly Asp Ile Met Ala Ser Pro Ala
                675                 680                 685

Gly Lys Ala Leu Leu Gly Ala Leu Val Gln Ala Val Ser Ala Gly Ser
            690                 695                 700

Gly Ala Lys Asp Ser Val Ser Arg Met Met Met Ala Met Leu Gln Asp
705                 710                 715                 720

Met Pro Leu Arg Ser Leu Ala Met Phe Thr Gly Gly Ala Ile Thr Pro
                725                 730                 735

Glu Met Leu Glu Glu Leu Val Glu Met Leu Asn Gly
            740                 745

<210> SEQ ID NO 8
<211> LENGTH: 748
<212> TYPE: PRT
<213> ORGANISM: Artificial Sequence
<220> FEATURE:
<223> OTHER INFORMATION: Ancestral beta glucosidase

<400> SEQUENCE: 8

Met Met Asn Ile Lys Glu Ile Ile Asn Gln Met Thr Leu Glu Glu Lys
1               5                   10                  15

Ala Ser Leu Cys Ser Gly Lys Asp Phe Trp His Thr Lys Ser Ile Glu
                20                  25                  30

Arg Leu Gly Ile Pro Ser Ile Met Met Thr Asp Gly Pro His Gly Leu
            35                  40                  45

Arg Lys Gln Lys Ala Asp Ala Asp His Leu Gly Leu Asn Glu Ser Val
        50                  55                  60

Pro Ala Thr Cys Phe Pro Thr Ala Ala Leu Ala Ser Ser Trp Asp
65                  70                  75                  80

Pro Asp Leu Leu Glu Glu Val Gly Lys Ala Leu Gly Glu Glu Cys Gln
                85                  90                  95

Ala Glu Asn Val Ser Val Leu Leu Gly Pro Gly Val Asn Ile Lys Arg
                100                 105                 110

Ser Pro Leu Cys Gly Arg Asn Phe Glu Tyr Phe Ser Glu Asp Pro Tyr
            115                 120                 125

```
Leu Ala Gly Glu Met Ala Ala Ser Trp Ile Lys Gly Val Gln Ser Gln
            130                 135                 140

Gly Val Gly Thr Ser Leu Lys His Phe Ala Ala Asn Asn Gln Glu His
145                 150                 155                 160

Arg Arg Met Thr Val Asp Ala Val Val Asp Glu Arg Thr Leu Arg Glu
                    165                 170                 175

Ile Tyr Leu Ala Ala Phe Glu Asn Ala Val Lys Gln Ala Gln Pro Trp
                180                 185                 190

Thr Val Met Cys Ser Tyr Asn Lys Ile Asn Gly Val Tyr Ala Ser Glu
            195                 200                 205

Asn Lys Arg Leu Leu Thr Glu Ile Leu Arg Asp Glu Trp Gly Phe Glu
210                 215                 220

Gly Leu Val Val Ser Asp Trp Gly Ala Val Asn Asp Arg Val Lys Gly
225                 230                 235                 240

Leu Lys Ala Gly Leu Asp Leu Glu Met Pro Ser Ser Gly Gly Ile Asn
                245                 250                 255

Asp Lys Gln Ile Val Glu Ala Val Lys Asn Gly Glu Leu Asp Glu Ala
                260                 265                 270

Val Leu Asp Arg Ala Val Glu Arg Ile Leu Asn Leu Ile Phe Lys Ala
            275                 280                 285

Ala Ala Ala Arg Lys Gln Asn His Thr Tyr Asp Val Glu Ala His His
290                 295                 300

Ala Leu Ala Arg Lys Ile Ala Ala Glu Ser Met Val Leu Leu Lys Asn
305                 310                 315                 320

Asp Asp Gly Ile Leu Pro Leu Lys Lys Glu Ala Lys Ile Ala Val Ile
                325                 330                 335

Gly Glu Phe Ala Lys Thr Pro Arg Tyr Gln Gly Ala Gly Ser Ser His
                340                 345                 350

Ile Asn Pro Thr Lys Leu Asp Asn Ala Leu Asp Glu Leu Lys Glu Leu
            355                 360                 365

Gly Gly Ala Asp Val Thr Tyr Ala Gln Gly Tyr Glu Leu Asp Gly Asp
370                 375                 380

Arg Thr Asp Ala Ala Leu Ile Glu Glu Ala Val Glu Leu Ala Lys Asn
385                 390                 395                 400

Ala Asp Val Val Val Ile Phe Ala Gly Leu Pro Asp Ser Tyr Glu Ser
                405                 410                 415

Glu Gly Phe Asp Arg Thr His Met Asn Met Pro Glu Asn His Asn Glu
                420                 425                 430

Leu Ile Glu Ala Val Ala Lys Val Asn Pro Asn Val Val Val Val Leu
            435                 440                 445

Ser Asn Gly Ser Pro Val Glu Met Pro Trp Ile Asp Lys Val Lys Gly
450                 455                 460

Ile Leu Glu Ser Tyr Leu Gly Gly Gln Ala Gly Gly Ser Ala Ile Ala
465                 470                 475                 480

Asp Ile Leu Thr Gly Glu Val Asn Pro Ser Gly Lys Leu Ala Glu Thr
                485                 490                 495

Phe Pro Leu Arg Leu Glu Asp Asn Pro Ser Tyr Leu Asn Phe Pro Gly
                500                 505                 510

Glu Pro Asp Arg Val Glu Tyr Arg Glu Ser Ile Phe Val Gly Tyr Arg
            515                 520                 525

Tyr Tyr Asp Thr Ala Asn Lys Asp Val Leu Phe Pro Phe Gly Tyr Gly
530                 535                 540
```

```
Leu Ser Tyr Thr Thr Phe Glu Tyr Ser Asp Leu Lys Ile Ser Lys Glu
545                 550                 555                 560

Ile Asn Asp Thr Glu Thr Val Glu Val Ser Val Lys Val Lys Asn Thr
            565                 570                 575

Gly Asp Val Ala Gly Ser Glu Val Val Gln Val Tyr Val Ser Asp Lys
        580                 585                 590

Glu Ser Thr Val Phe Arg Pro Val Lys Glu Leu Lys Gly Phe Glu Lys
    595                 600                 605

Val Phe Leu Glu Pro Gly Glu Ser Lys Glu Val Thr Ile Thr Leu Asp
610                 615                 620

Lys Arg Ala Phe Ala Tyr Tyr Asn Val Lys Ile Asn Asp Trp His Val
625                 630                 635                 640

Glu Ser Gly Glu Phe Glu Ile Leu Val Gly Ser Ser Arg Asp Ile
            645                 650                 655

Arg Leu Lys Ala Thr Val Thr Val Asn Ser Thr Thr Pro Leu Pro Ala
        660                 665                 670

Thr Phe Thr Val Asn Thr Ile Gly Asp Val Met Ser Thr Pro Ala
    675                 680                 685

Gly Lys Ala Leu Leu Asn Ala Leu Ile Gln Lys Val Ser Val Gly Ser
690                 695                 700

Gly Ala Lys Asp Ser Glu Ser Asp Met Met Met Ala Met Val Gln Asp
705                 710                 715                 720

Met Pro Leu Arg Ser Leu Val Thr Phe Thr Gly Gly Ala Ile Thr Ala
            725                 730                 735

Glu Met Leu Glu Glu Leu Ile Glu Met Leu Asn Gly
        740                 745
```

<210> SEQ ID NO 9
<211> LENGTH: 44
<212> TYPE: PRT
<213> ORGANISM: Artificial Sequence
<220> FEATURE:
<223> OTHER INFORMATION: Linking domain

<400> SEQUENCE: 9

```
Pro Arg Phe Val Lys Pro Val Glu Tyr Val Leu Pro Gln Pro Asp Val
1               5                   10                  15

Arg Val Asn Gln Val Gly Tyr Leu Pro Phe Ala Lys Lys Tyr Ala Thr
            20                  25                  30

Val Val Ser Ser Ser Thr Ser Pro Leu Lys Arg Ser
        35                  40
```

<210> SEQ ID NO 10
<211> LENGTH: 748
<212> TYPE: PRT
<213> ORGANISM: Artificial Sequence
<220> FEATURE:
<223> OTHER INFORMATION: Consensus sequence of the ancestral beta
      glucosidases
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:

```
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (42)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (265)..(266)
<223> OTHER INFORMATION: Xaa can be any naturally occurring amino acid
```

```
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (286)..(288)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (309)..(310)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (328)..(329)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (406)..(406)
<223> OTHER INFORMATION: Xaa can be any naturally occurring amino acid
<220> FEATURE:
<221> NAME/KEY: misc_feature
<222> LOCATION: (424)..(424)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (432)..(432)
```

```
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (515)..(516)
<223> OTHER INFORMATION: Xaa can be any naturally occurring amino acid
<220> FEATURE:
<221> NAME/KEY: misc_feature
<222> LOCATION: (534)..(535)
<223> OTHER INFORMATION: Xaa can be any naturally occurring amino acid
<220> FEATURE:
<221> NAME/KEY: misc_feature
<222> LOCATION: (538)..(539)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (560)..(562)
<223> OTHER INFORMATION: Xaa can be any naturally occurring amino acid
<220> FEATURE:
<221> NAME/KEY: misc_feature
<222> LOCATION: (564)..(564)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (574)..(574)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (601)..(601)
<223> OTHER INFORMATION: Xaa can be any naturally occurring amino acid
<220> FEATURE:
<221> NAME/KEY: misc_feature
<222> LOCATION: (607)..(607)
<223> OTHER INFORMATION: Xaa can be any naturally occurring amino acid
<220> FEATURE:
<221> NAME/KEY: misc_feature
```

```
<222> LOCATION: (617)..(617)
<223> OTHER INFORMATION: Xaa can be any naturally occurring amino acid
<220> FEATURE:
<221> NAME/KEY: misc_feature
<222> LOCATION: (622)..(622)
<223> OTHER INFORMATION: Xaa can be any naturally occurring amino acid
<220> FEATURE:
<221> NAME/KEY: misc_feature
<222> LOCATION: (625)..(625)
<223> OTHER INFORMATION: Xaa can be any naturally occurring amino acid
<220> FEATURE:
<221> NAME/KEY: misc_feature
<222> LOCATION: (629)..(629)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (639)..(639)
<223> OTHER INFORMATION: Xaa can be any naturally occurring amino acid
<220> FEATURE:
<221> NAME/KEY: misc_feature
<222> LOCATION: (644)..(644)
<223> OTHER INFORMATION: Xaa can be any naturally occurring amino acid
<220> FEATURE:
<221> NAME/KEY: misc_feature
<222> LOCATION: (648)..(648)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (664)..(664)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (683)..(683)
<223> OTHER INFORMATION: Xaa can be any naturally occurring amino acid
<220> FEATURE:
<221> NAME/KEY: misc_feature
<222> LOCATION: (685)..(686)
<223> OTHER INFORMATION: Xaa can be any naturally occurring amino acid
<220> FEATURE:
<221> NAME/KEY: misc_feature
<222> LOCATION: (694)..(694)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (699)..(699)
<223> OTHER INFORMATION: Xaa can be any naturally occurring amino acid
<220> FEATURE:
<221> NAME/KEY: misc_feature
<222> LOCATION: (701)..(702)
<223> OTHER INFORMATION: Xaa can be any naturally occurring amino acid
<220> FEATURE:
<221> NAME/KEY: misc_feature
<222> LOCATION: (705)..(705)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
```

<221> NAME/KEY: misc_feature
<222> LOCATION: (712)..(712)
<223> OTHER INFORMATION: Xaa can be any naturally occurring amino acid
<220> FEATURE:
<221> NAME/KEY: misc_feature
<222> LOCATION: (718)..(718)
<223> OTHER INFORMATION: Xaa can be any naturally occurring amino acid
<220> FEATURE:
<221> NAME/KEY: misc_feature
<222> LOCATION: (727)..(728)
<223> OTHER INFORMATION: Xaa can be any naturally occurring amino acid
<220> FEATURE:
<221> NAME/KEY: misc_feature
<222> LOCATION: (736)..(736)
<223> OTHER INFORMATION: Xaa can be any naturally occurring amino acid
<220> FEATURE:
<221> NAME/KEY: misc_feature
<222> LOCATION: (743)..(743)
<223> OTHER INFORMATION: Xaa can be any naturally occurring amino acid

<400> SEQUENCE: 10

Xaa Xaa Asn Ile Lys Glu Xaa Xaa Asn Xaa Met Thr Leu Glu Glu Lys
1               5                   10                  15

Ala Ser Leu Cys Ser Gly Xaa Asp Phe Trp His Thr Xaa Ser Ile Glu
            20                  25                  30

Arg Leu Gly Ile Pro Ser Ile Met Val Xaa Xaa Xaa Xaa Xaa Xaa Xaa
        35                  40                  45

Xaa Xaa Gln Xaa Ala Xaa Ala Asp His Leu Gly Leu Asn Glu Ser Val
50                  55                  60

Pro Ala Thr Cys Phe Pro Thr Ala Ala Leu Ala Ser Ser Trp Asp
65                  70                  75                  80

Pro Xaa Leu Leu Xaa Glu Val Gly Xaa Ala Leu Gly Glu Glu Cys Xaa
                85                  90                  95

Ala Glu Asn Val Ser Val Leu Leu Gly Pro Gly Val Asn Ile Lys Arg
            100                 105                 110

Ser Pro Leu Cys Gly Arg Asn Phe Glu Tyr Phe Ser Glu Asp Pro Tyr
        115                 120                 125

Leu Ala Gly Glu Met Ala Ala Xaa Trp Ile Xaa Gly Val Gln Ser Xaa
130                 135                 140

Gly Val Gly Thr Ser Leu Lys His Phe Ala Ala Asn Asn Gln Glu His
145                 150                 155                 160

Arg Arg Met Thr Val Asp Ala Val Val Asp Glu Arg Thr Leu Arg Glu
                165                 170                 175

Ile Tyr Leu Ala Ala Phe Glu Xaa Ala Val Lys Gln Ala Gln Pro Trp
            180                 185                 190

Thr Val Met Cys Ser Tyr Asn Xaa Ile Asn Gly Val Tyr Xaa Ser Glu
        195                 200                 205

Asn Xaa Xaa Leu Leu Thr Glu Xaa Leu Arg Asp Glu Trp Gly Phe Glu
210                 215                 220

Gly Leu Val Val Ser Asp Trp Gly Ala Val Asn Asp Arg Val Lys Xaa
225                 230                 235                 240

Leu Lys Ala Gly Leu Asp Leu Glu Met Pro Ser Ser Gly Gly Xaa Asn
                245                 250                 255

Asp Lys Gln Ile Val Glu Ala Val Xaa Xaa Gly Glu Leu Asp Glu Ala
            260                 265                 270

Val Leu Asp Arg Ala Xaa Glu Arg Xaa Leu Xaa Leu Ile Xaa Xaa Xaa
        275                 280                 285

Ala Ala Ala Arg Xaa Xaa Asn His Xaa Tyr Asp Val Glu Ala His His
290                 295                 300

```
Ala Leu Ala Arg Xaa Xaa Ala Ala Glu Ser Xaa Val Leu Leu Lys Asn
305                 310                 315                 320

Asp Asp Gly Ile Leu Pro Leu Xaa Xaa Glu Ala Lys Ile Ala Val Ile
            325                 330                 335

Gly Glu Phe Ala Lys Thr Pro Arg Tyr Gln Gly Ala Gly Ser Ser Xaa
            340                 345                 350

Ile Asn Pro Thr Lys Leu Asp Asn Ala Leu Asp Glu Leu Xaa Glu Xaa
            355                 360                 365

Gly Gly Xaa Asp Val Thr Tyr Ala Xaa Gly Tyr Glu Leu Asp Gly Asp
        370                 375                 380

Arg Thr Asp Ala Ala Leu Xaa Glu Glu Ala Val Glu Xaa Ala Lys Asn
385                 390                 395                 400

Ala Asp Val Val Val Xaa Phe Ala Gly Leu Pro Asp Ser Tyr Glu Ser
                405                 410                 415

Glu Gly Phe Asp Arg Thr His Xaa Asn Xaa Pro Glu Asn His Asn Xaa
            420                 425                 430

Leu Ile Glu Ala Val Ala Xaa Val Asn Pro Asn Val Val Val Val Leu
            435                 440                 445

Ser Asn Gly Ser Pro Val Xaa Met Pro Trp Xaa Asp Xaa Val Lys Xaa
450                 455                 460

Ile Leu Glu Ser Tyr Leu Gly Gly Gln Ala Gly Ser Ala Ile Ala
465                 470                 475                 480

Asp Ile Leu Thr Gly Glu Val Asn Pro Ser Gly Xaa Leu Ala Glu Thr
                485                 490                 495

Phe Pro Leu Arg Leu Glu Asp Asn Pro Ser Tyr Leu Asn Phe Pro Gly
            500                 505                 510

Glu Pro Xaa Xaa Val Glu Tyr Arg Glu Ser Ile Phe Val Gly Tyr Arg
            515                 520                 525

Tyr Tyr Asp Thr Ala Xaa Xaa Asp Val Xaa Xaa Pro Phe Gly Tyr Gly
        530                 535                 540

Leu Ser Tyr Thr Thr Phe Glu Tyr Ser Asp Leu Lys Xaa Ser Lys Xaa
545                 550                 555                 560

Xaa Xaa Asp Xaa Glu Thr Val Glu Val Ser Val Xaa Val Xaa Asn Thr
                565                 570                 575

Gly Asp Xaa Ala Gly Ser Glu Val Val Gln Val Tyr Val Xaa Asp Xaa
            580                 585                 590

Glu Ser Thr Val Phe Arg Pro Val Xaa Glu Leu Lys Gly Phe Xaa Lys
            595                 600                 605

Val Phe Leu Glu Pro Gly Glu Ser Xaa Glu Val Thr Ile Xaa Leu Asp
610                 615                 620

Xaa Arg Ala Phe Xaa Tyr Xaa Asn Val Lys Ile Asn Asp Trp Xaa Val
625                 630                 635                 640

Glu Ser Gly Xaa Phe Glu Ile Xaa Val Gly Ser Ser Arg Asp Ile
                645                 650                 655

Arg Leu Xaa Ala Thr Val Thr Xaa Asn Ser Xaa Thr Pro Leu Pro Xaa
            660                 665                 670

Thr Phe Thr Val Asn Thr Thr Ile Gly Asp Xaa Met Xaa Xaa Pro Ala
            675                 680                 685

Gly Lys Ala Leu Leu Xaa Ala Leu Xaa Gln Xaa Val Xaa Xaa Gly Ser
            690                 695                 700

Xaa Ala Lys Asp Ser Xaa Ser Xaa Met Met Met Ala Met Xaa Gln Asp
705                 710                 715                 720

Met Pro Leu Arg Ser Leu Xaa Xaa Phe Thr Gly Gly Ala Ile Thr Xaa
```

```
                        725                 730                 735
Glu Met Leu Glu Glu Leu Xaa Glu Met Leu Asn Gly
                    740                 745

<210> SEQ ID NO 11
<211> LENGTH: 297
<212> TYPE: PRT
<213> ORGANISM: Artificial Sequence
<220> FEATURE:
<223> OTHER INFORMATION: Ancestral endocellulase

<400> SEQUENCE: 11

Thr Pro Val Glu Thr His Gly Gln Leu Ser Val Lys Gly Gly Gln Leu
1               5                   10                  15

Val Asp Glu Asn Gly Lys Pro Val Gln Leu Arg Gly Met Ser Ser His
            20                  25                  30

Gly Leu Gln Trp Phe Gly Asp Phe Val Asn Lys Asp Ser Met Lys Trp
        35                  40                  45

Leu Arg Asp Asp Trp Gly Ile Asn Val Phe Arg Val Ala Met Tyr Thr
    50                  55                  60

Ala Glu Gly Gly Tyr Ile Thr Asn Pro Ser Val Lys Asn Lys Val Lys
65                  70                  75                  80

Glu Ala Val Glu Ala Ala Ile Asp Leu Gly Met Tyr Val Ile Ile Asp
                85                  90                  95

Trp His Ile Leu Ser Asp Asn Asp Pro Asn Thr Tyr Lys Glu Gln Ala
            100                 105                 110

Lys Ala Phe Phe Gln Glu Met Ala Ala Lys Tyr Gly Asn Tyr Pro Asn
        115                 120                 125

Val Ile Tyr Glu Ile Cys Asn Glu Pro Asn Gly Gly Val Thr Trp Ser
    130                 135                 140

Asn Gln Ile Lys Pro Tyr Ala Glu Glu Val Ile Pro Ala Ile Arg Ala
145                 150                 155                 160

Asn Asp Pro Asp Asn Ile Ile Ile Val Gly Thr Pro Thr Trp Ser Gln
                165                 170                 175

Asp Val His Asp Ala Ala Asp Asn Pro Leu Pro Tyr Ser Asn Ile Met
            180                 185                 190

Tyr Ala Leu His Phe Tyr Ala Gly Thr His Gly Gln Ser Leu Arg Asp
        195                 200                 205

Lys Ile Asp Tyr Ala Leu Ser Lys Gly Val Ala Ile Phe Val Thr Glu
    210                 215                 220

Trp Gly Thr Ser Asp Ala Ser Gly Asn Gly Gly Pro Phe Leu Asn Glu
225                 230                 235                 240

Ser Gln Lys Trp Ile Asp Phe Met Asn Ser Arg Asn Ile Ser Trp Ala
                245                 250                 255

Asn Trp Ser Leu Ser Asp Lys Ser Glu Thr Ser Ala Ala Leu Met Pro
            260                 265                 270

Gly Ala Ser Pro Thr Gly Gly Trp Thr Asp Ser Asn Leu Ser Ala Ser
        275                 280                 285

Gly Lys Phe Val Arg Glu Gln Ile Arg
    290                 295

<210> SEQ ID NO 12
<211> LENGTH: 297
<212> TYPE: PRT
<213> ORGANISM: Artificial Sequence
<220> FEATURE:
<223> OTHER INFORMATION: Ancestral endocellulase
```

<400> SEQUENCE: 12

```
Thr Pro Val Glu Ile Asn Gly Gln Leu Gln Val Cys Gly Val Gln Leu
1               5                   10                  15

Cys Asn Gln Tyr Gly Lys Pro Ile Gln Leu Arg Gly Met Ser Thr His
            20                  25                  30

Gly Ile Gln Trp Phe Gly Asn Cys Val Asn Asn Ala Ser Leu Asp Ala
        35                  40                  45

Leu Ala Asn Asp Trp Arg Ala Asp Ile Phe Arg Ile Ala Met Tyr Ile
    50                  55                  60

Gln Glu Asp Gly Tyr Glu Thr Asn Pro Ala Gly Thr Asn Arg Val Asn
65                  70                  75                  80

Asn Leu Val Glu Glu Ala Thr Ala Arg Gly Met Tyr Val Leu Ile Asp
                85                  90                  95

Trp His Ile Leu Thr Pro Gly Asp Pro Asn Tyr Asn Leu Asp Arg Ala
            100                 105                 110

Lys Thr Phe Phe Ala Glu Ile Ala Ala Arg His Ala Ser Lys Thr Asn
        115                 120                 125

Val Ile Tyr Glu Ile Ala Asn Glu Pro Asn Gly Gly Val Ser Trp Ser
    130                 135                 140

Asn Thr Ile Lys Ser Tyr Ala Glu Glu Val Ile Pro Val Ile Arg Ala
145                 150                 155                 160

Asn Asp Pro Asp Ser Val Ile Val Gly Thr Arg Gly Trp Ser Ser
                165                 170                 175

Asp Ser Thr Glu Ile Val Asn Asn Pro Val Asn Ala Ser Asn Ile Met
            180                 185                 190

Tyr Ala Phe His Phe Tyr Ala Ala Ser His Arg Asp Asn Tyr Arg Asp
        195                 200                 205

Glu Val Glu Arg Ala Ala Ala Arg Gly Leu Pro Val Phe Val Thr Glu
    210                 215                 220

Phe Gly Thr Val Thr Tyr Thr Gly Asp Gly Gly Asn Asp Leu Ala Ser
225                 230                 235                 240

Ser Gln Lys Trp Leu Asp Leu Leu Asp Ala Arg Lys Ile Gly Trp Ala
                245                 250                 255

Asn Trp Asn Phe Ser Asp Lys Ala Glu Ser Ser Ala Ala Leu Arg Pro
            260                 265                 270

Gly Thr Cys Ala Gly Gly Ser Trp Thr Gly Thr Ser Leu Thr Pro Ser
        275                 280                 285

Gly Val Phe Val Arg Glu Arg Ile Arg
    290                 295
```

<210> SEQ ID NO 13
<211> LENGTH: 297
<212> TYPE: PRT
<213> ORGANISM: Artificial Sequence
<220> FEATURE:
<223> OTHER INFORMATION: Ancestral endocellulase

<400> SEQUENCE: 13

```
Thr Pro Val Glu Thr His Gly Gln Leu Ser Val Lys Gly Gly Gln Leu
1               5                   10                  15

Val Asp Glu Asn Gly Lys Pro Val Gln Leu Arg Gly Met Ser Ser His
            20                  25                  30

Gly Leu Gln Trp Phe Gly Asp Phe Val Asn Lys Asp Ser Met Lys Trp
        35                  40                  45
```

```
Leu Arg Asp Asp Trp Gly Ile Asn Val Phe Arg Val Ala Met Tyr Thr
    50                  55                  60

Ala Glu Asp Gly Tyr Ile Thr Asn Pro Ser Val Lys Asn Lys Val Lys
 65                  70                  75                  80

Glu Ala Val Glu Ala Ile Asp Leu Gly Met Tyr Val Ile Ile Asp
                 85                  90                  95

Trp His Ile Leu Ser Asp Asn Asp Pro Asn Thr Tyr Lys Ala Gln Ala
                100                 105                 110

Lys Ala Phe Phe Gln Glu Met Ala Leu Tyr Gly Asn Tyr Pro Asn
            115                 120                 125

Val Ile Tyr Glu Ile Ala Asn Glu Pro Asn Gly Asn Val Thr Trp Asn
130                 135                 140

Asn Gln Ile Lys Pro Tyr Ala Glu Glu Val Ile Pro Val Ile Arg Ala
145                 150                 155                 160

Lys Asp Pro Asp Asn Ile Ile Val Gly Thr Gly Thr Trp Ser Gln
                165                 170                 175

Asp Val His Asp Ala Ala Asp Asn Pro Leu Pro Asp Ser Asn Ile Met
                180                 185                 190

Tyr Ala Leu His Phe Tyr Ala Gly Thr His Gly Gln Phe Leu Arg Asp
            195                 200                 205

Arg Ile Asp Tyr Ala Leu Ser Lys Gly Ala Ala Ile Phe Val Thr Glu
            210                 215                 220

Trp Gly Thr Ser Asp Ala Ser Gly Asn Gly Pro Phe Leu Pro Glu
225                 230                 235                 240

Ser Gln Glu Trp Ile Asp Phe Met Asn Ser Arg Lys Ile Ser Trp Ala
                245                 250                 255

Asn Trp Ser Leu Ser Asp Lys Ser Glu Thr Ser Ala Ala Leu Met Pro
            260                 265                 270

Gly Ala Ser Pro Thr Gly Gly Trp Thr Glu Ser Gln Leu Ser Ala Ser
            275                 280                 285

Gly Lys Phe Val Arg Glu Gln Ile Arg
            290                 295

<210> SEQ ID NO 14
<211> LENGTH: 163
<212> TYPE: PRT
<213> ORGANISM: Artificial Sequence
<220> FEATURE:
<223> OTHER INFORMATION: Carbohydrate binding domain

<400> SEQUENCE: 14

Met Thr Pro Gly Glu Glu Phe Tyr Val Glu Ala Ala Val Asn Ala
 1               5                  10                  15

Gly Pro Gly Phe Val Asn Ile Lys Ala Ser Ile Ile Asn Lys Ser Gly
                20                  25                  30

Trp Pro Ala Arg Gly Ser Asp Lys Leu Ser Ala Lys Tyr Phe Val Asp
            35                  40                  45

Ile Ser Glu Ala Val Ala Lys Gly Ile Thr Leu Asp Gln Ile Thr Val
    50                  55                  60

Gln Ser Thr Thr Asn Gly Gly Ala Lys Val Ser Gln Leu Leu Pro Trp
 65                  70                  75                  80

Asp Pro Asp Asn His Ile Tyr Tyr Val Asn Ile Asp Phe Thr Gly Ile
                 85                  90                  95

Asn Ile Phe Pro Gly Gly Ile Asn Glu Tyr Lys Arg Asp Val Tyr Phe
                100                 105                 110
```

```
Thr Ile Thr Ala Pro Tyr Gly Glu Gly Asn Trp Asp Asn Thr Asn Asp
            115                 120                 125

Phe Ser Phe Gln Gly Leu Glu Gln Gly Phe Thr Ser Lys Lys Thr Glu
    130                 135                 140

Tyr Ile Pro Leu Tyr Asp Gly Asn Val Arg Val Trp Gly Lys Val Pro
145                 150                 155                 160

Asp Arg Ser

<210> SEQ ID NO 15
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 15

Phe Thr Val Gln Trp Lys Lys Ser Ser Trp Glu Glu Gly Gly Lys
1               5                   10                  15

Lys Cys Gly Gly Tyr Glu Ile Val Ile Thr Asn Asn Gly Asp Thr Val
                20                  25                  30

Asn Ser Trp Thr Ala Lys Val Thr Val Pro Gly Asn Thr Lys Leu Met
            35                  40                  45

Ser Gln Trp Asn Gly Ile Phe Ser Ile Ser Gly Asn Thr Met Thr Val
    50                  55                  60

Lys Asn Glu Ser Tyr Asn Gly Thr Ile Glu Lys Gly Lys Ser Ile Ser
65                  70                  75                  80

Phe Gly Phe Asn Tyr Ser Ala
                85

<210> SEQ ID NO 16
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 16

Tyr Gln Leu Lys Val Thr Val Ser Ser Trp Glu Ser Gly Asp Gly
1               5                   10                  15

Tyr Gly Thr Tyr Ser Leu Ser Phe Thr Asn Arg Ser Ala Ala Val
                20                  25                  30

Lys Ala Trp Asp Ala Gln Ile Glu Val Pro Glu Gly Ser Lys Val Thr
            35                  40                  45

Glu Ala Trp Gly Cys Glu Thr Gly Ile Asp Gly Thr Ile Leu Thr Val
    50                  55                  60

Thr Ala Lys Asp Trp Gly Ala Ala Val Ala Lys Gly Ser Thr Val Glu
65                  70                  75                  80

Ile Gly Phe Asn Met Asp Thr
                85

<210> SEQ ID NO 17
<211> LENGTH: 84
<212> TYPE: PRT
<213> ORGANISM: Artificial Sequence
<220> FEATURE:
<223> OTHER INFORMATION: Carbohydrate binding domain

<400> SEQUENCE: 17

Tyr Lys Ala Asp Phe Lys Val Val Asn Ser Trp Glu Glu Gly Gly Lys
1               5                   10                  15
```

```
Lys Cys Tyr Gln Leu Ser Gly Thr Leu Thr Asn Leu Ser Ser Ser Ile
            20                  25                  30

Ser Ser Trp Thr Val Val Phe Asp Ala Gly Asn Gly Ala Glu Ile Lys
        35                  40                  45

Gln Phe Trp Asn Ser Lys Cys Thr Ile Ser Gly Asn Lys Ile Thr Val
 50                  55                  60

Gly Pro Ala Asp Tyr Asn Ser Arg Ile Gly Thr Gly Ala Ser Val Ser
 65                  70                  75                  80

Asp Val Gly Met
```

<210> SEQ ID NO 18
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 18

```
Phe Tyr Ala Glu Ile Gly His Asp Ser Thr Trp Glu Ala Ser Gly Lys
 1               5                  10                  15

Thr Cys Ala Thr Glu Asn Ile Asn Ile Tyr Asn Lys Thr Ser Ser Val
            20                  25                  30

Ser Gly Trp Lys Leu Asp Val Ile Tyr Lys Gly Lys Pro Ala Ile Glu
        35                  40                  45

Asp Ile Trp Asn Gly Glu Lys Lys Ile Asn Glu Tyr Thr Val Ser Ile
 50                  55                  60

Thr Pro Ala Asp Tyr Asn Gln Asp Ile Pro Ala Gly Gly Ser Val Asn
 65                  70                  75                  80

Val Gly Tyr Asn Ile Ala Ser
                85
```

<210> SEQ ID NO 19
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 19

```
Tyr Tyr Ala Ser Ile Ser Asp Asn Ser Ser Trp Gln Glu Asn Gly Lys
 1               5                  10                  15

Asn Ala Ala Thr Lys Asn Val Ile Ile Tyr Asn Lys Asp Lys Lys Val
            20                  25                  30

Thr Gly Trp Lys Ile Glu Leu Val Phe Ala Ser Glu Pro Glu Leu Ala
        35                  40                  45

Asp Ile Trp Gly Gly Lys Ala Glu Val Asn Gly Asp Thr Ile Thr Val
 50                  55                  60

Val Gly Tyr Asp Tyr Thr Ala Glu Leu Lys Ala Gly Gly Asn Val Asn
 65                  70                  75                  80

Phe Gly Phe Asn Val Lys Ala
                85
```

<210> SEQ ID NO 20
<211> LENGTH: 77
<212> TYPE: PRT
<213> ORGANISM: Artificial Sequence
<220> FEATURE:
<223> OTHER INFORMATION: Carbohydrate binding domain

```
<400> SEQUENCE: 20

Trp Ala Glu Gln Asn Gln Thr Ala Phe Gln Tyr Glu Leu Leu Phe Ser
1               5                   10                  15

Asn Gln Ser Glu Ala Phe Gly Thr Trp Lys Val Ile Leu Asp Thr Gly
            20                  25                  30

Lys Glu Val Lys Val Gln Asn Ser Trp Asn Cys Ser Leu Glu Ala Asp
        35                  40                  45

Gly Asn Leu Leu Thr Phe Thr Pro Ala Asp Tyr Asn Ala Lys Leu Ala
    50                  55                  60

Lys Gly Ala Glu Met Ala Asp Val Gly Met Ile Leu Val
65                  70                  75

<210> SEQ ID NO 21
<211> LENGTH: 85
<212> TYPE: PRT
<213> ORGANISM: Artificial Sequence
<220> FEATURE:
<223> OTHER INFORMATION: Carbohydrate binding domain

<400> SEQUENCE: 21

Met Gln Phe Lys Gln Ser Asn Ser Trp Glu Gly Asn Gly Arg Phe Tyr
1               5                   10                  15

Ala Gln Tyr Asp Leu Ile Ile Asp Asn Lys Glu Asp Val Ile Ser Asp
            20                  25                  30

Trp Thr Phe Lys Ile Asn Thr Thr Asn Gly Thr Thr Leu Glu Gln Ser
        35                  40                  45

Trp Asn Cys Thr Val Asp Thr Ser Asp Leu Gln Trp Ser Val Val Pro
    50                  55                  60

Val Asp Tyr Asn Lys Ile Ile Glu Ser Gln Ala Gln Met Asn Asn Val
65                  70                  75                  80

Gly Phe Ile Ile Ser
                85

<210> SEQ ID NO 22
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 22

Asn Gly Ile Ser Val Gln Tyr Arg Ala Gly Asp Gly Ser Met Asn Ser
1               5                   10                  15

Asn Gln Ile Arg Pro Gln Leu Gln Ile Lys Asn Asn Gly Asn Thr Thr
            20                  25                  30

Val Asp Leu Lys Asp Val Thr Ala Arg Tyr Trp Tyr Asn Ala Lys Asn
        35                  40                  45

Lys Gly Gln Asn Val Asp Cys Asp Tyr Ala Gln Leu Gly Cys Gly Asn
    50                  55                  60

Val Thr Tyr Lys Phe Val Thr Leu His Lys Pro Lys Gln Gly Ala Asp
65                  70                  75                  80

Thr Tyr Leu Glu Leu Gly Phe Lys Asn Gly Thr Leu Ala Pro Gly Ala
                85                  90                  95

Ser Thr Gly Asn Ile Gln Leu Arg Leu His Asn Asp Asp Trp Ser Asn
                100                 105                 110

Tyr Ala Gln Ser Gly Asp Tyr Ser Phe Phe Lys Ser Asn Thr Phe Lys
                115                 120                 125
```

```
Thr Thr Lys Lys Ile Thr Leu Tyr Asp Gln Gly Lys Leu Ile Trp Gly
            130                 135                 140

Thr Glu Pro
145

<210> SEQ ID NO 23
<211> LENGTH: 137
<212> TYPE: PRT
<213> ORGANISM: Artificial Sequence
<220> FEATURE:
<223> OTHER INFORMATION: Carbohydrate binding domain

<400> SEQUENCE: 23

Asn Gly Ile Ser Val Gln Tyr Arg Ala Gly Asp Gly Ser Met Asn Ser
1               5                   10                  15

Asn Gln Ile Arg Pro Gln Leu Gln Ile Lys Asn Asn Gly Asn Thr Thr
            20                  25                  30

Val Asp Leu Lys Asp Val Thr Ala Arg Tyr Trp Tyr Lys Ala Lys Asn
        35                  40                  45

Lys Gly Gln Asn Val Asp Cys Asp Tyr Ala Gln Ile Gly Cys Gly Asn
    50                  55                  60

Val Thr Tyr Lys Phe Val Thr Leu His Lys Pro Lys Gln Gly Ala Asp
65                  70                  75                  80

Thr Tyr Leu Glu Leu Gly Phe Lys Asn Gly Thr Leu Ala Pro Gly Ala
                85                  90                  95

Ser Thr Gly Asn Ile Gln Leu Arg Leu His Asn Asp Asp Trp Ser Asn
            100                 105                 110

Tyr Ala Gln Ser Gly Asp Tyr Ser Phe Phe Lys Ser Asn Thr Phe Lys
        115                 120                 125

Thr Thr Lys Lys Ile Thr Leu Tyr Asp
    130                 135

<210> SEQ ID NO 24
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 24

Asn Gly Ile Ser Val Gln Tyr Lys Ala Gly Asp Gly Gly Val Asn Ser
1               5                   10                  15

Asn Gln Ile Arg Pro Gln Leu His Ile Lys Asn Asn Gly Asn Ala Thr
            20                  25                  30

Val Asp Leu Lys Asp Val Thr Ala Arg Tyr Trp Tyr Asn Ala Lys Asn
        35                  40                  45

Lys Gly Gln Asn Phe Asp Cys Asp Tyr Ala Gln Ile Gly Cys Gly Asn
    50                  55                  60

Leu Thr His Lys Phe Val Thr Leu His Lys Pro Lys Gln Gly Ala Asp
65                  70                  75                  80

Thr Tyr Leu Glu Leu Gly Phe Lys Thr Gly Thr Leu Ser Pro Gly Ala
                85                  90                  95

Ser Thr Gly Asn Ile Gln Leu Arg Leu His Asn Asp Asp Trp Ser Asn
            100                 105                 110

Tyr Ala Gln Ser Asp Asp Tyr Ser Phe Phe Gln Ser Asn Thr Phe Lys
        115                 120                 125

Thr Thr Lys Lys Ile Thr Leu Tyr His Gln Gly Lys Leu Ile Trp Gly
    130                 135                 140
```

Thr Glu Pro
145

<210> SEQ ID NO 25
<211> LENGTH: 63
<212> TYPE: PRT
<213> ORGANISM: Artificial Sequence
<220> FEATURE:
<223> OTHER INFORMATION: Carbohydrate binding domain

<400> SEQUENCE: 25

Pro Gly Glu Pro Glu Pro Asp Pro Gly Glu Pro Asp Pro Thr Pro Pro
1               5                   10                  15

Ser Asp Gly Asp Tyr Pro Ala Trp Asp Pro Asn Thr Ile Tyr Thr Asp
                20                  25                  30

Glu Ile Val Tyr His Asn Gly Gln Leu Trp Gln Ala Lys Trp Trp Thr
            35                  40                  45

Gln Asn Gln Glu Pro Gly Asp Tyr Gly Pro Trp Glu Pro Leu Asn
        50                  55                  60

<210> SEQ ID NO 26
<211> LENGTH: 145
<212> TYPE: PRT
<213> ORGANISM: Artificial Sequence
<220> FEATURE:
<223> OTHER INFORMATION: Carbohydrate binding domain

<400> SEQUENCE: 26

Gly Asn Leu Val Val Gln Tyr Lys Val Gly Asp Thr Ser Ala Thr Asp
1               5                   10                  15

Asn Gln Met Lys Pro Ser Phe Asn Ile Lys Asn Asn Gly Thr Thr Pro
                20                  25                  30

Val Asn Leu Ser Gly Leu Lys Leu Arg Tyr Tyr Phe Thr Lys Asp Gly
            35                  40                  45

Thr Asp Met Ser Ala Ser Ile Asp Trp Ala Gln Ile Gly Ala Ser Asn
        50                  55                  60

Ile Ser Ala Ala Phe Ala Asp Phe Thr Gly Ser Asn Thr Asp Thr Tyr
65                  70                  75                  80

Val Glu Leu Ser Phe Ser Ala Gly Ser Ile Pro Ala Gly Gly Gln Thr
                85                  90                  95

Gly Asp Ile Gln Leu Arg Met Tyr Lys Thr Asp Trp Ser Asn Phe Asn
            100                 105                 110

Glu Ala Asn Asp Tyr Ser Tyr Asp Gly Ala Lys Thr Tyr Ala Asp Trp
        115                 120                 125

Asn Arg Val Thr Leu His Gln Asn Gly Thr Leu Val Trp Gly Thr Thr
    130                 135                 140

Pro
145

<210> SEQ ID NO 27
<211> LENGTH: 57
<212> TYPE: PRT
<213> ORGANISM: Artificial Sequence
<220> FEATURE:
<223> OTHER INFORMATION: Carbohydrate binding domain

<400> SEQUENCE: 27

Asp Pro Gly Glu Pro Asp Pro Thr Pro Pro Ser Asp Gly Glu Tyr Pro
1               5                   10                  15

Ala Trp Asp Pro Asn Gln Ile Tyr Thr Asn Glu Ile Val Tyr His Asn
            20                  25                  30

Gly Gln Leu Trp Gln Ala Lys Trp Trp Thr Gln Asn Gln Glu Pro Gly
            35                  40                  45

Asp Tyr Gly Pro Trp Glu Pro Leu Asn
            50                  55

<210> SEQ ID NO 28
<211> LENGTH: 144
<212> TYPE: PRT
<213> ORGANISM: Artificial Sequence
<220> FEATURE:
<223> OTHER INFORMATION: Carbohydrate binding domain

<400> SEQUENCE: 28

Gly Ser Leu Val Leu Gln Tyr Arg Ala Ala Asp Thr Asn Ala Gly Asp
1               5                   10                  15

Asn Ala Ile Lys Pro His Phe Asn Ile Arg Asn Thr Gly Ala Ser Pro
            20                  25                  30

Val Asp Leu Ser Gly Val Lys Leu Arg Tyr Tyr Phe Thr Lys Asp Gly
            35                  40                  45

Ile Pro Leu Ser Phe Ala Val Asp Trp Ala Gln Val Gly Ser Pro Asn
        50                  55                  60

Val Lys Gly Thr Phe Gly Ser Ala Ser Gly Ala Gly Ala Asp Thr Tyr
65                  70                  75                  80

Leu Glu Val Ser Phe Thr Gly Ser Ile Pro Ala Gly Gly Gln Thr Gly
            85                  90                  95

Glu Ile Gln Thr Arg Ile His Lys Ser Asp Trp Ser Ser Phe Gln Glu
            100                 105                 110

Ser Gly Asp Tyr Ser Tyr Asp Pro Gly Lys Thr Tyr Ala Asp Trp Ser
            115                 120                 125

Lys Val Thr Leu Tyr Arg Asp Gly Thr Arg Val Trp Gly Val Glu Pro
            130                 135                 140

<210> SEQ ID NO 29
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 29

Asn Ile Thr Ser Ala Val Tyr Thr Ile Ser Asn Thr Asp Pro Val Lys
1               5                   10                  15

Gln Val Ser Ala Pro Thr Phe Ser Leu Gln Ser Ala Gln Thr Val Thr
            20                  25                  30

Leu Thr Ser Ser Asp Asn Asp Ser Val Ile His Tyr Thr Thr Asp Gly
            35                  40                  45

Thr Pro Thr Ser Ser Pro Val Tyr Thr Asn Met Thr Asp Ser Ser
        50                  55                  60

Val Val Thr Asn Thr Tyr Thr Ile Thr Asn Glu Thr Ser Asn Ser Pro
65                  70                  75                  80

Val Glu Val Glu Val Glu Tyr Lys Thr Val Lys Val Thr Leu Thr
            85                  90                  95

Asn Asn Ser Ser Thr Pro Ile Asn Gly Trp Lys Leu Ser Trp Ile Asn
            100                 105                 110

Asn Met Trp Thr Ala Asn Tyr Ser Ile Lys Asp Ser Ala Ile Val Lys
            115                 120                 125

-continued

```
Asp Tyr Asn Asn Ile Ile Pro Ala Asn Gly Gly Thr Gln Ile Phe Gly
        130                 135                 140

Phe Ser Ile
145

<210> SEQ ID NO 30
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 30

Gln Gly Ile Val Leu Gln Tyr Arg Thr Gly Asp Thr Asn Thr Lys Asp
1               5                   10                  15

Asn Ala Ile Arg Pro Glu Phe Asn Ile Lys Asn Thr Gly Asn Thr Ala
            20                  25                  30

Val Lys Leu Ser Asp Leu Lys Ile Arg Tyr Tyr Tyr Thr Asp Glu Ser
        35                  40                  45

Lys Gly Gln Gln Leu Phe Val Asp Trp Ala Lys Val Gly Asn Glu Lys
    50                  55                  60

Val Lys Ala Thr Phe Val Ala Leu Pro Glu Pro Lys Ala Lys Ala Asp
65                  70                  75                  80

Lys Tyr Val Glu Ile Ser Phe Thr Asp Gly Thr Ile Gln Pro Gly Gly
                85                  90                  95

Glu Ser Gly Glu Ile Gln Pro Arg Ile His Ala Ala Asn Trp Ser Asn
            100                 105                 110

Phe Asp Glu Thr Asn Asp Tyr Ser Tyr Gly Ala Ser Gln Thr Phe Ala
        115                 120                 125

Asn Trp Asp His Ala Thr Val Tyr Gln Gln Gly Lys Leu Val Trp Gly
    130                 135                 140

Ile Glu Pro
145

<210> SEQ ID NO 31
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 31

Glu Gly Ile Val Leu Gln Tyr Arg Thr Asp Thr Asn Ala Lys Asp
1               5                   10                  15

Asn Ala Ile Arg Pro Gln Phe Asn Ile Lys Asn Thr Gly Lys Thr Ala
            20                  25                  30

Val Lys Leu Ser Asp Leu Lys Ile Arg Tyr Tyr Tyr Thr Asp Glu Ser
        35                  40                  45

Lys Ala Gln Gln Phe Phe Val Asp Trp Ala Lys Ile Gly Asn Glu Lys
    50                  55                  60

Val Lys Ala Thr Phe Val Thr Leu Pro Asn Pro Lys Ser Lys Ala Asp
65                  70                  75                  80

Lys Tyr Val Glu Ile Ser Phe Thr Asp Gly Thr Ile Gln Pro Gly Gly
                85                  90                  95

Glu Thr Gly Glu Ile Gln Ser Arg Ile His Ala Ala Asn Trp Ser Asn
            100                 105                 110

Phe Asp Glu Thr Asn Asp Tyr Ser Tyr Gly Ala Ala Gln Thr Phe Ala
```

115                 120                 125
Asp Trp Asp His Gly Thr Val Tyr Gln Gln Gly Lys Leu Val Trp Gly
        130                 135                 140

Ile Glu Pro
145

<210> SEQ ID NO 32
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 32

Gln Ala Ala Gly Leu Thr Ala Thr Val Thr Lys Glu Ser Ser Trp Asp
1               5                   10                  15

Asn Gly Tyr Ser Ala Ser Val Thr Val Arg Asn Asp Thr Ser Ser Val
            20                  25                  30

Ser Gln Trp Glu Val Val Leu Thr Leu Pro Gly Gly Thr Thr Val Ala
        35                  40                  45

Gln Val Trp Asn Ala Gln His Thr Ser Ser Gly Asn Ser His Thr Phe
    50                  55                  60

Thr Gly Val Ser Trp Asn Ser Thr Ile Pro Pro Gly Gly Thr Ala Ser
65                  70                  75                  80

Phe Gly Phe Ile Ala Ser Gly Ser Gly Glu Pro Thr His Cys Thr Ile
                85                  90                  95

Asn Gly Ala Pro Cys Asp Glu Gly Ser Glu Pro
            100                 105

<210> SEQ ID NO 33
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 33

Ala Ala Thr Gly Cys Ser Val Thr Tyr Thr Thr Asn Ser Trp Ser Asn
1               5                   10                  15

Gly Phe Thr Ala Asn Val Thr Val Thr Asn Leu Gly Asp Ala Ile Gly
            20                  25                  30

Asn Trp Thr Leu Gly Phe Ser Phe Pro Ser Gly Gln Arg Val Thr Gln
        35                  40                  45

Gly Trp Ser Ala Ile Trp Ser Gln Ser Gly Asn Ala Val Thr Ala Arg
    50                  55                  60

Ser Glu Ser Trp Asn Gly Asn Leu Ala Thr Gly Ala Ser Thr Ser Ile
65                  70                  75                  80

Gly Phe Asn Gly Ser Phe Thr Gly Ser Pro Thr Ser Phe Thr Leu Asn
                85                  90                  95

Gly Val Pro Cys Thr Gly Ser Thr Thr Thr
            100                 105

<210> SEQ ID NO 34
<211> LENGTH: 103
<212> TYPE: PRT
<213> ORGANISM: Artificial Sequence
<220> FEATURE:
<223> OTHER INFORMATION: Carbohydrate binding domain

<400> SEQUENCE: 34

```
Glu Ala Ala Ser Phe Thr Val Thr Asn Ser Trp Ser Thr Gly Tyr Gln
1               5                   10                  15

Gly Glu Val Thr Val Ser Asn Pro Ala Ser Ser Ile Asn Thr Trp Lys
            20                  25                  30

Val Gln Leu Thr Leu Pro Ala Gly Ser Thr Ile Gly Gln Ala Trp Asn
            35                  40                  45

Ala Thr Leu Ala Thr Gly Gly Gln Thr Phe Thr Phe Thr Pro Ala Gly
        50                  55                  60

Trp Asn Gly Thr Ile Ala Gly Gly Ser Ala Thr Ser Phe Gly Phe Val
65              70                  75                  80

Val Thr Gly Thr Gly Arg Pro Thr Ser Cys Thr Val Asn Gly Gln Ala
            85                  90                  95

Cys Thr Gly Leu Thr Gly Ala
                100
```

<210> SEQ ID NO 35
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 35

```
Ala Ala Thr Gly Cys His Val Asp Tyr Thr Val Thr Asn Gln Trp Gln
1               5                   10                  15

Gly Gly Phe Gln Ala Ala Val Lys Val Thr Asn Leu Gly Asp Ala Ile
            20                  25                  30

Thr Gly Trp Leu Leu Arg Phe Thr Phe Pro Ala Gly Gln Lys Val Ala
            35                  40                  45

Gln Gly Trp Asn Ala Thr Trp Ala Gln Ser Gly Ala Thr Ala Thr Ala
        50                  55                  60

Ala Asn Ala Asp Trp Asn Arg Thr Leu Thr Thr Gly Ala Thr Thr Glu
65              70                  75                  80

Leu Gly Phe Thr Gly Thr Thr Thr Gly Val Pro Ala Ser Phe Thr Leu
            85                  90                  95

Asn Gly Val Thr Cys Thr Gly Ser Thr Thr
                100                 105
```

<210> SEQ ID NO 36
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 36

```
Ala Ala Thr Gly Cys Ala Val Thr Tyr Thr Thr Asn Ser Trp Gln Gly
1               5                   10                  15

Gly Phe Thr Ala Thr Val Ala Val Arg Asn Leu Gly Asp Pro Val Ser
            20                  25                  30

Asn Trp Thr Leu Gly Phe Thr Phe Pro Gly Gly Gln Arg Val Val Gln
            35                  40                  45

Gly Trp Ser Ala Thr Trp Gln Gln Ser Gly Ser Ala Val Thr Ala Arg
        50                  55                  60

Ser Leu Asp Tyr Asn Gly Ala Leu Gly Thr Gly Ala Ser Thr Thr Ile
65              70                  75                  80

Gly Phe Asn Gly Ser Trp Thr Gly Ser Pro Thr Ser Phe Thr Leu Asn
```

```
                 85                  90                  95

Gly Thr Val Cys Thr Gly Gly Thr Ser Thr
            100                 105

<210> SEQ ID NO 37
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 37

Ala Ala Thr Gly Cys Ala Val Thr Tyr Thr Thr Asn Ser Trp Gln Gly
1               5                   10                  15

Gly Phe Thr Ala Thr Val Ala Val Arg Asn Leu Gly Asp Pro Val Ser
            20                  25                  30

Asn Trp Thr Leu Gly Phe Thr Phe Pro Gly Gly Gln Arg Val Val Gln
        35                  40                  45

Gly Trp Ser Ala Thr Trp Gln Gln Ser Gly Ser Ala Val Thr Ala Arg
    50                  55                  60

Ser Leu Asp Tyr Asn Gly Ala Leu Gly Thr Gly Ala Ser Thr Thr Ile
65                  70                  75                  80

Gly Phe Asn Gly Ser Trp Thr Gly Ser Pro Thr Ser Phe Thr Leu Asn
                85                  90                  95

Gly Thr Val Cys Thr Gly Gly Thr Ser Thr
            100                 105

<210> SEQ ID NO 38
<211> LENGTH: 100
<212> TYPE: PRT
<213> ORGANISM: Artificial Sequence
<220> FEATURE:
<223> OTHER INFORMATION: Carbohydrate binding domain

<400> SEQUENCE: 38

Glu Ser Glu Asn Ala Thr Ile Ser Arg Gly Val Val Glu Ala Asn His
1               5                   10                  15

Thr Gly Phe Thr Gly Ser Gly Phe Val Asn Tyr Asp Asn Val Thr Gly
            20                  25                  30

Ser Tyr Val Glu Tyr Thr Val Asn Ala Ala Gln Ala Gly Pro His Thr
        35                  40                  45

Leu Thr Phe Arg Tyr Ala Asn Gly Thr Thr Ala Asn Arg Pro Leu Asp
    50                  55                  60

Ile Thr Val Asn Gly Ser Ile Ala Val Asp Asp Leu Gly Phe Ala Gly
65                  70                  75                  80

Thr Gly Ala Trp Ser Thr Val Thr Thr Val Asn Leu Ala Ala Gly
                85                  90                  95

Ser Asn Lys Ile
            100

<210> SEQ ID NO 39
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 39

Asn Ala Ala Gly Cys Arg Val Asp Tyr Thr Val Thr Asn Gln Trp Gln
1               5                   10                  15
```

```
Gly Gly Phe Gln Ala Gly Val Lys Ile Thr Asn Leu Gly Asp Thr Val
            20                  25                  30

Arg Gly Trp Thr Leu Lys Phe Thr Leu Pro Thr Gly Gln Lys Val Val
        35                  40                  45

Gln Gly Trp Ser Ala Ala Trp Ser Gln Ser Gly Ser Thr Val Thr Val
    50                  55                  60

Ala Gly Ala Asp Trp Asn Gly Thr Leu Ala Thr Gly Ala Ser Ala Asp
65                  70                  75                  80

Thr Gly Phe Val Gly Ser Phe Thr Gly Lys Pro Ala Phe Thr Leu
            85                  90                  95

Asn Gly Val Ala Cys Thr Gly Ser Val Asp Asp
            100                 105

<210> SEQ ID NO 40
<211> LENGTH: 105
<212> TYPE: PRT
<213> ORGANISM: Artificial Sequence
<220> FEATURE:
<223> OTHER INFORMATION: Carbohydrate binding domain

<400> SEQUENCE: 40

Ala Ala Thr Gly Cys Lys Ala Glu Tyr Thr Ile Ser Gln Trp Glu
1               5                   10                  15

Gly Gly Phe Gln Ala Gly Val Lys Ile Thr Asn Leu Gly Asp Pro Val
            20                  25                  30

Ser Gly Trp Thr Leu Gly Phe Thr Met Pro Ala Gly Gln Arg Leu Val
        35                  40                  45

Gln Gly Trp Asn Ala Thr Trp Ser Gln Ser Gly Ser Ala Val Thr Ala
    50                  55                  60

Gly Gly Val Asp Trp Asn Arg Thr Leu Ala Thr Gly Ala Ser Ala Asp
65                  70                  75                  80

Leu Gly Phe Val Gly Ser Phe Thr Gly Ala Pro Thr Ser Phe Thr Leu
            85                  90                  95

Asn Gly Ala Thr Cys Ser Gly Ser Val
            100                 105

<210> SEQ ID NO 41
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 41

Asp Gly Ile Gln Thr Glu Ser Thr Thr Asp Thr Gly Gly Gly Leu Asn
1               5                   10                  15

Ile Gly Trp Thr Asp Ala Gly Asp Trp Thr Ser Pro Ala Ala Gly Arg
            20                  25                  30

Tyr Lys Val Ser Tyr Arg Asn Ser Gly Met Leu Gln Leu Glu Ala Ala
        35                  40                  45

Gly Gly Phe Pro Thr Tyr Gly Ser Ile Thr Gly Gly Trp Gln Ser Trp
    50                  55                  60

Gln Thr Ile Ser His Glu Val Asn Leu Asn Trp Ile Lys Val Glu Pro
65                  70                  75                  80

Ala

<210> SEQ ID NO 42
```

```
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 42

Pro Thr Glu Pro Thr Asn Pro Gly Asn Gly Thr Thr Gly Asp Val Val
1               5                   10                  15

Leu Gln Tyr Arg Asn Val Asp Asn Asn Pro Ser Asp Asp Ala Ile Arg
            20                  25                  30

Met Ala Val Asn Ile Lys Asn Thr Gly Ser Thr Pro Ile Lys Leu Ser
        35                  40                  45

Asp Leu Gln Val Arg Tyr Tyr Phe His Asp Asp Gly Lys Pro Gly Ala
    50                  55                  60

Asn Leu Phe Val Asp Trp Ala Asn Val Gly Pro Asn Asn Ile Val Thr
65                  70                  75                  80

Ser

<210> SEQ ID NO 43
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 43

Pro Thr Glu Pro Thr Asn Pro Gly Asn Gly Thr Thr Gly Asp Ile Val
1               5                   10                  15

Leu Gln Tyr Arg Asn Val Asp Asn Asn Pro Ser Asp Asp Ala Ile Arg
            20                  25                  30

Met Ala Phe Asn Ile Lys Asn Thr Gly Ser Thr Pro Ile Lys Leu Ser
        35                  40                  45

Asp Leu Gln Val Arg Tyr Tyr Phe His Asp Asp Gly Lys Pro Gly Ala
    50                  55                  60

Asn Leu Phe Val Asp Trp Ala Asn Val Gly Pro Asn Asn Ile Val Thr
65                  70                  75                  80

Ser

<210> SEQ ID NO 44
<211> LENGTH: 78
<212> TYPE: PRT
<213> ORGANISM: Artificial Sequence
<220> FEATURE:
<223> OTHER INFORMATION: Carbohydrate binding domain

<400> SEQUENCE: 44

Ser Ser Ser Ser Ala Val Ser Ser Gln Thr Gln Val Ser Ser Ser Ser
1               5                   10                  15

Gln Ala Pro Val Val Ser Ser Ser Ser Thr Ala Ser Ser Val Val
            20                  25                  30

Ser Ser Ala Val Ser Gly Tyr Gly Thr Leu Tyr Pro Leu Cys Ser Thr
        35                  40                  45

Thr Thr Asn Gly Trp Gly Trp Glu Asn Asn Ala Ser Cys Ile Ala Arg
    50                  55                  60

Ala Thr Cys Ser Gly Gln Pro Ser Ser Ser Val Arg Ser Ser
65                  70                  75
```

ANCESTRAL CELLULASES AND USES THEREOF

FIELD OF THE INVENTION

The present invention falls within the field of enzymes, particularly exocellulases and beta-glucosidases, and their use in the degradation of cellulose and production of bioethanol.

BACKGROUND OF THE INVENTION

Over the past years, cellulose enzymes have attracted the interest of the scientific community as well as the industry due to their many biotechnological applications. Their production has increased exponentially and has encountered an important source of application in the production of bioethanol. Second-generation bioethanol made from lignocellulosic biomass is considered one of the most promising biofuels. However, the enzymatic hydrolysis of the cellulose component to liberate glucose for ethanol fermentation is one of the major barriers for the process to be economically competitive because of the cell wall recalcitrance of feedstock.

Efficient degradation of cellulosic biomass requires the synergistic action of the cellulolytic enzymes endocellulase, exocellulase and β-glucosidase. In order to increase bioethanol production, interest has been focused on the identification and optimization of fungal, yeast and bacterial cellulases and cellulolytic strains. Aside from traditional mutagenesis for improving the secretion level and enzymatic activities of cellulases, genetic engineering of strains and protein engineering on cellulase molecules enabled an increased yield. Bacterial and yeast cellulases are often preferred as these organisms have higher growth rates, although bacterial cellulases are able to deal better with the harsh conditions of industrial settings than eukaryotic ones, allowing higher rates of enzymatic hydrolysis, fermentation and product recovery.

Nevertheless, current cellulases have limited efficiency under industrial conditions. Endocellulases with improved catalytic activity even under conditions of acidic pH and/or high temperatures than the existing endocellulases have been developed (WO2017/121902). However, there is still a need in the art for other cellulases, in particular, exocellulases and beta-glucosidases, with improved physicochemical and/or functional properties over existing naturally occurring and engineered cellulases.

SUMMARY OF THE INVENTION

The authors of the present invention have developed polypeptides having exocellulase activity and beta-glucosidases having substantially improved physicochemical properties over existing naturally occurring and commercially available enzymes. When these exocellulases and beta-glucosidases are combined in an enzyme cocktail with a endocellulase, the enzyme cocktail outperformed the commercial ones in terms of specific activity (FIG. 1), production of reducing sugars (FIG. 2) and resistance to thermic inactivation (FIG. 4).

Thus, in a first aspect, the invention relates to a polypeptide comprising an exoglucanase catalytic domain, wherein the catalytic domain comprises a sequence selected from the group consisting of SEQ ID NO: 1, SEQ ID NO: 2 and SEQ ID NO: 3, or a functionally equivalent variant thereof that substantially maintains or improves its catalytic activity.

In another aspect, the invention relates to a polypeptide having beta-glucosidase activity comprising a sequence selected from the group consisting of SEQ ID NO: 6, SEQ ID NO: 7 and SEQ ID NO: 8, or a functionally equivalent variant thereof that substantially maintains or improves its catalytic activity.

In another aspect, the invention relates to a method for hydrolysing cellulose within a sample containing cellulose to cellobiose and/or cellotetraose comprising contacting said sample with the first polypeptide of the invention under suitable conditions for hydrolysing cellulose to cellobiose and/or cellotetraose.

In another aspect, the invention relates to a method for hydrolysing cellobiose and/or cellotetraose within a sample containing cellobiose and/or cellotetraose to glucose comprising contacting said sample with a the second polypeptide of the invention under suitable conditions for hydrolysing the cellobiose and/or the cellotetraose to glucose.

In another aspect, the invention relates to the use of the first polypeptide of the invention for hydrolysing cellulose to cellobiose and/or cellotetraose or of the second polypeptide of the invention for hydrolysing cellobiose and/or cellotetraose to glucose.

In another aspect, the invention relates to an enzyme cocktail selected from the group consisting of:
an enzyme cocktail comprising:
  (i) the first polypeptide of the invention further comprising a carbohydrate binding domain and
  (ii) an endoglucanase and/or a polypeptide having beta-glucosidase activity and
an enzyme cocktail comprising:
  (i) the second polypeptide of the invention and
  (ii) an endoglucanase and/or a polypeptide having exoglucanase activity.

In another aspect, the invention relates to a method for hydrolysing cellulose to glucose comprising contacting a sample comprising cellulose with the enzyme cocktail of the invention under suitable conditions for hydrolysing cellulose to glucose, wherein said enzyme cocktail comprises a polypeptide having exoglucanase activity, an endoglucanase and a polypeptide having beta-glucosidase activity.

In another aspect, the invention relates to a method for producing bioethanol comprising
  (i) hydrolysing cellulose to glucose following the method of the previous aspect and
  (ii) converting the glucose obtained in step (i) to bioethanol in the presence of a yeast capable of producing bioethanol by fermentation of glucose.

In another aspect, the invention relates to the use of the enzyme cocktail of the invention for hydrolysing cellulose to glucose or for producing bioethanol.

DETAILED DESCRIPTION OF THE INVENTION

Exoglucanase

Figure 1:
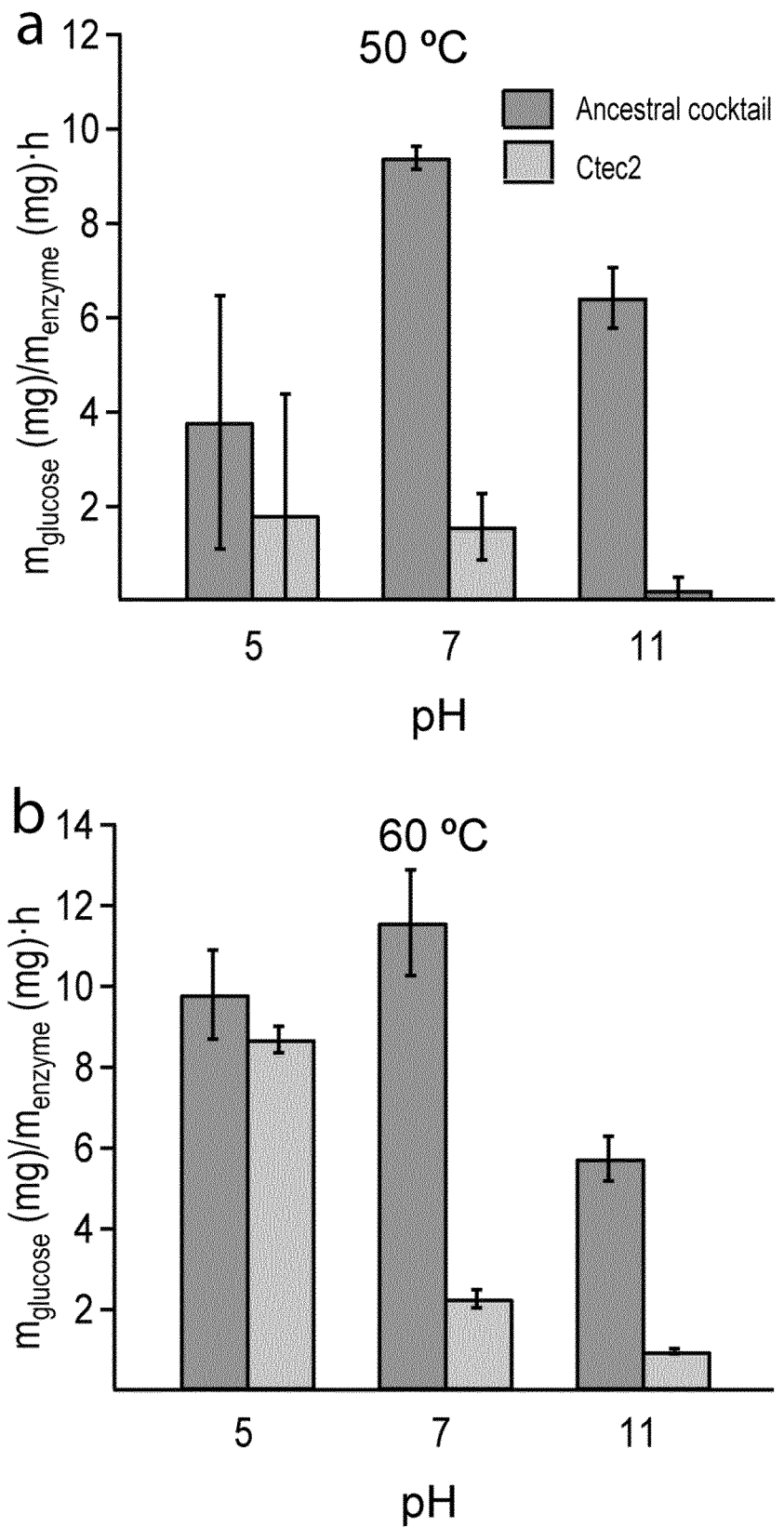
FIG. 1. Specific activity as a function of pH for ancestral enzyme cocktail and commercial enzyme cocktail Ctec2. a) 50° C., b) 60° c. and c) 70° C. Hydrolysis was carried out for 1 h using filter-paper as a substrate. All assays were triplicated. Values are reported as average±S.D.
Figure 1:
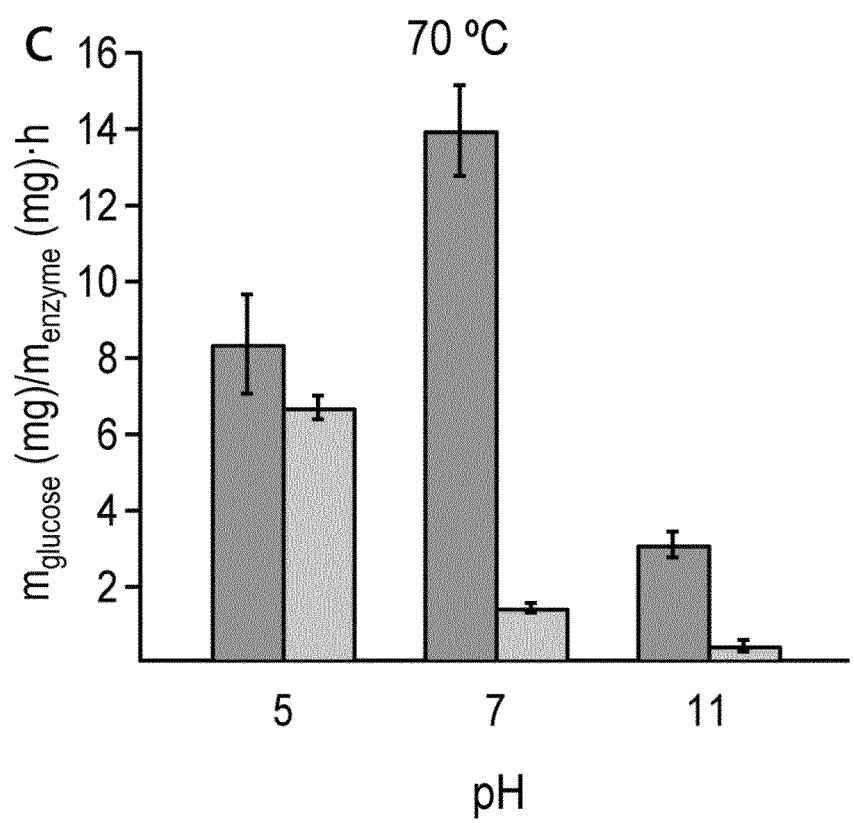

In a first aspect the invention relates to a polypeptide comprising an exoglucanase catalytic domain, hereinafter first polypeptide of the invention, wherein the catalytic domain comprises a sequence selected from the group consisting of SEQ ID NO: 1, SEQ ID NO: 2 and SEQ ID NO: 3, or a functionally equivalent variant thereof that substantially maintains or improves its catalytic activity.

The term "polypeptide", as used herein, refers to a chain of amino acids of any length wherein the different amino acids are linked to one another by means of peptide bonds or disulphide bridges.

The term "cellulase", as used herein, refers to the group of enzymes responsible for the hydrolisation of cellulose into monosaccharides or shorter polysaccharides and oligosaccharides. There are three main types of cellulases: (i) endocellulases, which cleave internal (1-4)-β-D-glucosidic linkages; (ii) exocellulases, which break (1-4)-β-D-glucosidic linkages releasing cellobiose or cellotetrose from the non-reducing ends of the chains; and (iii)β-glucosidase, which hydrolyse the remaining glycosidic links into individual monosaccharides.

The term "exoglucanase" or "exocellulase", also known as Glucan 1,4-beta-glucosidase (or 4-b eta-D-glucan glucohydrolase), exo-1,4-beta-glucosidase, exocellulase, exo-beta-1,4-beta-glucosidase, exo-beta-1,4-glucanase, beta-1,4-beta-glucanase, exo-1,4-beta-glucanase, or 1,4-beta-D-glucan glucohydrolase, or cellobiohydrolases as used herein, relates to a type of cellulase that catalyses the hydrolysis of β(1-4)-linkages in 1,4-beta-D-glucans and related oligosaccharides, removing two to four units from the ends of the exposed chains of polysaccharides releasing tetrasaccharides, disaccharides and some monosaccharides. It has been classified by the Nomenclature Committee of the International Union of Biochemistry and Molecular Biology as EC 3.2.1.91. Exoglucanases derived from bacteria have a catalytic domain and a carbohydrate binding molecule attached by a linking domain.

The term "exoglucanase catalytic domain", as used herein, refers to a domain if an exoglucanase that is responsible of its catalytic function, in particular of its exoglucanase function. The catalytic domain contains the active site, a set of amino acids with a special spacial arrangement that permits interaction with the substrate to effect the reaction.

In a particular embodiment, the first polypeptide of the invention comprises an exoglucanase catalytic domain comprising or consisting essentially of or consisting of the sequence of SEQ ID NO: 1.

In another particular embodiment, the first polypeptide of the invention comprises an exoglucanase catalytic domain comprising or consisting essentially of or consisting of the sequence of SEQ ID NO: 2.

In another particular embodiment, the first polypeptide of the invention comprises an exoglucanase catalytic domain comprising or consisting essentially of or consisting of the sequence of SEQ ID NO: 3.

In another particular embodiment, the first polypeptide of the invention comprises an exoglucanase catalytic domain comprising or consisting essentially of or consisting of a functionally equivalent variant of the exoglucanase catalytic domain of sequence of SEQ ID NO: 1, SEQ ID NO: 2 or SEQ ID NO: 3 that substantially maintains or improves its catalytic activity.

The term "functionally equivalent variant" as used herein is understood to mean all those proteins derived from a sequence by modification, insertion and/or deletion or one or more amino acids, whenever the function is substantially maintained, particularly in the case of a functionally equivalent variant of a catalytic domain refers to maintaining the catalytic activity.

In particular, the functionally equivalent variant of the exoglucanase catalytic domain of SEQ ID NO: 1, SEQ ID NO: 2 or SEQ ID NO: 3 maintains or improves the catalytic activity of the exoglucanase catalytic domain from which it derived.

The term "catalytic activity" or "enzyme activity", as used herein, refers to the ability of an enzyme to accelerate or catalyse chemical reactions. The catalytic activity is a measure of the quantity of active enzyme present and is thus dependent on reaction conditions, including temperature and/or pH, which should be specified. The commonly used unit is enzyme unit (U)=1 μmol min$^{-1}$. Another common unit is the specific activity of an enzyme, which is the activity of an enzyme per milligram of total protein (expressed in μmol min$^{-1}$mg$^{-1}$) and measures enzyme purity in the mixture.

The catalytic activity is characterised by means of the following kinetic parameters: $V_{max}$, which is the maximum speed of an enzymatic reaction; the Michaelis-Menten constant ($K_m$), which is the substrate concentration required for an enzyme to reach one-half its maximum reaction rate; and $k_{cat}$, or turnover number, which is the number of substrate molecules handled by one active site per second. These kinetic parameters depend on solution conditions, such as temperature and pH, and on substrate concentration. The efficiency of an enzyme can be expressed in terms of $k_{cat}/K_m$, or specificity constant. Because the specificity constant reflects both affinity and catalytic ability, it is useful for comparing different enzymes against each other, or the same enzyme with different substrates.

The term "catalytic activity of the exoglucanase catalytic domain", as used herein, refers to the ability of the catalytic domain to cleave or hydrolyse (1-4)-β-D-glucosidic links from the end of polysaccharide chains liberating disaccharides or tetrasaccharides.

The exoglucanase catalytic activity may be measured by means of a number of techniques assays that are conventional to the skilled person, including assays that employ microcrystalline cellulose or hydrocellulose, such as the commercial Avicel. Enzymes that show relatively high activity on Avicel and little activity on carboxymethyl cellulose (CMC) assay are identified on exoglucanases. Other assays for determining exoglucanase activity include the following: assay on 4-methylumbelliferyl-β-D-lactoside (van Tilbeurgh H. et al., Eur J Biochem 1985, 148: 329-334); assay on p-nitrophenyl-β-d-cellobioside to yield cellobiose and p-nitrophenol (Deshpande M V, et al., Anal Biochem 1984, 138: 481-487); assay on PNP-p-d-cellobioside (Kohring et al., Appl Environ Microbiol 1990, 56: 3798-3804); assay on bacterial microcrystalline cellulose (BMCC) (Caspi J. et al., J Biotechnol. 2008, 135: 351-357); assay on MU-β-d-cellobioside (MU-C) (Courty P E, et al., New Phytol. 2005, 167: 309-319).

According to the present invention, the catalytic activity of the exoglucanase catalytic domain is substantially maintained if the functionally equivalent has at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the exoglucanase catalytic domain comprising the sequence SEQ ID NO: 1, SEQ ID NO: 2 or SEQ ID NO: 3. Furthermore, the catalytic activity of the exoglucanase catalytic domain is substantially improved if the functionally equivalent variant has at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more of the catalytic activity of the exoglucanase catalytic domain comprising the sequence SEQ ID NO: 1, SEQ ID NO: 2 or SEQ ID NO: 3.

As with other enzymes, the catalytic activity of the exoglucanase catalytic domain depends on a number of reaction parameters, including temperature and pH. Thus, in one embodiment, the functionally equivalent variant of the exoglucanase catalytic domain comprising, consisting essentially of or consisting of the sequence SEQ ID NO: 1, SEQ ID NO: 2 or SEQ ID NO: 3 maintains or improves its catalytic activity at a temperature of at least 0° C., at least 5° C., at least 10° C., at least 15° C., at least 20° C., at least 25° C., at least 30° C., at least 35° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., or higher. Likewise, in another embodiment the functionally equivalent variant of the exoglucanase catalytic domain comprising, consisting essentially of or consisting of the sequence SEQ ID NO: 1, SEQ ID NO: 2 or SEQ ID NO: 3 maintains or improves its catalytic activity at pH 0, or at least pH 0.1, or at least pH 0.5, or at least pH 1.0, or at least pH 1.5, or at least pH 2.0, or at least pH 2.5, or at least pH 3.0, or at least pH 3.5, or at least pH 4.0, or at least pH 4.5, or at least pH 5.0, or at least pH 5.5, or at least pH 6.0, or at least pH 6.5, or at least pH 7.0, or at least pH 7.5, or at least pH 8.0, or at least pH 8.5, or at least pH 9.0, or at least pH 9.5, or at least pH 10.0, or at least pH 10.5, or at least pH 11.0, or at least pH 11.5, or at least pH 12.0, or at least pH 12.5, or at least pH 13.0, or at least pH 13.5, or pH 14. All possible combinations of temperatures and pH are also contemplated by the invention.

In particular embodiment, the functionally equivalent variant of the exoglucanase catalytic domain of SEQ ID NO: 1 that substantially maintains or improves its catalytic activity has at least 50%, at least 60%, at least 70%, at least 80%, at least 90%, at least 95%, or at least 99% sequence identity with SEQ ID NO: 1.

In another particular embodiment, the functionally equivalent variant of the exoglucanase catalytic domain of SEQ ID NO: 2 or SEQ ID NO: 3 that substantially maintains or improves its catalytic activity has at least 60%, at least 70%, at least 80%, at least 90%, at least 95%, or at least 99% sequence identity with SEQ ID NO: 2 or SEQ ID NO: 3.

The degree of identity between the variants and the exoglucanase catalytic domain comprising the sequence SEQ ID NO: 1, SEQ ID NO: 2 or SEQ ID NO: 3 is determined by using algorithms and computer methods which are widely known by the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J Mol Biol, 215: 403-410 (1990)]. In a preferred embodiment, the sequence identity is determined throughout the whole length of the sequence of the exoglucanase domain comprising the sequence SEQ ID NO: 1, SEQ ID NO: 2 or SEQ ID NO: 3, or through the whole length of the variant or both.

In a particular embodiment, the functionally equivalent variant of the exoglucanase catalytic domain comprising the sequence of SEQ ID NO: 1, SEQ ID NO: 2 or SEQ ID NO: 3 comprises or consists essentially of or consists of the sequence of SEQ ID NO: 4.

In a particular embodiment, the functionally equivalent variant of the exoglucanase catalytic domain comprising the sequence of SEQ ID NO: 1, SEQ ID NO: 2 or SEQ ID NO: 3 does not have the sequence of the catalytic domain of an exoglucanase selected from the group consisting of the exoglucanases shown in the UnitProt database with Accession No. Q9XCD4, W7SI25, R1IFN8, T1V3R1, D2B809, P50900, D9WNN6, B5HJV6, M3C0N9, A0LSI0, F3NPZ3, L1KHJ0, D7C1F6, D9XJA9, M1MJV0, K4QTE6, B5HPK7, D6K6C0, M3ECC0, O82831, S5UZR1, L7EZA5, W7VNI1, A4X938, A9KT91, O65986, R4LQA1, I0BR01, G7VQK6, W6AP62, E0RLD5, W4CUL3 and Q8KKF7.

In a particular embodiment, the first polypeptide of the invention further comprises a carbohydrate binding domain (CBD).

The term "carbohydrate binding domain" or "carbohydrate binding module", as used herein, refers to a protein domain that is present in carbohydrate-active enzymes (for example endocellulases and exocellulases) and having carbohydrate-binding activity. Carbohydrate binding domains contributes to the catalytic efficiency by increasing enzyme-substrate complex formations.

Illustrative non-limitative examples of CBD include CBD comprising, consisting essentially or consisting of a sequence selected from the group consisting of SEQ ID NO: 15 to 44.

In a particular embodiment, the CBD is from an extremophile organism. The term "extremophile organism", as used herein, refers to an organism that is capable of thriving in physically or geochemically extreme conditions that are detrimental to most forms of life on Earth, like conditions of extremely high or low temperature or pressure, high or low content of oxygen or carbo dioxide, high levels or radiation, acidity or alkalinity, absence of water, high concentration of salt or sugar, presence of sulphur, petroleum or other toxic substances, etc.

Illustrative non-limitative examples of extremophile organisms include *Bacillus* strains, *Thermotoga maritima*, *Thermotoga* sp, *Anaerocellum thermophilum*, *Clostridium thermocellum* and *Thermobifida fusca*.

In a particular embodiment, the CBD is from *Clostridium thermocellum*. The term "*Clostridium thermocellum*" or "*Ruminiclostridium thermocellum*" as used herein, refers to an anaerobic, thermophilic bacterium capable of directly converting a cellulosic substrate into ethanol. This microorganism is identified in the NCBI database by the Taxonomy ID: 1515.

In a more particular embodiment, the CBD comprises, consists essentially or consists of SEQ ID NO: 5 or a functionally equivalent variant thereof.

The particulars of a functionally equivalent variant in terms of sequence identity previously described in the context of the exoglucanase catalytic domain also apply to the carbohydrate binding domain, with the necessary amendments, as will be immediate for the person skilled in the art.

Thus, functionally equivalent variants of a carbohydrate binding domain comprising, consisting essentially of or consisting of the sequence SEQ ID NO: 5 also include carbohydrate binding domains comprising, consisting essentially of or consisting of amino acid sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 5, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the carbohydrate binding activity of the carbohydrate binding domain comprising the sequence SEQ ID NO: 5, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

The activity of a carbohydrate binding domain may be measured as the affinity of said domain for cellulose, for example using biotinylated glycan binding assay or enzyme-linked assay (Kim et al., Biotechnology and bioprocess engineering 19: 575-580 (2013).

In a particular embodiment, the first polypeptide of the invention comprises the catalytic domain and the carbohydrate domain connected by a linking domain.

The term "linking domain", as used herein, refers to a sequence between domains. Linkers are often composed of flexible residues like glycine and serine so that the adjacent protein domains are free to move relative to one another. Longer linkers are used when it is necessary to ensure that two adjacent domains do not sterically interfere with one another.

In a particular embodiment, the linking domain comprises or consists essentially of or consists of the sequence of SEQ ID NO: 9.

In a particular embodiment, the first polypeptide of the invention further comprises a tag suitable for detection and/or purification located at the N-terminus or at the C-terminus.

The polypeptide can be purified from the medium or from the cell lysate by means of affinity to commercial molecules showing a high affinity for said tags.

The term "tag", as used herein, refers to any amino acid sequence for which specific binding molecules are available, thus allowing the detection/purification of any polypeptide carrying said tag. The tag is generally placed at the amino- or the carboxyl-terminus of the polypeptide. The presence of such tag allows the adapter molecule to be detected using an antibody against the tag polypeptide. Also, the provision of the tag enables the adapter polypeptide to be readily purified by affinity purification using an anti-tag antibody or another type of affinity reagent that binds to the epitope tag.

Suitable detection/purification tags include hexa-histidines (metal chelate moiety), affinity for hexa-hat GST (glutathione S-transferase) glutathione, calmodulin-binding peptide (CBP), streptomycin tag, cellulose-binding domain, maltose-binding protein, S-peptide tag, chitin-binding tag, immunoreactive epitopes, epitope tags, E2tag, HA epitope tag, Myc epitope, FLAG epitope, AU1 and AU5 epitopes, Glu-Glu epitope, KT3 epitope, IRS epitope, Btag epitope, protein kinase-C epitope, VSV epitope or any other tag provided that the tag does not affect the stability of the protein. In a preferred embodiment, the tag is hexa-histidine. Additional tag polypeptides and their respective antibodies are well known in the art. Illustrative, non-limitative examples are poly-histidine-glycine (poly-his-gly) tags; the flu HA tag polypeptide and its antibody 12CA5; the c-myc tag and the 8F9, 3C7, 6E10, G4, B7 and 9E10 antibodies; the Herpes Simplex virus glycoprotein D (gD) tag and its antibody. Other tag polypeptides include tubulin epitope peptide; and the T7 gene 10 protein peptide tag.

Beta-Glucosidase

In another aspect, the invention relates to a polypeptide having beta-glucosidase activity, hereinafter second polypeptide of the invention, comprising a sequence selected from the group consisting of SEQ ID NO: 6, SEQ ID NO: 7 and SEQ ID NO: 8, or a functionally equivalent variant thereof that substantially maintains or improves its catalytic activity.

The term "polypeptide" has been previously defined.

The term "beta-glucosidase" or "cellobiase", as used herein, refers to an enzyme that catalyses the hydrolysis of $\beta(1-4)$ bonds linking two or four glucose or glucose-substituted molecules (i.e., the disaccharide cellobiose or the tetrasaccharide cellotetraose) releasing glucose. It is classified as 3.2.1.21 of the EC number.

The term "beta-glucosidase activity", as used herein, refers to the ability of the beta-glucosidase to cleave or hydrolyse (1-4)-$\beta$-D-glucosidic links from glucose or glucose substituted disaccharides or tetrasaccharides.

In a particular embodiment, the second polypeptide of the invention comprises, consists essentially of or consists of the sequence of SEQ ID NO: 6.

In another particular embodiment, the second polypeptide of the invention comprises, consists essentially of or consists of the sequence of SEQ ID NO: 7.

In another particular embodiment, the second polypeptide of the invention comprises, consists essentially of or consists of the sequence of SEQ ID NO: 8.

In another particular embodiment, the second polypeptide of the invention comprises a functionally equivalent variant of the sequence of SEQ ID NO: 6, SEQ ID NO: 7 or SEQ ID NO: 8 that substantially maintains or improves its catalytic activity.

The term "functionally equivalent variant" has been previously defined.

The particulars of a functionally equivalent variant in terms of sequence identity and previously described in the context of the exoglucanase catalytic domain also apply to the polypeptide having beta-glucosidase activity, with the necessary amendments, as will be immediate for the person skilled in the art.

In particular, the functionally equivalent variant of the sequence with beta-glucosidase activity of SEQ ID NO: 6, SEQ ID NO: 7 or SEQ ID NO: 8 maintains or improves the catalytic activity of the sequence from which it derives.

The term "catalytic activity" and "beta glucosidase activity" has been previously defined.

The beta-glucosidase catalytic activity may be measured by means of a number of techniques assays that are conventional to the skilled person, including assays using various chromogenic and nonchromogenic substrates. Examples of chromogenic substrates include us p-nitrophenol-β-glucoside (pNPG). Examples of nonchromogenic substrate include oligo- or disaccharides (such as cellobiose) where the liberated glucose can be evaluated by the glucose oxidase (GOD) method with a commercial kit.

According to the present invention, the catalytic activity of the sequence of SEQ ID NO: 6, SEQ ID NO: 7 or SEQ ID NO: 8 is substantially maintained if the functionally equivalent has at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the sequence of SEQ ID NO: 6, SEQ ID NO: 7 or SEQ ID NO: 8. Furthermore, the catalytic activity of the sequence of SEQ ID NO: 6, SEQ ID NO: 7 or SEQ ID NO: 8, is substantially improved if the functionally equivalent variant has at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more of the catalytic activity of the sequence of SEQ ID NO: 6, SEQ ID NO: 7 or SEQ ID NO: 8.

In a particular embodiment, the functionally equivalent variant of the sequence of SEQ ID NO: 6, SEQ ID NO: 7 or SEQ ID NO: 8 maintains or improves its catalytic activity at a temperature of at least 0° C., at least 5° C., at least 10° C., at least 15° C., at least 20° C., at least 25° C., at least 30° C., at least 35° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., or higher. Likewise, in another embodiment the functionally equivalent variant of the sequence of SEQ ID NO: 6, SEQ ID NO: 7 or SEQ ID NO: 8 maintains or improves its catalytic activity at pH 0, or at least pH 0.1, or at least pH 0.5, or at least pH 1.0, or at least pH 1.5, or at least pH 2.0, or at least pH 2.5, or at least pH 3.0, or at least pH 3.5, or at least pH 4.0, or at least pH 4.5, or at least pH 5.0, or at least pH 5.5, or at least pH 6.0, or at least pH 6.5, or at least pH 7.0, or at least pH 7.5, or at least pH 8.0, or at least pH 8.5, or at least pH 9.0, or at least pH 9.5, or at least pH 10.0, or at least pH 10.5, or at least pH 11.0, or at least pH 11.5, or at least pH 12.0, or at least pH 12.5, or at least pH 13.0, or at least pH 13.5, or pH 14. All possible combinations of temperatures and pH are also contemplated by the invention.

In particular embodiment, the functionally equivalent variant of the sequence of SEQ ID NO: 6, SEQ ID NO: 7 or SEQ ID NO: 8 that substantially maintains or improves its catalytic activity has at least 70%, at least 80%, at least 90%, at least 95%, or at least 99% sequence identity with SEQ ID NO: 6, SEQ ID NO: 7 or SEQ ID NO: 8.

In a particular embodiment, the functionally equivalent variant of the sequence of SEQ ID NO: 6, SEQ ID NO: 7 or SEQ ID NO: 8 comprises or consists essentially of or consists of the sequence of SEQ ID NO: 10.

In a particular embodiment, the functionally equivalent variant of the exoglucanase catalytic domain comprising the sequence of SEQ ID NO: 1, SEQ ID NO: 2 or SEQ ID NO: 3 does not have the sequence of the catalytic domain of an exoglucanase selected from the group consisting of the exoglucanases shown in the UnitProt database with Accession No. Q9XCD4, W7SI25, R1IFN8, T1V3R1, D2B809, P50900, D9WNN6, B5HJV6, M3C0N9, A0LSI0, F3NPZ3, L1KHJ0, D7C1F6, D9XJA9, M1MJV0, K4QTE6, B5HPK7, D6K6C0, M3ECC0, O82831, S5UZR1, L7EZA5, W7VNI1, A4X938, A9KT91, O65986, R4LQA1, I0BR01, G7VQK6, W6AP62, E0RLD5, W4CUL3 and Q8KKF7.

In a particular embodiment, the second polypeptide of the invention further comprises a tag suitable for detection and/or purification located at the N-terminus or at the C-terminus.

The term "tag", has been previously defined.

Nucleic Acid, Vector and Host Cell

In another aspect, the invention relates to a nucleic acid encoding the first polypeptide of the invention or the second polypeptide of the invention.

The term "nucleic acid", as used herein, relates to a deoxyribonucleotide or ribonucleotide polymer in either single or double stranded form and, unless otherwise limited, encompasses natural nucleotides and analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in an oligonucleotide or in a polynucleotide. A "nucleotide sequence" or "nucleic acid sequence" refers to the sequence of bases in an oligonucleotide or in a polynucleotide.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

In a particular embodiment, the nucleic acid further comprises a sequence encoding a signal peptide fused in frame at the 5' terminus. The term "signal peptide", as used herein, also known as signal, localization signal, localization sequence, transit peptide, leader sequence or leader peptide refers to a short peptide present at the N-terminus of the majority of newly synthesized proteins that are destined towards the secretory pathway. "In frame" or "operatively linked", as used herein, means that the nucleic acid of the invention and the signal peptide are expressed in the correct reading frame under control of the expression control or regulating sequences.

In another aspect, the invention relates to a vector comprising the nucleic acid of the invention.

The term "vector", as used herein, refers to a nucleic acid sequence comprising the necessary sequences so that after transcribing and translating said sequences in a cell the first or second polypeptide of the invention is generated. Said sequence is operably linked to additional segments that provide for its autonomous replication in a host cell of interest. Preferably, the vector is an expression vector, which is defined as a vector, which in addition to the regions of the autonomous replication in a host cell, contains regions operably linked to the nucleic acid of the invention and which are capable of enhancing the expression of the products of the nucleic acid according to the invention. The vectors of the invention can be obtained by means of techniques widely known in the art.

Any vector containing a host-compatible promoter, origin of replication and termination sequences is suitable.

A person skilled in the art will understand that there is no limitation as regards the type of vector which can be used because said vector can be a cloning vector suitable for propagation and for obtaining the polynucleotides or suitable gene constructs or expression vectors in different heterologous organisms suitable for purifying the conjugates. Thus, suitable vectors according to the present invention include prokaryotic expression vectors (e.g. pUC18, pUC19, Bluescript and their derivatives), mp18, mp19, pBR322, pMB9, CoIE1, pCR1, RP4, phages and shuttle vectors (e.g. pSA3 and pAT28), yeast expression vectors (e.g. vectors of the type of 2 micron vectors), integration vectors, YEP vectors, centromeric vectors and the like, insect cell expression vectors (e.g. the pAC series and pVL series vectors), plant expression vectors, such as vectors of expression in plants (e.g. pIBI, pEarleyGate, pAVA, pCAMBIA, pGSA, pGWB, pMDC, pMY, pORE series vectors), and eukaryotic expression vectors based on viral vectors (e.g. adenoviruses, viruses associated to adenoviruses as well as retroviruses and lentiviruses), as well as non-viral vectors (e.g. pSilencer 4.1-CMV (Ambion®, Life Technologies Corp., Carlsbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1).

Vectors may further contain one or more selectable marker sequences suitable for use in the identification of cells which have or have not been transformed or transfected with the vector. Markers include, for example, genes encoding proteins which increase or decrease either resistance or sensitivity to antibiotics or other compounds (e.g. hyg encoding hygromycin resistance), genes which encode enzymes whose activities are detectable by standard assays known in the art (e.g. β-galactosidase or luciferase), and genes which visibly affect the phenotype of transformed or transfected cells, hosts, colonies or plaques such as various fluorescent proteins (e.g. green fluorescent protein, GFP). Alternatively, the vectors of the present invention may carry a non-antibiotic selection marker, including, for instance, genes encoding a catabolic enzyme which enables the growth in medium containing a substrate of said catabolic enzyme as a carbon source. An example of such a catabolic enzyme includes, but is not restricted to, lacYZ encoding lactose uptake and beta-galactosidase. Other selection markers that provide a metabolic advantage in defined media include, but are not restricted to, galTK for galactose utilization, sacPA for sucrose utilization, trePAR for trehalose utilization and xylAB for xylose utilization. Alternatively, the selection can involve the use of antisense mRNA to inhibit a toxic allele, for instance the sacB allele.

In another aspect, the invention relates to a host cell comprising the nucleic acid of the invention or the vector of the invention.

The term "host cell", as used herein, refers to a cell into which a nucleic acid of the invention, such as a polynucleotide or a vector according to the invention, has been introduced and is capable of expressing the polynucleotides of the invention. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Host cells suitable for the expression of the nucleic acid or vector of the invention include, without being limited thereto, cells from bacteria, fungi, plants, insects and mammals. Bacterial cells include, without being limited thereto, cells from Gram-positive bacteria, such as species from the genera *Bacillus, Streptomyces* and *Staphylococcus*, and cells from Gram-negative bacteria, such as cells from the genera *Escherichia* and *Pseudomonas*. Fungi cells preferably include cells from yeasts such as *Saccharomyces, Pichia pastoris* and *Hansenula polymorpha*. Insect cells include, without limitation, *Drosophila* cells and Sf9 cells. Plant cells include, amongst others, cells from cultivated plants, such as cereals, medicinal plants, ornamental plants or bulbs. Mammalian cells suitable for this invention include epithelial cell lines (porcine, etc.), osteosarcoma cell lines (human, etc.), neuroblastoma cell lines (human, etc.), epithelial carcinomas (human, etc.), glial cells (murine, etc.), hepatic cell lines (from monkeys, etc.), CHO (Chinese Hamster Ovary) cells, COS cells, BHK cells, HeLa, 911, AT1080, A549, 293 or PER.C6 cells, human NTERA-2 ECC cells, D3 cells from the mESC line, human embryonary stem cells, such as HS293 and BGV01, SHEF1, SHEF2 and HS181, NIH3T3, 293T, REH and MCF-7 cells, and hMSC cells.

In a preferred embodiment the host cell is a bacterium, more preferably *E. coli*.

Methods for Hydrolysing Cellulose, or Cellobiose and/or Cellotetraose

In another aspect the invention relates to a method for hydrolysing cellulose within a sample containing cellulose to cellobiose and/or cellotetraose, hereinafter first method of the invention, comprising contacting said sample with the first polypeptide of the invention under suitable conditions for hydrolysing cellulose to cellobiose and/or cellotetraose.

The term "cellulose", as used herein, refers to an organic compound with CAS number 9004-34-6, a polysaccharide consisting of a linear chain of several hundred to many thousands of β(1→4) linked D-glucose units.

The term "hydrolysing cellulose to cellobiose and/or cellotetraose", as used herein, refers to the cleavage of chemical bonds of cellulose to release cellobiose and/or cellotetraose.

The term "cellobiose", as used herein relates to a glycosylglucose consisting of two glucose units linked via a β(1→4) bond produced during a metabolic reaction in plants, the kingdom that include flowering plants, conifers and other gymnosperms.

The term "cellotetraose", as used herein relates to a tetrasaccharide comprised of four D-glucose residues connected by β(1→4) linkages.

In a particular embodiment, the sample contains crystalline cellulose.

The term "crystalline cellulose", as used herein, relates to a (1→4)-β-D-glucan (cellulose) in crystalline form with a structure consisting of several hundred to over ten thousand D-glucose residues joined by β(1→4) glycosidic linkages. The crystalline nature of cellulose implies a structural order in which all of the atoms are fixed in discrete positions with respect to one another. An important feature of the crystalline array is that the component molecules of individual microfibrils are packed sufficiently tightly to prevent penetration not only by enzymes but even by small molecules such as water. A skilled person can identify is the cellulose is arranged in a crystalline form, for example by X-ray diffraction data or cystallography. Usually, crystalline cellulose, or MCC, is defined as cellulose with a crystallinity of at least 78%.

The term "sample containing crystalline cellulose" relates to forest biomass and agricultural biomass containing cellulose. Illustrative non-limitative examples of said samples are lignocellulose biomass (composed mainly of cellulose, hemicellulose and lignin), corn stover, *Panicum virgatum* (switchgrass), *Miscanthus* grass species, wood chips and the byproducts of lawn and tree maintenance. Lignocellulosic biomass can be grouped into four main categories: (1) agricultural residues (including corn stover and sugarcane bagasse), (2) dedicated energy crops, (3) wood residues (including sawmill and paper mill discards), and (4) municipal paper waste. Illustrative lignocellulosic biomass sources include, but are not limited to grasses, rice hulls, bagasse, jute, hemp, flax, bamboo, sisal, abaca, straw, corn cobs, corn stover, alfalfa, hay, coconut hair, seaweed, algae.

In a particular embodiment, the method of the method for hydrolysing cellulose to cellobiose and/or cellotetraose comprises using the first polypeptide of the invention further comprising a carbohydrate binding domain.

The term "suitable conditions for hydrolysing cellulose to cellobiose and/or cellotetraose" refers to any conditions under which cellulose can be hydrolysed by an exoglucanase to release cellobiose and/or cellotetraose. Such conditions are known by the skilled person. In a particular embodiment, the sample containing cellulose is chopped into smaller pieces to accelerate the process of enzymatic hydrolysis. As a way of illustrative non-limitative example, the first polypeptide of the invention, preferably further comprising a carbohydrate binding domain, is combined with a sample containing cellulose to form a suspension. The sample containing cellulose-polypeptide suspension is maintained, for example, at a pH of from 5 to 11 and the temperature is maintained within the range of from 25 to 80° C., preferably at least 50° C., at least 60° C., at least 70° C. or at least 80° C. during hydrolysis.

In another aspect, the invention relates to a method for hydrolysing cellobiose and/or cellotetraose within a sample containing cellobiose and/or cellotetraose to glucose, hereinafter second method of the invention, comprising contacting said sample with a polypeptide according to the second under suitable conditions for hydrolysing the cellobiose and/or the cellotetraose to glucose.

The terms "cellobiose" and cellotetraose" have been previously defined.

The term "glucose" or "dextrose", as used herein, refers to a monosaccharide with the molecular formula $C_6H_{12}O_6$. Preferably, the glucose is D-glucose, which is the biologically active stereoisomer.

The term "hydrolysing cellobiose and/or cellotetraose to glucose", as used herein, refers to the cleavage of the chemical bonds of cellobiose and/or cellotetraose to release glucose.

The term "suitable conditions for hydrolysing cellobiose and/or cellotetraose to glucose" refers to any conditions under which cellobiose and/or cellotetraose can be hydrolysed by beta-glucosidase to release glucose. Such conditions are known by the skilled person. As a way of illustrative non-limitative example, the second polypeptide of the invention is combined with a sample containing cellobiose and/or cellotetraose to and maintained, for example, at a pH of from 5 to 11 and the temperature is maintained within the range of from 25 to 80° C., preferably at least 50° C., at least 60° C., at least 70° C. or at least 80° C. during hydrolysis.

In another aspect, the invention relates to the use of the first polypeptide of the invention for hydrolysing cellulose to cellobiose and/or cellotetraose, and to the use of the second polypeptide of the invention for hydrolysing cellobiose and/or cellotetraose to glucose.

The terms "cellulose", hydrolysing cellulose, "cellobiose", "cellotetraose", "glucose" have been defined in connection with the first and second methods of the invention. All the particular embodiments of the first and second methods of the invention apply to these uses.

Enzyme Cocktails and Cellulosome

In another aspect the invention relates to an enzyme cocktail, selected from the group consisting of:
an enzyme cocktail comprising:
(i) the first polypeptide of the invention further comprising a carbohydrate binding domain and
(ii) an endoglucanase and/or a polypeptide having beta-glucosidase activity and
an enzyme cocktail comprising:
(i) the second polypeptide of the invention and
(ii) an endoglucanase and/or a polypeptide having exoglucanase activity.

The term "enzyme cocktail", as used herein, refers to a combination of two or more enzymes. The cellulose cocktail can comprise the microorganism or microorganisms (eg. yeast or other fungi or bacteria) that produce the enzymes and the fermentation products of said microorganism or microorganisms. The enzyme cocktail can comprise the crude fermentation product of the microorganism or microorganisms, that is, the fermentation broth that has been separated from the producing microorganisms and cellular debris. The enzymes of the cocktail can be diluted, concentrated, partially purified, purified and/or dried.

In a particular embodiment, the enzymes of the enzyme cocktail are displayed on a particle (or other surface), or on a microorganism (e.g., on a yeast or other fungus, or a bacteria).

In a particular embodiment, the enzyme cocktail is provided as a cellulosome. The term "cellulosome", as used herein, refers to a multi-enzymatic complex. The cellulosome comprises a scaffoldin (non-catalytic) subunit, dockerins (recognition) modules and a cohesin, and are able to integrate several enzymes. Cellulosomal enzymes contain a catalytic module and a specific dockerin module, which binds to the cohesins of the scaffoldin.

The terms "carbohydrate binding domain" and "polypeptide having beta-glucosidase activity" have been previously defined. All the particular embodiments of said terms previously defined fully apply to the enzyme cocktails of the invention.

The term "endoglucanase" or "endocellulase", as used herein, refers to a type of cellulase that randomly cleaves (1-4)-β-D-glucosidic links in cellulose, lichenin and cereal β-D-glucans, thereby creating new chain ends. Endocellulases also hydrolyse 1,4-linkages in β-D-glucans also containing 1,3-linkages. It has been classified by the Nomenclature Committee of the International Union of Biochemistry and Molecular Biology as EC 3.2.1.4. Endocellulases derived from bacteria have a catalytic domain and a carbohydrate binding module attached by a linker or linking domain.

In a particular embodiment, the endoglucanase comprises a catalytic domain comprising a sequence selected from the group consisting of SEQ ID NO: 11, SEQ ID NO: 12 and SEQ ID NO: 13.

In a particular embodiment, the endoglucanase comprises the carbohydrate binding domain of sequence SEQ ID NO: 14.

In a particular embodiment, the polypeptide having beta-glucosidase activity is the second polypeptide of the invention.

In a particular embodiment, the polypeptide having exoglucanase activity is the first polypeptide of the invention further comprising a carbohydrate binding domain.

In a particular embodiment, the enzyme cocktail comprises:
(i) the first polypeptide of the invention further comprising a carbohydrate binding domain,
(ii) an endoglucanase, preferably an endoglucase comprising a catalytic domain comprising a sequence selected from the group consisting of SEQ ID NO: 11, SEQ ID NO: 12 and SEQ ID NO: 13, and
(iii) a polypeptide having beta-glucosidase activity, preferably the second polypeptide of the invention.

In another particular embodiment, the enzyme cocktail comprises:
(i) the second polypeptide of the invention,
(ii) an endoglucanase, preferably an endoglucanase comprising a catalytic domain comprising a sequence selected from the group consisting of SEQ ID NO: 11, SEQ ID NO: 12 and SEQ ID NO: 13, and
(iii) a polypeptide having exoglucanase activity, preferably the first polypeptide of the invention further comprising a carbohydrate binding domain.

In a more particular embodiment, the enzyme cocktail comprises:
(i) the first polypeptide of the invention further comprising a carbohydrate binding domain,
(ii) the second polypeptide of the invention,
(iii) an endoglucanase, preferably an endoglucanase comprising a catalytic domain comprising a sequence selected from the group consisting of SEQ ID NO: 11, SEQ ID NO: 12 and SEQ ID NO: 13.

In a particular embodiment, the enzyme cocktail further comprises a laccase.

The term "laccase", as used herein, refers to a benzenediol: oxygen oxidoreductase (E.C. 1.10.3.2) that catalyzes the following reaction:

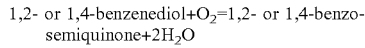

1,2- or 1,4-benzenediol+$O_2$=1,2- or 1,4-benzo-semiquinone+$2H_2O$

The laccase may be any laccase useful in the processes of the present invention. The laccase may include, but is not limited to, an E.C. 1.10.3.2 laccase. Examples of laccases useful in the present invention include, but are not limited to, laccases from *Trametes pubescens, Chaetomium thermophilum, Coprinus cinereus, Coriolus versicolor, Melanocarpus albomyces, Myceliophthora thermophila, Polyporus pinsitus, Pycnoporus cinnabarinus, Rhizoctonia solani, Scytalidium thermophilum*, and *Streptomyces coelicolor*.

In a particular embodiment, the laccase is from *Trametes pubescens*. The term "*Trametes pubescens*", as used herein, refers to a fungus identified in the NCBI database by the Taxonomy ID: 154538.

In a particular embodiment, the enzyme cocktail further comprises a hemicellulase.

The term "hemicellulase", as used herein, refers to one or more enzymes that hydrolyse a hemicellulosic material. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyse glycosidic bonds, or carbohydrate esterases (CEs), which hydrolyse ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure and Appl. Chem. 59: 1739-1752 at a suitable temperature and a suitable pH.

In a particular embodiment, the hemicellulase is a xylanase.

The term "xylanase", as used herein, refers to a 1,4-beta-D-xylan-xylohydrolase (E.C. 3.2.1.8) that catalyses the endohydrolysis of 1,4-beta-D-xylosidic linkages in xylans.

Xylanase activity can be determined with 0.2% AZCL-arabinoxylan as substrate in 0.01 percent TRITON® X-100 and 200 mM sodium phosphate pH 6 at 37° C. One unit of xylanase activity is defined as 1.0 µmol of azurine produced per minute at 37° C., pH 6 from 0.2% AZCL-arabinoxylan as substrate in 200 mM sodium phosphate pH 6.

Xylanases (e.g. endo-beta-xylanases (E.C. 3.2.1.8), which hydrolyse the xylan backbone chain, can be from bacterial sources (e.g., *Bacillus, Streptomyces, Clostridium, Acidothermus, Microtetrapsora* or *Thermonospora*) or from fungal sources (*Aspergillus, Trichoderma, Neurospora, Humi-*

*cola, Penicillium* or *Fusarium* (See, e.g., EP473 545; U.S. Pat. No. 5,612,055; WO 92/06209; and WO 97/20920)). Xylanases useful in the invention include commercial preparations (e.g., MULTIFECT® and FEEDTREAT® Y5 (Danisco Genencor), RONOZYME® WX (Novozymes A/S) Pulpzyme® HC (Novozymes A/S) and NATUGRAIN WHEAT® (BASF). In some embodiments the xylanase is from *Trichoderma reesei* or a variant xylanase from *Trichoderma reesei*, or the inherently thermostable xylanase described in EP1222256B1, as well as other xylanases from *Aspergillus niger, Aspergillus kawachii, Aspergillus tubigensis, Bacillus circulans, Bacillus pumilus, Bacillus subtilis, Neocallimastix patriciarum, Penicillium species, Streptomyces lividans, Streptomyces thermoviolaceus, Thermomonospora fusca, Trichoderma harzianum, Trichoderma reesei* and *Trichoderma viridae*.

In a particular embodiment, the xylanase is from *Trichoderma viridae*. The term "*Trichoderma viridae*", as used herein, refers to a fungus identified in the NCBI database by the Taxonomy ID: 5547.

Method for Hydrolysing Cellulose to Glucose

In another aspect, the invention relates to a method for hydrolysing cellulose to glucose, hereinafter third method of the invention, comprising contacting a sample comprising cellulose with the first or second enzyme cocktail of the invention under suitable conditions for hydrolysing cellulose to glucose, wherein the enzyme cocktail according comprises a polypeptide having exoglucanase activity, an endoglucanase and a polypeptide having beta-glucosidase activity.

The term "hydrolysing cellulose to glucose", as used herein, refers to the cleavage of chemical bonds of cellulose to release glucose.

The terms "cellulose", "glucose", "sample comprising cellulose", "polypeptide having exoglucanase activity", "endoglucanase" and "polypeptide having beta-glucosidase activity" have been previously defined. All the particular embodiments of these terms defined in connection with other aspects of the invention fully apply to the third method of the invention.

The term "suitable conditions for hydrolysing cellulose to glucose", as used herein, refers to any conditions under which cellulose can be hydrolysed by an enzyme cocktail comprising an exoglucanase, an endoglucanase and a beta-glucosidase to release glucose. Such conditions are known by the skilled person. In a particular embodiment, the sample containing cellulose is chopped into smaller pieces to accelerate the process of enzymatic hydrolysis. As a way of illustrative non-limitative example, the enzyme cocktail is combined with a sample containing cellulose to form a suspension. The sample containing cellulose-enzyme cocktail suspension is maintained, for example, at a pH of from 5 to 11 and the temperature is maintained within the range of from 25 to 80° C., preferably at least 50° C., at least 60° C., at least 70° C. or at least 80° C. during hydrolysis. In a particular embodiment, the suitable conditions comprise incubating the sample comprising cellulose and the enzyme cocktail at a pH between 7 and 11.

It is known that the ratio of substrate to enzyme has a significant effect on the reaction rate. Dense suspensions of finely ground cellulose, wherein the solids contents of the substrate in the cellulose suspension comprise 10% to 30% are found to be highly reactive in a system in which the suspension is vigorously agitated in the presence of a highly concentrated (1-2 mg protein/ml) enzyme culture filtrate solution. It is desirable, however, in such a system, to remove the sugar products being formed from the suspension to prevent product inhibition. Such a system works most efficiently if the sugar products being formed are continuously removed.

In certain embodiments the polypeptide according to the invention find utility in compositions for degrading wood pulp into sugars (e.g., for bio-ethanol production), and/or in feed compositions.

For example, the rate of hydrolysis of cellulosic products may be increased by using a transformant expressing one or more copies of the enzymes having greater cellulolytic activity described herein. This permits degradation of products that contain cellulose or heteroglycans at a faster rate and to a greater extent. Products made from cellulose such as paper, cotton, cellulosic diapers and the like can be degraded more efficiently in a landfill. Thus, the product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the polypeptide according to the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

Thus, the enzyme cocktail according to the invention finds use in the hydrolysis of cellulose to its sugar components. In one embodiment, the enzyme cocktail is added to the biomass prior to the addition of a fermentative organism. In a second embodiment, the enzyme cocktail is added to the biomass at the same time as a fermentative organism.

In a particular embodiment, the enzymes of the enzyme cocktail are displayed on a particle (or other surface), or on a microorganism (e.g., on a yeast or other fungus, or a bacteria).

In a particular embodiment, the enzyme cocktail is provided as a cellulosome.

In a particular embodiment, the cellulosic feedstock can be pretreated. Pretreatment may be by elevated temperature and the addition of either of dilute acid, concentrated acid or dilute alkali solution. In certain embodiments the pretreatment solution can be added for a time sufficient to at least partially hydrolyse the hemicellulose components and then neutralized.

In a typical biomass conversion process, enzymatic saccharification can produce sugars that are made available for biological or chemical conversions to other intermediates or end-products. Therefore, the sugars generated from biomass find use in a variety of processes in addition to the generation of ethanol. Non-limiting examples of such conversions are fermentation of glucose to ethanol, and other biological conversions of glucose to 2,5-diketo-D-gluconate (see, e.g. U.S. Pat. No. 6,599,722), lactic acid, succinate, 1,3-propanediol, 2,3-butanediol, the chemical and biological conversions of xylose to xylitol (see, e.g., WO 1998/021339), and the like.

In one embodiment, the cellulose to be hydrolysed is contained in a lignocellulosic material.

The term "lignocellulosic material", as used herein, refers to a material, usually derived from plant biomass, which comprises cellulose, hemicellulose and lignin. The lignocellulosic material can be derived from a single material or a combination of materials and/or can be non-modified and/or modified. Lignocellulosic material can be transgenic (i.e., genetically modified). Lignocellulose is generally found, for example, in the fibers, pulp, stems, leaves, hulls, canes, husks, and/or cobs of plants or fibers, leaves, branches, bark, and/or wood of trees and/or bushes. Examples of lignocellulosic materials include, but are not limited to, agricultural biomass, e.g., farming and/or forestry material and/or residues, branches, bushes, canes, forests, grains, grasses, short rotation woody crops, herbaceous crops, and/or leaves; oil palm fibre waste such as empty fruit bunch and palm trunk; energy crops, e.g., corn, millet, and/or soybeans; energy crop residues; paper mill residues; sawmill residues; municipal paper waste; orchard prunings; Willow coppice and Mallee coppice; wood waste; wood chip, logging waste; forest thinning; short-rotation woody crops; bagasse, such as sugar cane bagasse and/or sorghum bagasse, duckweed; wheat straw; oat straw; rice straw; barley straw; rye straw; flax straw; soy hulls; rice hulls; rice straw; tobacco; corn gluten feed; oat hulls; corn kernel; fiber from kernels; corn stover; corn stalks; corn cobs; corn husks; canola; *miscanthus*; energy cane; prairie grass; gamagrass; foxtail; sugar beet pulp; citrus fruit pulp; seed hulls; lawn clippings; cotton, seaweed; trees; shrubs; wheat; wheat straw; products and/or by-products from wet or dry milling of grains; yard waste; plant and/or tree waste products; herbaceous material and/or crops; forests; fruits; flowers; needles; logs; roots; saplings; shrubs; switch grasses; vegetables; fruit peels; vines; wheat midlings; oat hulls; hard and soft woods; or any combination thereof. In another embodiment, the lignocellulosic material may be the product obtained by a processor selected from the group consisting of a dry grind ethanol production facility, a paper pulping facility, a tree harvesting operation, a sugar cane factory, or any combination thereof.

In a particular embodiment, the enzyme cocktail comprises a laccase. In a more particular embodiment, the lacasse is from *Trametes pubescens*. In a particular embodiment, the enzyme cocktail further comprises a hemicellulasa. In a more particular embodiment, the hemicellulase is a xylanase. In an even more particular embodiment, the xylanase is from *Trichoderma viride*. In a particular embodiment, the enzyme cocktail comprises a laccase, more particularly a laccase from *Trametes pubescens*, and a hemicellulase, more particularly a xylanase, even more particularly a xylanase from *Trichoderma viride*.

In another aspect, the invention relates to the use of the enzyme cocktail of the invention for hydrolysing cellulose to glucose.

Method for Producing Bioethanol

In another aspect, the invention relates to a method for producing bioethanol, hereinafter for method of the invention, comprising
(i) hydrolysing cellulose to glucose following the method for hydrolysing cellulose to glucose of the invention and
(ii) converting the glucose obtained in step (i) to bioethanol in the presence of a yeast capable of producing bioethanol by fermentation of glucose.

The term "bioethanol", as used herein, relates to ethanol with chemical formula is $C_2H_5OH$ produced by fermenting biomass.

In a particular embodiment, the enzymes of the enzyme cocktail are displayed on a particle (or other surface), or on a microorganism (e.g., on a yeast or other fungus, or a bacteria).

In a particular embodiment, the enzyme cocktail is provided as a cellulosome.

The fourth method of the invention comprises a first step of hydrolysing cellulose to glucose following the method of the invention previously defined, that is, using the enzyme cocktail of the invention comprising a polypeptide having exoglucanase activity, an endoglucanase and a polypeptide having beta-glucosidase activity. In a particular embodiment the sample containing cellulose contains crystalline cellulose. In another preferred embodiment, the sample containing crystalline cellulose is chopped into smaller pieces to accelerate the process of enzymatic hydrolysis. In a particular embodiment, the sample containing cellulose to be hydrolysed is contained in a lignocellulosic material.

In a particular embodiment, the enzyme cocktail comprises a laccase. In a more particular embodiment, the laccase is from *Trametes pubescens*. In a particular embodiment, the enzyme cocktail further comprises a hemicellulasa. In a more particular embodiment, the hemicellulase is a xylanase. In an even more particular embodiment, the xylanase is from *Trichoderma viride*. In a particular embodiment, the enzyme cocktail comprises a laccase, more particularly a laccase from *Trametes pubescens*, and a hemicellulase, more particularly a xylanase, even more particularly a xylanase from *Trichoderma viride*.

Step (ii) comprises converting the glucose obtained in step (i) to bioethanol in the presence of a yeast capable of producing bioethanol by fermentation of glucose. In a preferred embodiment, the glucose obtained in step (i) is removed from the solution. The term "yeast", as used herein relates to a eukaryotic microorganisms classified as members of the fungus kingdom. Yeasts are unicellular, although some species may also develop multicellular characteristics by forming strings of connected budding cells known as pseudohyphae or false hyphae. In a preferred embodiment, the yeast capable of producing bioethanol by fermentation of glucose is *Saccharomyces cerevisiae*.

It is also contemplated in the invention, that some enzymes of the enzyme cocktail are expressed by the yeast capable of producing bioethanol by fermentation of glucose. As a way of illustrative-non limitative example the *S. cerevisae* transformant carrying the BGL1 (β-glucosidase gene) is capable of fermenting cellobiose to ethanol (Marchida M I et al, 1998 Appl. Environ. Microbiol. 54:3147-3155).

In a particular embodiment, the method for producing bioethanol further comprises a step (iii) comprising distilling or dehydrating the bioethanol obtained in step (ii). The term "distilling", as used herein relates to a method to separate two liquid utilizing their different boiling points, in present case removing of water from bioethanol. The term "dehydration", as used herein relates to a purification method, a physical absorption process using a molecular sieve, for example, ZEOCHEM Z3-03 (a special 3A molecular sieve for ethanol dehydration).

In a preferred embodiment, the method further comprises distilling the bioethanol from resulting liquid by boiling the water off and collecting the bioethanol in a separate tank. In another preferred embodiment, to distil pure bioethanol, benzene or cyclohexane may be added to the mixture. These chemicals bind to and remove the last small bits of water from the distillate.

The invention will be described by way of the following examples which are to be considered as merely illustrative and not limitative of the scope of the invention.

Examples

Materials and Methods
Cloning of Commercial Plasmid

Cellulases encoding genes were codon optimized for *E. coli* and purchased in a commercial plasmid (Life Technologies). This plasmid contains an antibiotic resistance gene for the proper selection. This antibiotic was carbenicillin for all the genes but for the exoglucanase one that was kanamycin. The antibiotic ensures the proper selection of bacteria, being the only *E. coli* colony grown in the plate. 1 µL of the commercial plasmid (50 ng/µL) was transformed into *E. coli*-XL1Blue competent cells (Agilent Technologies) following the manufacturer's protocol. Once transformation was performed, competent cells were grown in 400 µL of SOC medium (Invitrogen) for one hour and spread in LB-agar-antibiotic (the selected one in each case) plates and incubated overnight at 37° C.

Single colonies were isolated and grown in 10 mL of LB media+1% 100 mg/mL kanamycin for 16 h at 37° C. gently stirring. The harvesting of cells was made by centrifugation (14000 rpm, 10 min, 4° C., Eppendorf Centrifuge 5810R) and plasmids were extracted using a so called miniprep kit, DNA-plasmid extraction kit (Thermo Scientific) following the company's protocol. Purified plasmids were eluted in 50 µl of nuclease-free water and their concentration was measured in the Nanodrop 2000L system.

Digestion of Commercial Plasmid

The enzymatic digestion of the commercial plasmid containing the cellulase gene was carried out after amplification. In order to perform the enzymatic digestion, a double digestion strategy with BamHI-KpnI cutting was used. BamHI and KpnI restriction sites are flanking the borders of the cellulase gene.

The enzymes used for the digestions were purchased from Thermo Scientific and the protocol used was the manufacturer's Fast Digest protocol. The final digestion volume is adjusted to 50 µL and incubated at 37° C. for one hour. The screening of the digestion products was made in a DNA-agarose gel (1%) in TAE buffer. The running of the DNA-agarose gel was carried out using the BioRad agarose electrophoresis equipment for approximately 90 min. After this time, the band corresponding to the cellulase was extracted from the gel and the gene was purified with a DNA-extraction kit from Thermo Scientific following the usual protocol. Concentrations were also measured using the Nanodrop 2000L.

The host used for the insert was pQE80 plasmid.
pQE80-Cellulase Construct Ligation Once the digestion is made and the gene purified, the genes encoding the cellulase were ligated onto a high-efficiency bacterial expression vector with compatible cohesive ends. The previously digested BamHI-pQE80-KpnI open plasmid was used. This plasmid was a kind gift from Professor Julio Fernandez's lab at Columbia University. It also contains an ampicillin resistance gene. For the ligation of the gene encoding cellulase and the pQE80 plasmid Invitrogen's T4-DNA ligase protocol was used. The mol ratio between the amount of plasmid vector and the cellulase gene insert is 3:1. With the following formula, the calculations for the needed amount of plasmid and DNA inserts were done. Ligations were incubated overnight at room temperature. Thereafter, to stop the process, ligations were diluted 5 times with deionized water.

Cloning of pQE80-Cellulase Plasmid

5 µL of the recombinant plasmid (depending on the concentration) were transformed into *E. coli*-XL1Blue competent cells following the same protocol described above. Competent cells are later spread out onto LB-agar-ampicillin plates and incubated overnight at 37° C. In the same way previously described, single colonies were taken out and grown in 10 mL of LB media+0.1% 100 mg/mL ampicillin for 16 h at 37° C. Finally, cells were harvested by centrifugation (14000 rpm, 10 min, 4° C.) and plasmids were extracted using the same so called miniprep kit, DNA plasmid extraction kit. The purified plasmids were eluted in 50 µl nuclease-free water and their concentration was measured in the Nanodrop 2000L. The plasmids are screened and verified in a DNA-agarose (1%) gel and concentration is calculated using the Nanodrop 2000L system.

Screening

Once the pQE80-cellulase constructions were made and amplified, an amount between 1-10 µL of the plasmid was transformed onto *E. coli*-BL21 competent cells following the seller protocol. After transformation, cells were grown as previously was made with EColi-Xl1blue in 400 µL of SOC medium for 1 hour at 37° C. and spread out in LB-agar plates with the corresponding antibiotic. Plates were incubated overnight at 37° C. to grow the colonies. Some single colonies were isolated and grown in 10 mL LB medium+ antibiotic for 8 hours or until the optical density (OD) of the medium reached 0.6. ODs were measured with the Nanodrop 2000L.

In order to induce the overexpression of cellulases by T7 promoter activation, 5 of IPTG (isopropyl-β-D-thiogalactopyranosid, Sigma Aldrich) 100 mg/mL was added to the half of the volume of medium and the solution was incubated overnight at 37° C. 1 mL of each colony was taken then, to screen the overexpression. Bacteria were harvested by centrifugation (14000 rpm, 10 min, 20° C.). Supernatant was discarded and bacteria were resuspended in 20 µL of extraction buffer. 20 µL of 2×SDS page Sample Buffer solution was added to each sample for the denaturation and charging of the protein in acrylamide electrophoresis gel separation. The samples were again centrifuged (14000 rpm, 30 min 20° C.) and boiled at 95° C. for 3 min.

The screening was carried out by running 20 µL of each of the solutions are run in an 8-12% acrylamide gel for approximately 1 hour in a BioRad acrylamide electrophoresis system. 12% gel has been used in the case of endoglucanase as it size is 33 kDa. However in the case of exoglucanase 70 kDa and beta-glucosidase 82 kDa, 8% acrylamide gel has been used After the run, gels were cleaned in deionized water for 30 min. Proteins in the gel were stained with Bradford solution (Thermo Scientific) for 20 min and cleaned with deionized water again. Negative controls without IPTG are also added to the gel to visualize the overexpression better.

Protein Production

The best overexpressed colony was selected and 1 mL of LB media with the desired bacteria was added to 1 L more LB media+0.1% 100 mg/mL of the corresponding antibiotic+0.1% 50 mg/mL chloramphenicol (it was added to maintain the ability of overexpression of the bacterial pLys system). The culture was incubated for about 8 h until OD>0.6 at 37° C. shaking (250 rpm). Once the desired OD was reached, 0.1% 100 mg/mL IPTG was added to induce the overexpression of the protein. The culture was again incubated overnight (16 h more or less) at 37° C. while shaking.

After doing this, bacteria were separated from the media by centrifugation (4000 rpm, 4° C., 20 min) and the supernatant discarded. The pellet was then resuspendend in 16 mL of extraction buffer and 160 µL of protease inhibitor (Merck Millipore) was added and incubated rocking (5 rpm) for 30 min at 4° C. with 160 µL of 100 mg/mL lysozyme (Thermo Scientific) solution for the enzymatic destabilization of the bacterial membrane. Once this was done, a series of reactives are added: 1.6 mL of 10% Triton X-100 (Sigma Aldrich) for the chemical destabilization of the bacterial membrane; 80 of 11 mg/mL DNAse I (Invitrogen) for the enzymatic degradation of DNA; 80 µL of 1 mg/mL RNAse A (Ambion) for the enzymatic degradation of RNA; 160 µL of 1M $MgCl_2$ (Sigma Aldrich) as a catalyzer to increase the enzymatic activity of DNAse and RNAse. The suspension was incubated again for 10 min at 4° C. with rocking prior to the cell lysis. Cell lysis was carried out by French press (G. Heinemann HTU DIGI-F Press). Cells were introduced in the press chamber and lysed at 18000 psi during 30 min. The lysis product obtained was then centrifuged in a high-speed centrifugation system (33000 rpm, 4° C., 90 min; Beckman Coulter Avanti J-26 XPI).

Ancestral Endoglucanase Purification

The purification of ancestral endoglucanase was carried out first by temperature and then using a HisTrap column. After 30 minutes of centrifugation, the supernatant was transferred to a 50 ml tube and it was incubated in a water bath at 50° C. for 20 min. Then, the sample was cooled in ice for 5 min and centrifuged to eliminate debris at 4000×g for 10 min.

After the temperature step, the second step was carried out with the HisTrap cobalt affinity resin (Thermo Scientific). All the cellulase constructs contain a HisTag composed of 6 consecutive histidines in the N terminus of the construct which poses the ability to specifically bind to the cobalt affinity column. This binding was later eluted by adding imidazol in the buffer. A 150 mM imidazole buffer was used for the elution.

Ancestral Exoglucanase Purification

For exoglucanase, the first purification process was carried out by means of a HisTrap nickel affinity resin (Thermo Scientific). In this case, niquel one was used, as the exoglucanase is harder to purify. The niquel resin has a stronger affinity but it is not as specific as the cobalt one is. This binding can was later eluted by adding imidazol in the buffer. A 150 mM imidazole buffer was used for the elution.

The second purificiation process used was by means of size exclusion and it was carried out with an AKTA pure fast protein liquid chromatography (FPLC) system (GE Healthcare) with a Superdex 200 column of 30 cm (GE Healthcare). Fractions of interest were collected from the chromatogram and stored in Acetate buffer 50 mM (pH 5.5).

Ancestral Beta-Glucosidase Purification

In the case of beta-glucosidase, the same process was used with some changes. In the first purification process instead of using niquel resin, cobalt resin was used.

Regarding to the second purification process, the buffer used for the elution in the size exclusion process was PBS (pH7).

Extant T. maritima Purification

The extant T. maritima was purified in the same way of the ancestral endoglucanase, both for the first purification step and for the second purification step.

T. reesei Cocktail Protein Determination

The determination of the protein content of the cocktail was first made by the dry weight method (Nozaki, Y., Arch Biochem Biophys, 1986. 249(2): 437-46) for protein content determination. For that porpoise size exclusion chromatography was used, using a Superdex 200HR column, eluted in water. Then the sample was freeze dried and it was weighted. Second, absorbance at 280 was measured of a purified fraction and used densitometry and mass spectrometry for determining concentration of endoglucanase. Moreover, the protein concentration was determined by the BCA assay (Pierce) using a BSA standard supplied with the kit and a standard of our ancestral endoglucanase LFCA.

CMC

This assay is specific for measuring the endoglucanases activity. Endo-b-1,4-D-glucanase (EC 3.2.1.4) randomly cleaves accessible intermolecular b-1,4-glucosidic bonds on the surface of cellulose. Water-soluble derivatives of cellulose such as carboxymethylcellulose (CMC) and hydroxyethylcellulose (HEC) are commonly used for endoglucanase activity assays because insoluble cellulose has very low accessible fractionation of b-glucosidase bonds to cellulase. The reaction of hydrolysis can be determined in different ways: by measuring the changes in reducing sugars, viscosity or color but the assay recommended for the endoglucanase (CMCase) assay is a fixed conversion method. This method requires 0.5 mg of absolute glucose released under the reaction condition. The reducing sugars concentration is finally measured by the DNS method (Miller, G. L., Anal Chem, 1959. 31: 426-428).

Cellulolytic activity of ancestral endoglucanase (LFCA) was tested at 50 mM and pH 4.8 citrate buffer with 2% CMC (Sigma), 30 min at various incubation temperatures. Cellulases from T. maritima and T. reesei (1,4-(1,3:1,4)-β-D-Glucan 4-glucano-hydrolase (EC 3.2.1.4), C2730 Sigma Aldrich) were used as controls. In addition two blanks were also prepared; the substrate blank (0.5 ml of CMC solution+0.5 ml of citrate buffer) and the enzyme blank (0.5 ml of CMC solution+0.5 ml of dilute enzyme solution). Both the substrate and enzyme blanks were treated identically as the experimental tubes. Enzymatic reactions were terminated by placing the tubes into an ice-water bath. Enzymatic activity was determined quantitatively by measuring soluble reducing sugars released from the cellulosic substrate by the dinitrosalicylic acid (DNS) method. A volume of 3 ml of the DNS solution was added to each sample and the reaction mixtures were boiled for 5 min. After boiling, tubes were cooled and after adding 20 ml of distilled water, absorbance was measured at 540 nm.

A glucose standard curve was used to determine the concentration of the released reducing sugars. For this purpose, the following standards were prepared: GS1—0.125 ml of 2 mg/ml glucose+0.875 ml of buffer. GS2—0.250 ml of 2 mg/ml glucose+0.750 ml of buffer. GS3—0.330 ml of 2 mg/ml glucose+0.670 ml of buffer. GS4—0.500 ml of 2 mg/ml glucose+0.500 ml of buffer. The glucose released by the enzyme solutions was calculated with deduction of the enzyme blank absorbance based on the glucose standard curve.

The determination of the pH dependence was done as following: purified enzymes were diluted in 50 mM buffer at different pH values between 4 and 12. Activities were measured with 2% CMC at 70° C. for 30 min. All assays were performed in triplicate and the average value with standard deviation was determined.

Residual and Long-Term Activity Measurements

On the one hand the determination of the residual activity was carried out to determine when the enzyme loses half of its activity. The enzymes diluted in citrate buffer 50 mM at their optimum pH, were incubated at different temperatures (60-90° C.). The residual activity was measured on 2% CMC for 30 min at 60° C. The amount of reducing sugars was measured and quantified by the DNS method. The parameter T50 is defined as the temperature at which an enzyme loses 50% of its optimal activity after a 30 min heat treatment.

On the other hand, a study of the activity of the enzymes in different times was done, the long-term activity. In this case, all measurements were conducted in 50 mM citrate buffer, pH 4.8 on 2% CMC at 60° C. for a period of 10 to 240 minutes. After hydrolysis, the reducing sugar concentration was measured by the DNS method.

Inactivation Constant (Kin) Determination

The objective of this assay was the determination of the inactivation constant, for this purpose, enzymes were incubated at 80° C. during different time intervals diluted in their optimum pH. The amount of reducing sugar was measured and quantified by the DNS method. The inactivation constant ($K_{in}$) was calculated using the equation log (% residual activity)=2.303×$K_{in}$×t, where t is time [11]. The half-lives of the enzymes were calculated from the plot.

CellG3

Endoglucanase activity was also measured using another different method, the CellG3 method of an endoglucanase assay kit (K-CellG3, Megazyme International, Ireland). As controls, cellulases from *T. maritima* and *T. reesei* (C2730, Sigma Aldrich) were used. Enzyme samples were diluted in acetate buffer (100 mM, pH 4.5) and after the addition of CellG3 substrate enzyme solutions were incubated at different pH's and temperatures. The incubation was carried out for 10 min. Cellulase cleaved a bond within BC1PNPβ-G3, the non-blocked reaction product containing the 2-chloro-4-nitrophenyl substituent was instantly cleaved to D-glucose and free 2-Cl-4-nitrophenol (ClPNP). Finally, the hydrolysis reaction was stopped by addition of Trizma base solution (pH 9) and the Cl-phenolate color was developed and measured at 400 nm (NanoDrop 2000C). CellG3 Unit was defined as the amount of enzyme required to release one micromole of 2-chloro-4-nitrophenol from CellG3 in one minute under the defined assay conditions, the enzyme activity was calculated multiplying the measured absorbance at 400 nm by 9.64 and by the dilution factor [146].

Filter-Paper

In this case, this assay was used for the determination of a total cellulase system made of three cellulases: endoglucanases, exoglucanases, and b-glucosidases. Total cellulase activities were measured using insoluble substrates, including pure cellulosic substrates such as Whatman No. 1 filter paper or any other lignocellulosic substrate. Filter-paper assay FPA is the most common total cellulase activity assay recommended by IUPAC. The assay is based on a fixed conversion degree, measures the hydrolysis of both, crystalline and amorphous cellulose of the filter paper. In this case, the activity of the total cellulase is described in terms of filter-paper units (FPU).

The filter paper activity (FPA) of cellulase enzymes was carried out in a mixture containing 0.5 mL diluted enzyme by 50 mM citrate buffer (pH 4.8) and 50 mg of Whatman No. 1 filter paper and incubated at various temperatures for 1 h. CellicCTec2 (Novozymes) enzyme cocktail was used as a control. Apart from the reactions, three blanks were also prepared: Reagent blank (1.5 ml of 50 mM citrate buffer) enzyme blank (1.0 ml of 50 mM citrate buffer+0.5 ml enzyme dilution) and substrate blank (1.5 ml of 50 mM citrate buffer+filter paper strip). All the blanks were treated identically as the experimental tubes. The reaction was finished placing the tubes on ice. The reducing sugars released were determined using the DNS method. 3 ml of DNS was added to all the tubes and after boiling for 5 min they were placed on ice again to stop the reaction. 0.5 ml of the colored solutions were withdrawn into 1.5-ml microcentrifuge tubes and centrifuged at 10000 g for 3 min. Finally, 2.5 ml of distilled water was added to 0.2 ml of the supernatant and the absorbance was measured at 540 nm, where the absorbance of reagent blank was used as the blank.

In order to determine the released reducing sugars a standard curve was made by means of preparing the following standards: GS1: 1.0 ml of glucose standard+4.0 ml buffer=2 mg/ml (1.0 mg/0.5 ml). GS2: 1.0 ml of glucose standard+2.0 ml buffer=3.3 mg/ml (1.65 mg/0.5 ml). GS3: 1.0 ml of glucose standard+1.0 ml buffer=5 mg/ml (2.5 mg/0.5 ml). GS4: 1.0 ml of glucose standard+0.5 ml buffer=6.7 mg/ml (3.35 mg/0.5 ml). Add 0.5 ml of GS1-4 solutions to 13×100 mm test tubes, and add 1.0 ml of 0.050 M citrate buffer.

Filter paper unit (FPU) is defined as 0.37 divided by the amount of enzyme that produces 2.0 mg glucose equivalents in 1 h from 50 mg of filter paper. All experiments were carried out in triplicates.

Lignocellulosic Substrates Hydrolysis

The protocol used for this assay was the same that the one for filter paper, the only difference is the substrate. But not only this, we have also added more cellulolytic enzymes such as laccase and xylanase. 50 mg of different lignocellulosic substrates in 50 mM citrate buffer at pH 4.8 were used. Enzyme hydrolysis was performed for 1 hour at 50° C. Endoglucanase alone or in combination with Laccase and Xylanase were used for hydrolysis of the lignocellulosic material. Three different enzyme combinations were used differing in the endoglucanase used: ancestral, *T. maritima* or *T. reesei*. Cellulose degradation was determined by determining percentage of hydrolysis as described elsewhere (Van Dyk, J. S. P. and Pletsckle, B. I,. Biotechnol Adv 2012. 30: 1458-1480).

Avicel

In this case, a crystalline substrate was used for the cellulolytic activity with mixtures of the free enzymes (0.5 µM each) at 0.5 µM buffer acetate (50 mM final concentration) with 1% Avicel (FMC, Delaware USA) at various temperatures and pH's for 24 hours. 0.4 ml of the enzymes solutions was placed together with 1.6 ml of Avicel solution. Also two blank were done: a substrate blank (1.6 ml of Avicel solution+0.4 ml of acetate buffer) and an enzyme blank (1.6 ml of acetate buffer+0.4 ml of enzyme solution). Enzymatic reactions were stopped by placing the tubes into an ice-water bath, and the tubes were then be centrifuged for 2 min at 14,000 rpm at room temperature. Enzymatic activity was determined quantitatively by measuring soluble reducing sugars released from the cellulosic substrate by the dinitrosalicylic acid (DNS) method. A volume of 150 µL of the DNS solution was added to 100 µL of sample (supernatant fluids), and after boiling the reaction mixture for 10 min, absorbance at 540 nm was measured. Released sugar concentrations were determined using a glucose standard curve. Glucose concentration was determined using a glucose assay kit [150](GOD; Sigma-Aldrich) according to the manufacturer's instructions. All assays were performed at least twice in triplicate.

Thermal Stability of the Ancestral Endoglucanase: Circular Dichroism

The thermal stability of the ancestral endoglucanase was determined by Circular dichroism (CD); measurements were made with a JASCO J-815 CD spectrophotometer. For each construct, spectra were generated by averaging five wavelength scans. Thermal unfolding transitions were monitored at 222 nm, with a 0.5° C. step size, within the range of 55 to 110° C., in a thermal-resistant 10-mm quartz cuvette. Thermal denaturations at pH 4.8 were carried out in 50 mM citrate buffer both with 0.5M Glycerol and without glycerol.

Ancestral Endoglucanases Kinetic Parameters Determination

In order to determine the kinetics parameters of the ancestral endoglucanase, Km and Vmax, ten different substrate concentrations were used in the range of 2 to 20 mg/ml CMC for endoglucanase. The Km and Vmax were determined directly from the hyperbolic curve fitting of Michaelis-Menten equation generated using Phyton inhouse script. Kcat was determined by the formula Vmax/Et, where Et is the total enzyme concentration in μmol/ml.

Results

Ancestral Enzyme Cocktail

The ancestral enzyme cocktail comprises the following enzymes:
 exoglucanase having a catalytic domain of SEQ ID NO: 2
 beta-glucosidase of SEQ ID NO: 7
 endoglucosidase having a catalytic domain of SEQ ID NO: 11
 laccase from *Trametes pubescens*
 xylanase from *Trichoderma viride*

The specific activity of the ancestral cocktail against a commercial one Ctec2 cocktail was measured (FIG. 1). The assay was run in three different temperatures 50° C. (FIG. 1a), 60° C. (FIG. 1b) and 70° C. (FIG. 1c) and in three different pH values (5, 7 and 11) in each case. As the figure shows, the ancestral cocktail outperforms the commercial cocktail Ctec2 in all the cases (FIG. 1). This significant difference in the activity is even bigger in the case of the neutral and the basic pH (FIGS. 1b and 1c), where the activity of the commercial cocktail is really small.

Once the good performance of the ancestral cocktail in comparison with the commercial one Ctec2 was measured, a study of the stability was carried out.

Figure 2:
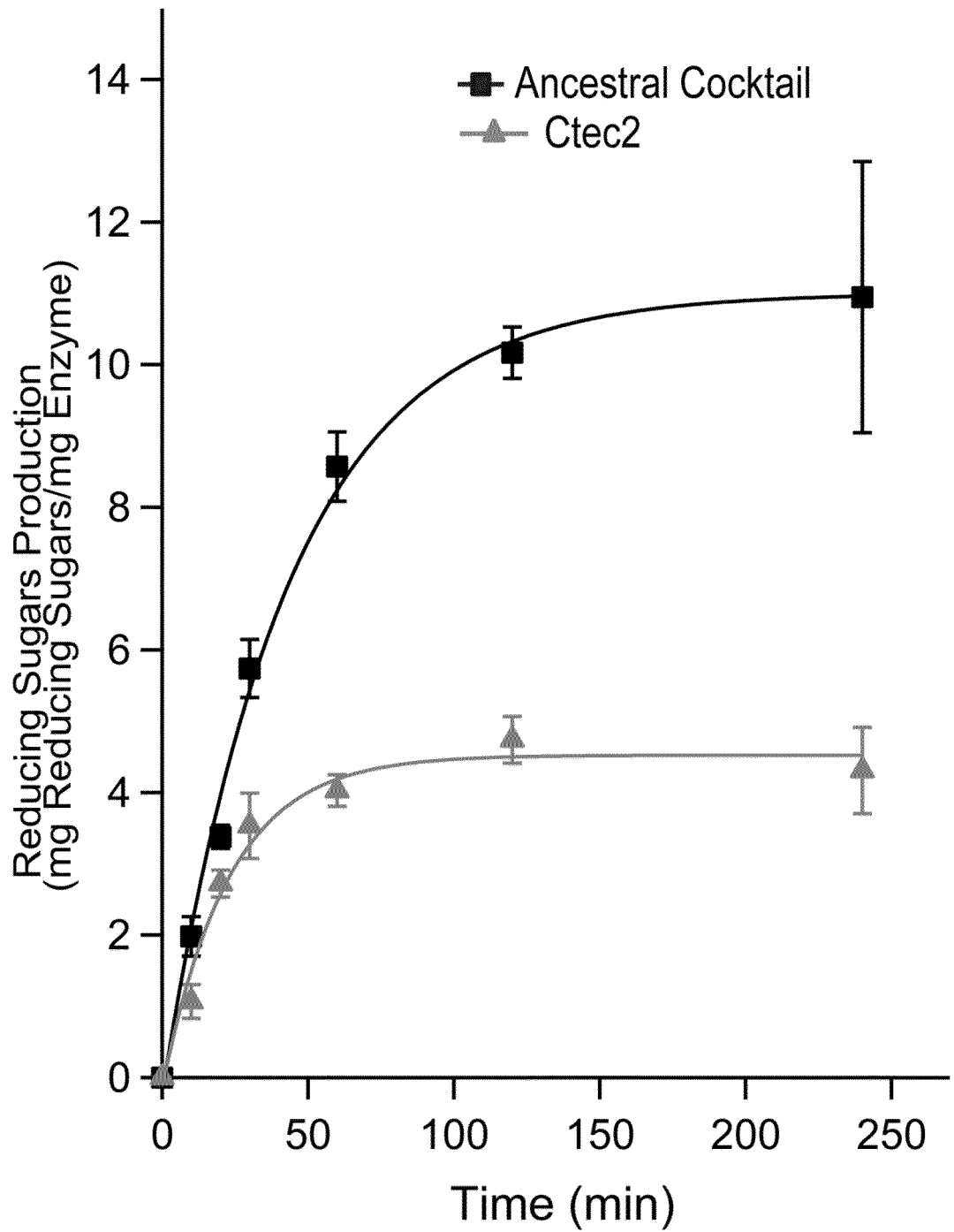
FIG. 2. Long-time activity measurements for ancestral and commercial enzyme cocktail Ctec2. Reducing sugars production was measured at different reaction times at 60° C. Experimental details are provided in the Materials and Methods. In each case, three replicates were collected. The average±S. D. values are shown for each measurement.

The long term activity of both cocktails (ancestral cocktail and Ctec2 commercial cocktail) was determined measuring the activity at 60° C. and reaction times ranging from 10 to 250 min as shown in FIG. 2. In this figure, it can be seen that the commercial cocktail Ctec2 reached almost the 100% of the reducing sugar production in a short time comparing with the ancestral cocktail. The plot shows (FIG. 2) that the commercial cocktail reaches the 100% of its reducing sugar production in 50 minutes; in contrast, the ancestral one needs 250 minutes to reach it. However, the production of reducing sugars of the ancestral cocktail is higher than the commercial one from the very beginning.

From this plot (FIG. 2) the hydrolysis rate of both cocktails was calculated. A value of 0.14 μg of sugar per minute was obtained in the case of the ancestral cocktail and a rate of 0.067 μg of sugar per minute for the commercial one Ctec2.

Figure 3:
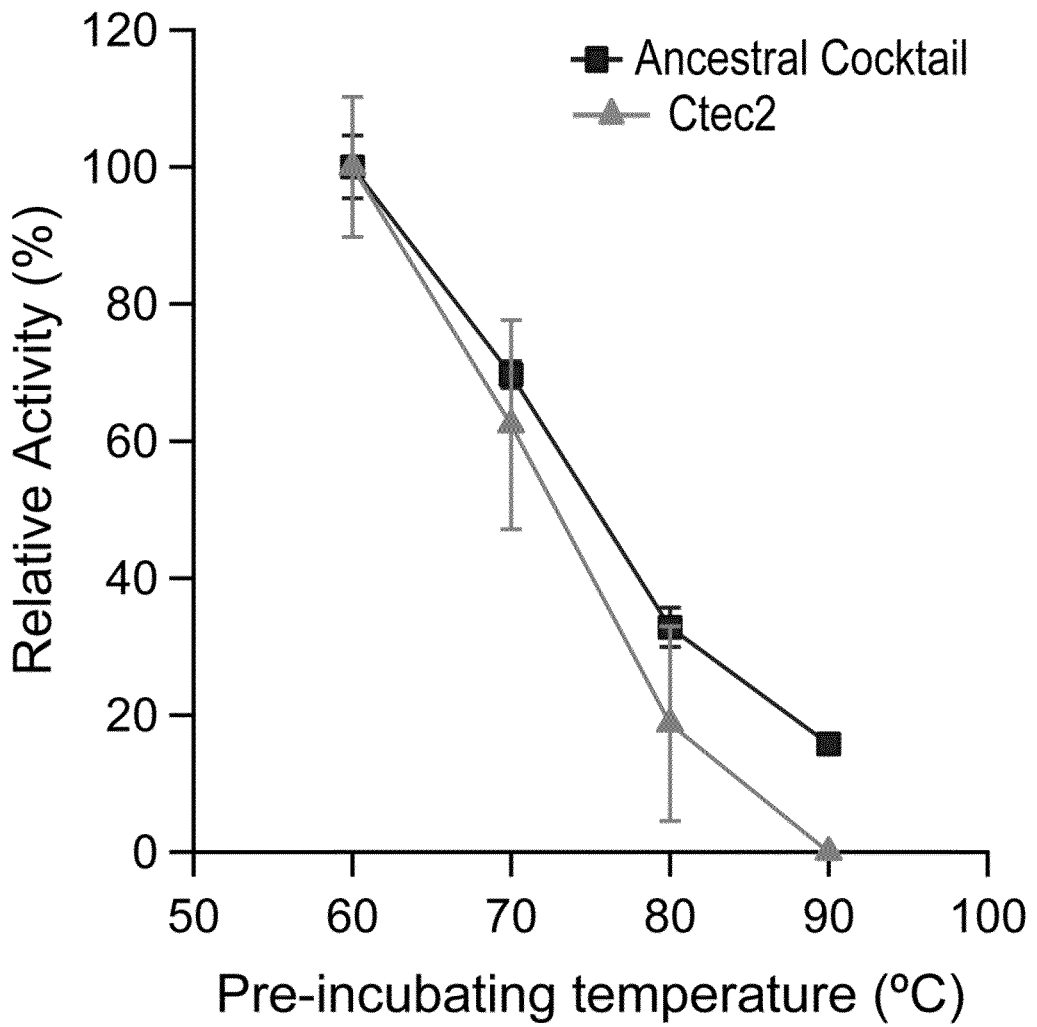
FIG. 3. Pre-incubation experiments for ancestral and commercial enzyme cocktail Ctec2 at different temperatures conducted for 30 min. Residual activity was determined on 2% CMC for 30 min at 60° C. using DNS. Relative activity is determined for each individual enzyme. Each enzyme was pre-incubated at its best performing pH value. All assays were triplicated. Values are reported as average±S.D.

In addition, the stability for temperature incubation was calculated. This study is shown in FIG. 3 making the comparison of the stability of the ancestral cocktail versus the commercial one Ctec2. By means of this graphic representation, the temperature at which they lost half of their activity after 30 min of incubation was determined, making after the measurement of the activity at 60° C. The estimated values of temperature where the commercial Ctec2 and the ancestral cocktail lose half of their activity were 73° C. and 76° C. for each case (FIG. 3).

Figure 4:
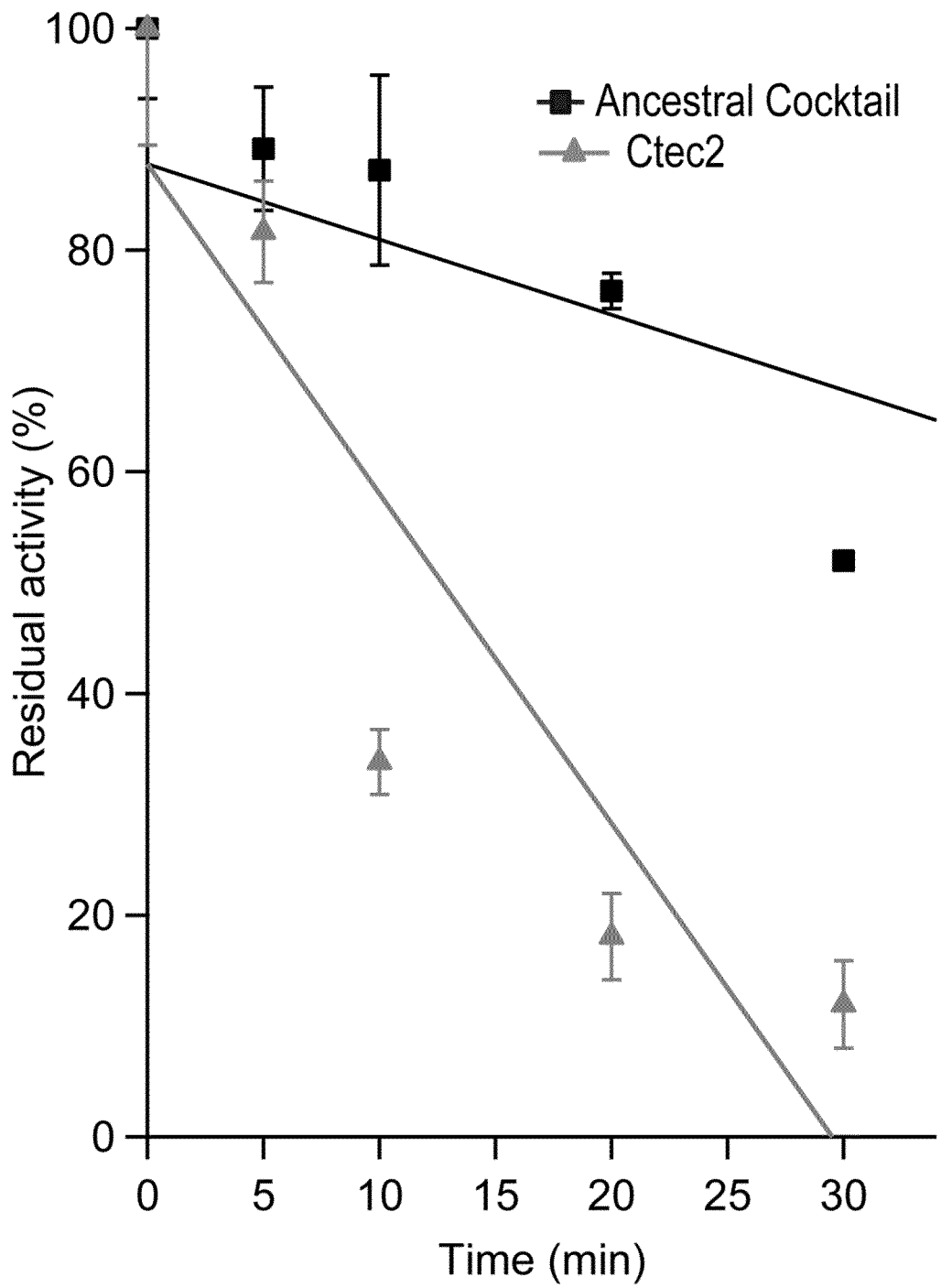
FIG. 4. Ancestral and commercial enzyme cocktail Ctec2 inactivation at 80° C. (a) Residual activities were measured at different incubation times. (b) Specific activity was determined after incubation. The activity of non-incubated enzyme was used as a reference for 100% residual activity. Each assay was repeated five times. The values are presented as an average±S.D. All assays were triplicated. Values are reported as average±S.D.

Continuing with the thermal stability of the enzyme cocktails, the kinetics for the thermal inactivation of the enzymes at 80° C. was determined. The residual activity plotted against the time followed a clear first order kinetics for both ancestral and commercial cocktail Ctec2 (FIG. 4).

The inactivation constant ($K_{in}$) and half-life ($t_{1/2}$) was calculated from the plot. The half-life for ancestral and commercial cocktails Ctec2 at 80° C. was 55 and 13 min, respectively (Table 1).

TABLE 1

Thermodynamic constants of reconstructed ancestral endoglucanase.

| Enzyme | Endoglucanase | Endoglucanase + %0.5 Glycerol |
|---|---|---|
| Tm (° C.) | 80.3 | 83.3 |
| ΔH (kJ/mol) | 592 | 428 |
| ΔS (kJ/mol/K) | 1.68 | 1.20 |
| Cp (kJ/mol/K) | $9.8 * 10^{-6}$ | $5.5 * 10^{-5}$ |

The values obtained in this case were similar to the previous ones, what makes sense. In the case of the commercial cocktail, we obtained a slightly higher value than for *T. reesei* but similar in magnitude. In the case of the ancestral cocktail is almost the same it was measured for the ancestral endoglucanase. Regarding to $K_{in}$, the values also are similar to that previously obtained, 0.39 in the case of ancestral cocktail and 1.72 in the case of the commercial one.

Figure 5:
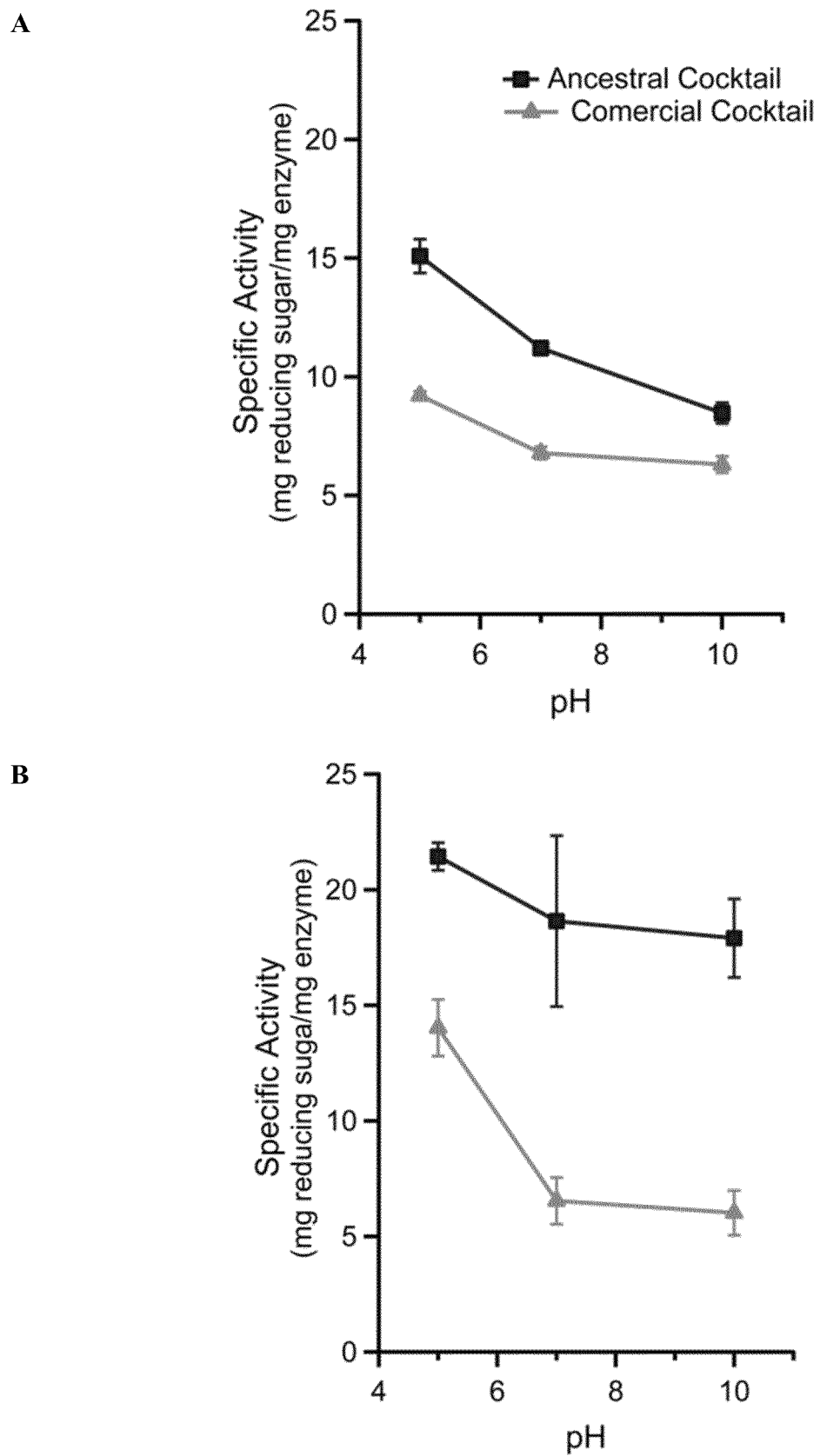
FIG. 5. Ancestral and commercial enzyme cocktail Ctec2 activity measurements using avicel. Specific activity assay at pH (5, 7, 10) for ancestral and commercial cocktail at different temperatures. a) 40° C., b) 50° C., c) 60° C. and d) 70° C. We determined the reducing sugar mg equivalent released per minute and per mg of enzyme. All assays were triplicated. Values are reported as average±S.D.
Figure 5:
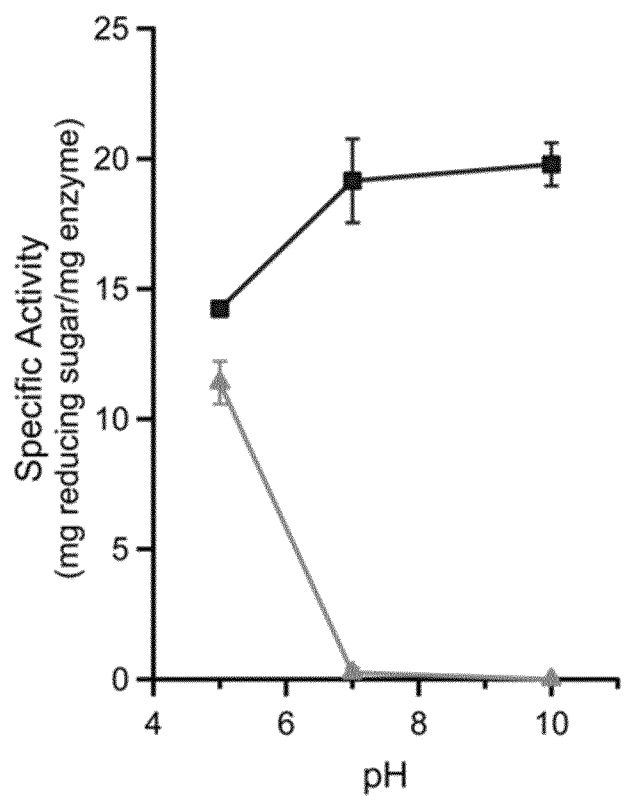
Figure 5:
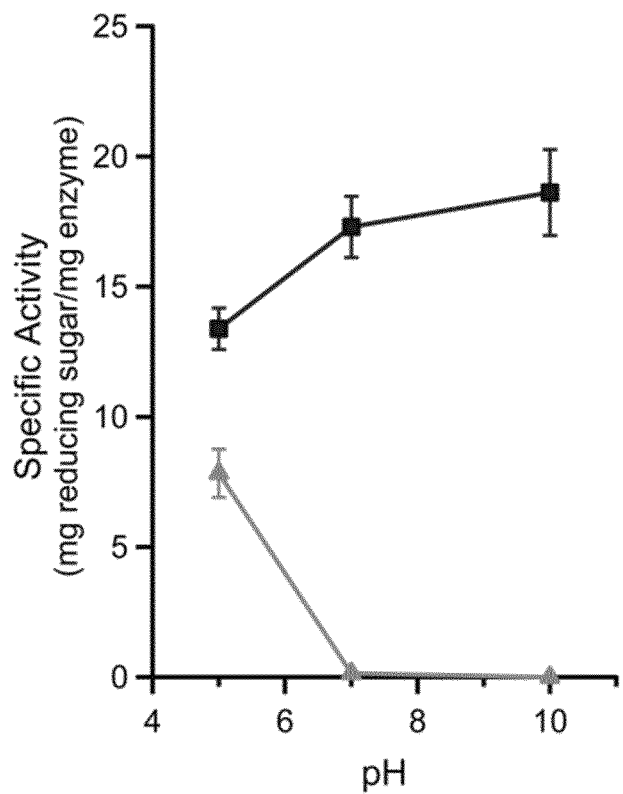

All the experiments described until now were carried out using filter-paper, a common substrate very used for the determination of the activity of cellulase cocktails. Nevertheless, there is a huge interest in the hydrolysis of crystalline cellulose in industry. That is why, it was decided to test the activity of the ancestral cocktail using a completely crystalline substrate as it is the case of Avicel. For this porpoise, the assay as shown in FIG. 5 was carried out at different temperatures (40-70° C.) in three different pH values (5, 7 and 10). The incubation for this assay was performed for 24 hours in agitation. The figure clearly shows (FIG. 5) that the specific activity of the ancestral cocktail is also higher in this case. This difference becomes even bigger when the temperature and the pH values are higher. So, this assay shows that the ancestral cocktail is not only able to degrade amorphous cellulose in a better way, but also its activity is higher with crystalline cellulose. Although these are really interesting results, both filter-paper and avicel are 100% cellulose containing substrates and there is a need of hydrolysing not only cellulosic substrates but also lignocellulosic materials as it was mentioned before.

Lignocellulosic Substrates Hydrolysis

Figure 6:
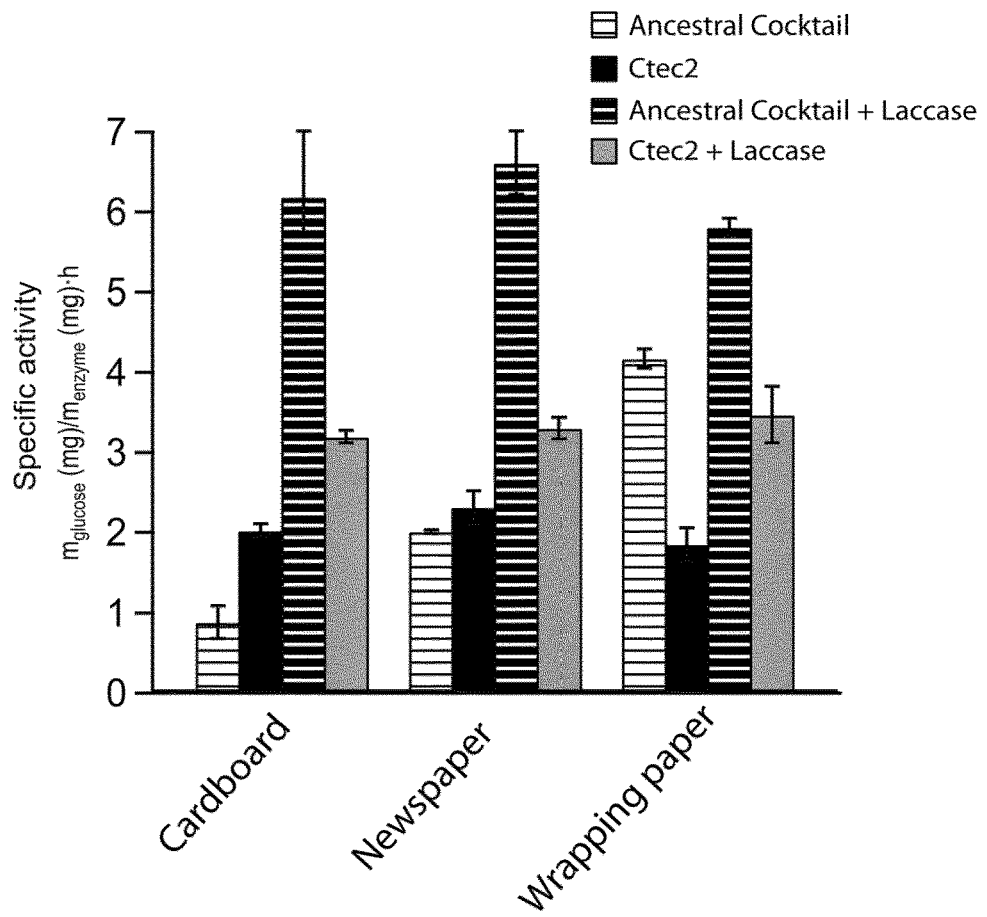
FIG. 6. Activities of ancestral enzyme cocktail (CKA), commercial enzyme cocktail (CTec2), ancestral enzyme cocktail in presence of *T. pubescens* laccase (CKA+L) and commercial enzyme cocktail in presence of *T. pubescens* laccase (Ctec2+L) at 50° C. and pH 4.8. Assays were carried out in three different substrates: cardboard, newspaper and wrapping paper.

Activity assays were carried with three different substrates (cardboard, newspaper and wrapping paper). The values obtained at 50° C. and pH 4.8 can be seen in FIG. 6. These values show that the ancestral cocktail has higher activity in all the substrates when laccase was added to the cocktail. As laccase degrades lignin, so cellulose was more accessible for the cellulases present in the cocktail. In these conditions, where cellulose was more accessible, the higher specific activity of the ancestral cocktail was measured, almost doubling the activity of the commercial cocktail Ctec2. It was expected that the commercial cocktail Ctec2 contains other enzymes such as xylanases and laccase in addition to the cellulases that favor the degradation. This can be the reason for the observed lower activities of the ancestral cocktail in absence of laccase.

It can be also observed that the activity is substrate dependent. Substrates have different cellulose, hemicellulose and lignin content. In addition, they went through different mechanical and chemical processes in their production. This may define the arrangement of the lignocellulosic fibers and therefore, as well as being different in composition they are different in structure. This diversity of substrate's characteristics may affect the ability of enzymes to reach their specific substrate and degrade it.

Comparing these results with the ones obtained in filter-paper ideal substrate (FIG. 1), lower values are obtained in lignocellulosic substrates. Filter-paper is pure cellulose that is synthetized in the laboratory. In contrast, lignocellulosic biomass is a complex substrate due to its structure and composition. Lignin and hemicellulose form a protective shell around cellulose, which obstructs enzymatic attack and thus, lower amount of glucose is released.

Figure 7:
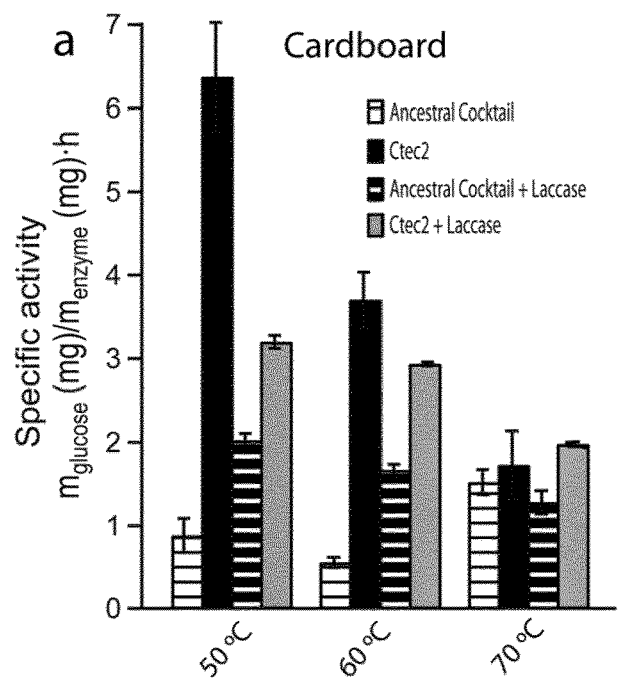
FIG. 7. Activities of ancestral enzyme cocktail (CKA), commercial enzyme cocktail (CTec2), ancestral cocktail in presence of *T. pubescens* laccase (CKA+L) and commercial enzyme cocktail in presence of *T. pubescens* laccase (CTec2+L) at 50-70° C. temperature range and pH 4.8. Assays were carried out in three different substrates: cardboard (a), newspaper (b) and wrapping paper (c).
Figure 7:
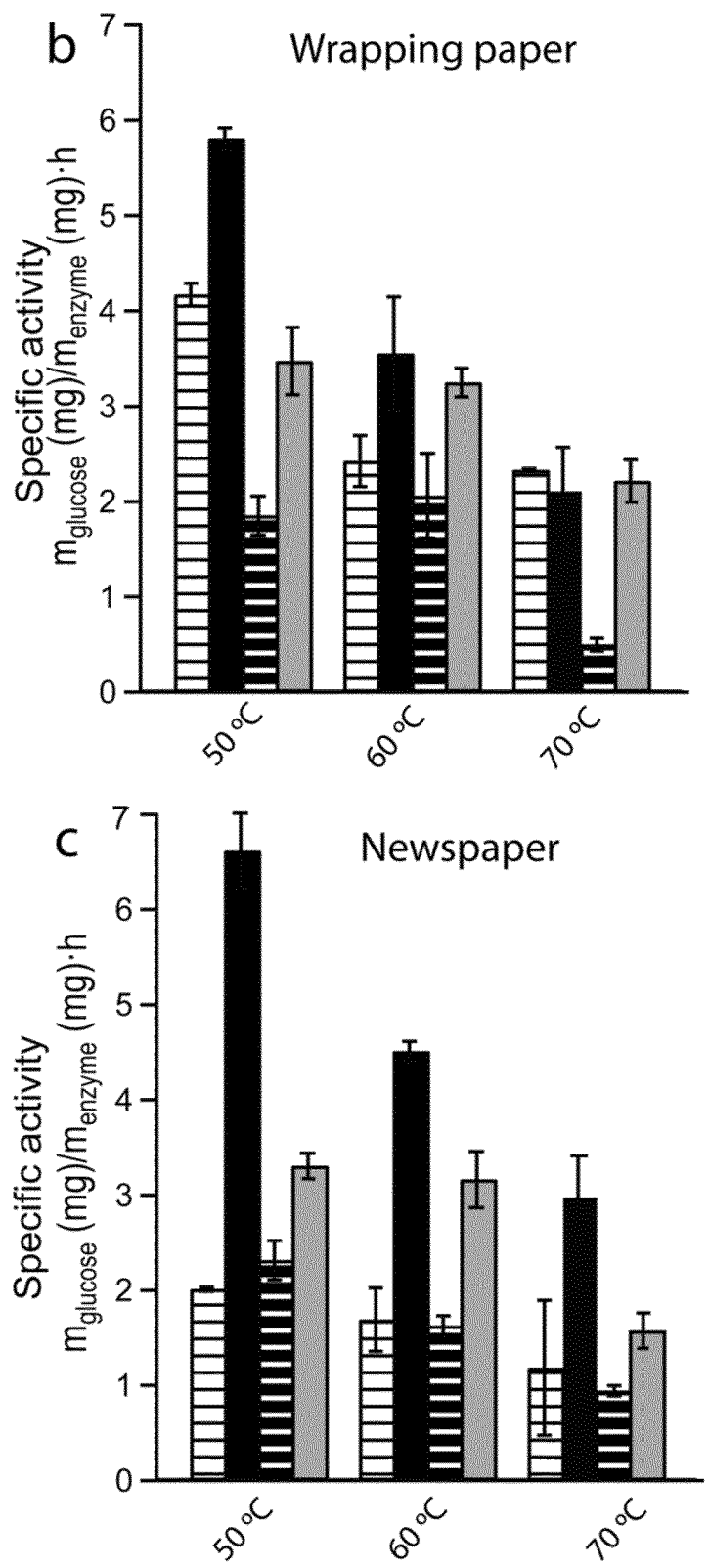

Those assays were repeated in different temperatures; the activity values obtained at a temperature range of 50–70° C. were plotted (FIG. 7). In all the tested substrates, the highest activity was obtained at 50° C. with the ancestral cellulases cocktail together with the laccase. As saw before in FIG. 6, the laccase influence was really positive and the activity of ancestral cellulases was higher than using the commercial ones Ctec2. Regarding temperature, its increment resulted in lower activities. At 70° C. similar values were observed when the assay was carried out with or without laccase. This may happen due to the fact that laccase is not active at that temperature. If laccase losses its activity the accessibility of cellulose is reduced and thus, less cellulose is degraded to glucose.

As mentioned before, the commercial cellulase cocktail Ctec2 contains other enzymes that favor the hydrolysis. Thereby, in some cases lower activities of the ancestral cocktail were observed when laccase was not added.

SEQUENCE LISTING

This application contains a Sequence Listing which has been submitted electronically in ASCII format and is hereby incorporated by reference in its entirety.

The ASCII text file name is: 14_SQL.txt
Creation date: 18 Jun. 2020
Size: 105,651 bytes.

---

The invention claimed is:

1. A polypeptide having beta-glucosidase activity comprising a sequence selected from the group consisting of SEQ ID NO: 6, SEQ ID NO: 7 and SEQ ID NO: 8, or a functionally equivalent variant thereof that substantially maintains its catalytic activity, wherein the functionally equivalent variant has at least 70% sequence identity to one or more of SEQ ID NO: 6, SEQ ID NO: 7 or SEQ ID NO: 8, or wherein the functionally equivalent variant has the sequence of SEQ ID NO: 10.

2. A nucleic acid encoding a polypeptide according to claim 1, a vector comprising said nucleic acid, or a host cell comprising said nucleic acid or said vector.

3. A method for hydrolysing cellobiose and/or cellotetraose within a sample containing cellobiose and/or cellotetraose to glucose comprising contacting said sample with a polypeptide according to claim 1 under suitable conditions for hydrolysing the cellobiose and/or the cellotetraose to glucose.

4. An enzyme cocktail comprising:
   (i) a polypeptide having beta-glucosidase activity comprising a sequence selected from the group consisting of SEQ ID NO: 6, SEQ ID NO: 7 and SEQ ID NO: 8, or a functionally equivalent variant thereof that substantially maintains its catalytic activity, wherein the functionally equivalent variant has at least 70% sequence identity to one or more of SEQ ID NO: 6, SEQ ID NO: 7 or SEQ ID NO: 8, or wherein the functionally equivalent variant has the sequence of SEQ ID NO: 10 and
   (ii) an endoglucanase and/or a polypeptide having exoglucanase activity.

5. The enzyme cocktail according to claim 4 wherein: (i) the polypeptide having exoglucanase activity is a polypeptide comprising an exoglucanase catalytic domain, wherein the catalytic domain comprises a sequence selected from the group consisting of SEQ ID NO: 1, SEQ ID NO: 2 and SEQ ID NO: 3, or a functionally equivalent variant thereof that substantially maintains its catalytic activity, wherein said functionally equivalent variant has at least 70% sequence identity to one or more of SEQ ID NO: 1, SEQ ID NO: 2 or SEQ ID NO: 3, wherein said polypeptide further comprises a carbohydrate binding domain and/or (iii) the endoglucanase comprises a catalytic domain comprising a sequence selected from the group consisting of SEQ ID NO: 11, SEQ ID NO: 12 and SEQ ID NO: 13.

6. The enzyme cocktail according to claim 5, wherein the endoglucanase comprises a carbohydrate binding domain of sequence SEQ ID NO: 14.

7. The enzyme cocktail according to claim 6, further comprising a laccase and/or further comprising a xylanase.

8. A method for hydrolysing cellulose to glucose comprising contacting a sample comprising cellulose with the enzyme cocktail of claim 4 under suitable conditions for hydrolysing cellulose to glucose, wherein said enzyme cocktail comprises a polypeptide having exoglucanase activity, an endoglucanase and a polypeptide having beta-glucosidase activity.

9. The method according to claim 8, wherein the cellulose is contained in a lignocellulosic material, and wherein the enzyme cocktail comprises a laccase and a xylanase.

10. The method according to claim 8, wherein the suitable conditions for hydrolysing cellulose to glucose comprise incubating the sample comprising cellulose and the enzyme cocktail at a pH between 7 and 11.

11. A method for producing bioethanol comprising
   (i) hydrolysing cellulose to glucose following the method according to claim 8 and converting the glucose obtained in step (i) to bioethanol in the presence of a yeast capable of producing bioethanol by fermentation of glucose.

* * * * *